US008574599B1

(12) United States Patent
McCluskie et al.

(10) Patent No.: US 8,574,599 B1
(45) Date of Patent: Nov. 5, 2013

(54) METHODS AND PRODUCTS FOR INDUCING MUCOSAL IMMUNITY

(75) Inventors: Michael J. McCluskie, Ottawa (CA); Heather L. Davis, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 0 days.

(21) Appl. No.: 09/316,199

(22) Filed: May 21, 1999

Related U.S. Application Data

(60) Provisional application No. 60/086,393, filed on May 22, 1998.

(51) Int. Cl.
*A61K 45/00* (2006.01)
*A61K 39/00* (2006.01)

(52) U.S. Cl.
USPC .................................. 424/278.1; 424/184.1

(58) Field of Classification Search
USPC .............................. 514/44, 2; 435/320.1, 455
See application file for complete search history.

(56) References Cited

U.S. PATENT DOCUMENTS

| | | |
|---|---|---|
| 3,906,092 A | 9/1975 | Hilleman et al. |
| 4,452,775 A | 6/1984 | Kent |
| 4,544,559 A | 10/1985 | Gil et al. |
| 4,627,850 A | 12/1986 | Deters et al. |
| 4,806,463 A | 2/1989 | Goodchild et al. |
| 4,994,442 A | 2/1991 | Gil et al. |
| 5,004,810 A | 4/1991 | Draper |
| 5,066,500 A | 11/1991 | Gil et al. |
| 5,166,195 A | 11/1992 | Ecker |
| 5,194,428 A | 3/1993 | Agrawal et al. |
| 5,248,670 A | 9/1993 | Draper et al. ..................... 514/44 |
| 5,264,423 A | 11/1993 | Cohen et al. |
| 5,276,019 A | 1/1994 | Cohen et al. |
| 5,457,189 A | 10/1995 | Crooke et al. |
| 5,514,577 A | 5/1996 | Draper et al. |
| 5,585,479 A | 12/1996 | Hoke et al. ..................... 536/24.5 |
| 5,594,122 A | 1/1997 | Friesen |
| 5,663,153 A | 9/1997 | Hutcherson et al. ............. 514/44 |
| 5,679,647 A | 10/1997 | Carson et al. |
| 5,684,147 A | 11/1997 | Agrawal et al. |
| 5,723,335 A | 3/1998 | Hutcherson et al. |
| 5,780,448 A | 7/1998 | Davis |
| 5,786,189 A | 7/1998 | Locht et al. ................. 435/172.3 |
| 5,804,566 A | 9/1998 | Carson et al. |
| 5,830,877 A | 11/1998 | Carson et al. |
| 5,840,332 A | 11/1998 | Lerner et al. |
| 5,849,719 A | 12/1998 | Carson et al. ..................... 514/44 |
| 5,877,309 A | 3/1999 | McKay et al. |
| 5,972,346 A | 10/1999 | Hauser et al. |
| 5,985,847 A | 11/1999 | Carson et al. |
| 6,030,955 A | 2/2000 | Stein et al. |
| 6,042,838 A * | 3/2000 | Briles et al. ................. 424/244.1 |
| 6,086,898 A | 7/2000 | DeKruyff et al. |
| 6,090,791 A | 7/2000 | Sato et al. ..................... 514/44 |
| 6,133,244 A * | 10/2000 | Michel et al. ..................... 514/44 |
| 6,174,872 B1 | 1/2001 | Carson et al. |
| 6,184,369 B1 | 2/2001 | Rando et al. |
| 6,194,388 B1 * | 2/2001 | Krieg et al. ..................... 514/44 |
| 6,207,646 B1 * | 3/2001 | Krieg et al. ..................... 514/44 |
| 6,210,663 B1 | 4/2001 | Ertl |
| 6,214,804 B1 | 4/2001 | Felgner et al. |
| 6,214,806 B1 | 4/2001 | Krieg et al. |
| 6,218,371 B1 * | 4/2001 | Krieg et al. ..................... 514/44 |
| 6,221,882 B1 | 4/2001 | Macfarlane |
| 6,239,116 B1 * | 5/2001 | Krieg et al. ..................... 514/44 |
| 6,248,720 B1 | 6/2001 | Mathiowitz et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,426,334 B1 * | 7/2002 | Agrawal et al. ................. 514/44 |
| 6,429,199 B1 | 8/2002 | Krieg et al. |
| 6,479,504 B1 | 11/2002 | Macfarlane et al. |
| 6,498,147 B2 | 12/2002 | Nerenberg et al. |
| 6,498,148 B1 | 12/2002 | Raz |
| 6,503,533 B1 | 1/2003 | Korba et al. |
| 6,506,386 B1 | 1/2003 | Friede et al. |
| 6,514,948 B1 | 2/2003 | Raz et al. |
| 6,521,637 B2 | 2/2003 | Macfarlane |
| 6,534,062 B2 | 3/2003 | Raz et al. |
| 6,544,518 B1 | 4/2003 | Friede et al. |
| 6,552,006 B2 | 4/2003 | Raz et al. |
| 6,558,670 B1 | 5/2003 | Friede et al. |
| 6,562,798 B1 | 5/2003 | Schwartz |
| 6,589,940 B1 | 7/2003 | Raz et al. |

(Continued)

FOREIGN PATENT DOCUMENTS

| | | |
|---|---|---|
| CN | 1 468 957 | 1/2004 |
| EP | 0468520 | 1/1992 |

(Continued)

OTHER PUBLICATIONS

Krieg et al., The role of CpG dinucleotides in DNA vaccines, Jan. 1998, Trends in Microbiology, vol. 6, No. 1.*
Hodes (Fundamental Immunology, 2ed., pp. 587-620, 1989).*
Kincy-Cain et al., Infection and Immunity, 1996, 64: 1437-1440.*
Belyakov et al., Proc. Natl. Acad. Sci. USA, Feb. 1998, 95: 1709-1714.*
Bergmann et al., Rev. Infect. Dis., 1988, 10: 939-950, Abstract.*
Lipford G., et al., "CpG-containing synthetic oligonucleotides promote B and cytotoxic T cell responses to protein antigen: a new class of vaccine adjuvants", *Eur. J. Immunol.*, (1997), 27:2340-2344.
McCluskie, M., et al., "CpG DNA is a potent enhancer of specific immunity in mice immunized with recombinant hepatitis B surface antigen", *J of Immunol*, (1999), 1:162:5:3103.
Liu, H., et al., "Immunostimulatory CpG oligodeoxynucleotides enhance the immune response to vaccine strategies involving granulocyte-macrophage colony-stimulating factor", *BLOOD*, (1998), 92:10:3730-3736.

(Continued)

*Primary Examiner* — Ileana Popa
(74) *Attorney, Agent, or Firm* — Wolf, Greenfield & Sacks, P.C.

(57) ABSTRACT

The invention relates methods and products for inducing mucosal immunity. In particular, the invention relates to the use of immunostimulatory oligonucleotides containing a CpG motif for inducing mucosal immunity. The CpG immunostimulatory oligonucleotides may be administered alone or in combination with antigen and/or with other adjuvants.

52 Claims, 13 Drawing Sheets

(56) References Cited

U.S. PATENT DOCUMENTS

| | | | |
|---|---|---|---|
| 6,607,732 B2* | 8/2003 | Morein et al. | 424/278.1 |
| 6,610,661 B1 | 8/2003 | Carson et al. | |
| 6,613,751 B2 | 9/2003 | Raz et al. | |
| 6,630,455 B1 | 10/2003 | Mitchell | |
| 6,653,292 B1 | 11/2003 | Krieg et al. | |
| 6,689,757 B1* | 2/2004 | Craig | 514/44 |
| 6,693,086 B1 | 2/2004 | Dow et al. | |
| 6,727,230 B1* | 4/2004 | Hutcherson et al. | 514/44 |
| 6,737,066 B1 | 5/2004 | Moss | |
| 6,749,856 B1* | 6/2004 | Berzofsky et al. | 424/188.1 |
| 6,821,957 B2 | 11/2004 | Davis et al. | |
| 6,852,705 B2 | 2/2005 | Audonnet et al. | |
| 6,943,240 B2 | 9/2005 | Bauer et al. | |
| 6,949,520 B1 | 9/2005 | Hartmann et al. | |
| 7,001,890 B1 | 2/2006 | Wagner et al. | |
| 7,049,302 B1 | 5/2006 | Kensil | |
| 7,223,741 B2 | 5/2007 | Krieg | |
| 7,271,156 B2 | 9/2007 | Krieg et al. | |
| 7,354,711 B2 | 4/2008 | Macfarlane | |
| 7,402,572 B2 | 7/2008 | Krieg et al. | |
| 7,410,975 B2 | 8/2008 | Lipford et al. | |
| 2001/0034330 A1 | 10/2001 | Kensil | |
| 2001/0036462 A1 | 11/2001 | Fong et al. | |
| 2001/0044416 A1 | 11/2001 | McCluskie et al. | |
| 2001/0046967 A1 | 11/2001 | Van Nest et al. | |
| 2002/0028784 A1 | 3/2002 | Van Nest et al. | |
| 2002/0042387 A1 | 4/2002 | Raz et al. | |
| 2002/0055477 A1 | 5/2002 | Nest et al. | |
| 2002/0064515 A1 | 5/2002 | Krieg et al. | |
| 2002/0086839 A1 | 7/2002 | Raz et al. | |
| 2002/0091097 A1 | 7/2002 | Bratzler et al. | |
| 2002/0098199 A1 | 7/2002 | Van Nest et al. | |
| 2002/0107212 A1 | 8/2002 | Van Nest et al. | |
| 2002/0142977 A1 | 10/2002 | Raz et al. | |
| 2002/0142978 A1 | 10/2002 | Raz et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0192184 A1 | 12/2002 | Carpentier | |
| 2002/0198165 A1 | 12/2002 | Bratzler et al. | |
| 2003/0026782 A1 | 2/2003 | Krieg et al. | |
| 2003/0026801 A1 | 2/2003 | Weiner et al. | |
| 2003/0049266 A1 | 3/2003 | Fearson et al. | |
| 2003/0050261 A1 | 3/2003 | Krieg et al. | |
| 2003/0050263 A1 | 3/2003 | Krieg et al. | |
| 2003/0050268 A1 | 3/2003 | Krieg et al. | |
| 2003/0055014 A1 | 3/2003 | Bratzler | |
| 2003/0078223 A1 | 4/2003 | Raz et al. | |
| 2003/0087848 A1 | 5/2003 | Bratzler et al. | |
| 2003/0091599 A1 | 5/2003 | Davis et al. | |
| 2003/0092663 A1 | 5/2003 | Raz | |
| 2003/0100527 A1 | 5/2003 | Krieg et al. | |
| 2003/0104044 A1 | 6/2003 | Semple et al. | |
| 2003/0104523 A1 | 6/2003 | Bauer et al. | |
| 2003/0109469 A1 | 6/2003 | Carson et al. | |
| 2003/0119773 A1 | 6/2003 | Raz et al. | |
| 2003/0125279 A1 | 7/2003 | Junghans et al. | |
| 2003/0125292 A1 | 7/2003 | Semple et al. | |
| 2003/0130217 A1 | 7/2003 | Raz et al. | |
| 2003/0133988 A1 | 7/2003 | Fearon et al. | |
| 2003/0138413 A1 | 7/2003 | Vicari et al. | |
| 2003/0139364 A1 | 7/2003 | Krieg et al. | |
| 2003/0143213 A1 | 7/2003 | Raz et al. | |
| 2003/0147870 A1 | 8/2003 | Raz et al. | |
| 2003/0148316 A1 | 8/2003 | Lipford et al. | |
| 2003/0148976 A1 | 8/2003 | Krieg et al. | |
| 2003/0165478 A1 | 9/2003 | Sokoll et al. | |
| 2003/0166001 A1 | 9/2003 | Lipford | |
| 2003/0176389 A1 | 9/2003 | Raz et al. | |
| 2003/0181406 A1 | 9/2003 | Schetter et al. | |
| 2003/0186921 A1 | 10/2003 | Carson et al. | |
| 2003/0191079 A1 | 10/2003 | Krieg et al. | |
| 2003/0203861 A1 | 10/2003 | Carson et al. | |
| 2003/0212026 A1 | 11/2003 | Krieg et al. | |
| 2003/0212028 A1 | 11/2003 | Raz et al. | |
| 2003/0224010 A1 | 12/2003 | Davis et al. | |
| 2003/0232074 A1 | 12/2003 | Lipford et al. | |
| 2003/0232443 A1 | 12/2003 | Bennett et al. | |
| 2003/0232780 A1 | 12/2003 | Carson et al. | |
| 2003/0232856 A1 | 12/2003 | Macfarlane | |
| 2004/0006010 A1 | 1/2004 | Carson et al. | |
| 2004/0006034 A1 | 1/2004 | Raz et al. | |
| 2004/0009942 A1 | 1/2004 | Van Nest et al. | |
| 2004/0009949 A1 | 1/2004 | Krieg | |
| 2004/0013688 A1 | 1/2004 | Wise et al. | |
| 2004/0030118 A1 | 2/2004 | Wagner et al. | |
| 2004/0053880 A1 | 3/2004 | Krieg | |
| 2004/0067902 A9 | 4/2004 | Bratzler et al. | |
| 2004/0067905 A1 | 4/2004 | Krieg | |
| 2004/0087534 A1 | 5/2004 | Krieg et al. | |
| 2004/0087538 A1 | 5/2004 | Krieg et al. | |
| 2004/0092468 A1 | 5/2004 | Schwartz et al. | |
| 2004/0092472 A1 | 5/2004 | Krieg | |
| 2004/0106568 A1 | 6/2004 | Krieg et al. | |
| 2004/0115219 A1 | 6/2004 | Ahn et al. | |
| 2004/0131628 A1 | 7/2004 | Bratzler et al. | |
| 2004/0132685 A1 | 7/2004 | Krieg et al. | |
| 2004/0142469 A1 | 7/2004 | Krieg et al. | |
| 2004/0143112 A1 | 7/2004 | Krieg et al. | |
| 2004/0147468 A1 | 7/2004 | Krieg et al. | |
| 2004/0152649 A1 | 8/2004 | Krieg | |
| 2004/0152656 A1 | 8/2004 | Krieg et al. | |
| 2004/0152657 A1 | 8/2004 | Krieg et al. | |
| 2004/0157791 A1 | 8/2004 | Dow et al. | |
| 2004/0162258 A1 | 8/2004 | Krieg et al. | |
| 2004/0162262 A1 | 8/2004 | Krieg et al. | |
| 2004/0167089 A1 | 8/2004 | Krieg et al. | |
| 2004/0171150 A1 | 9/2004 | Krieg et al. | |
| 2004/0171571 A1 | 9/2004 | Krieg et al. | |
| 2004/0181045 A1 | 9/2004 | Krieg et al. | |
| 2004/0198680 A1 | 10/2004 | Krieg | |
| 2004/0198688 A1 | 10/2004 | Krieg et al. | |
| 2004/0229835 A1 | 11/2004 | Krieg et al. | |
| 2004/0234512 A1 | 11/2004 | Wagner et al. | |
| 2004/0235770 A1 | 11/2004 | Davis et al. | |
| 2004/0235774 A1 | 11/2004 | Bratzler et al. | |
| 2004/0235777 A1 | 11/2004 | Wagner et al. | |
| 2004/0235778 A1 | 11/2004 | Wagner et al. | |
| 2004/0247662 A1 | 12/2004 | Dow et al. | |
| 2004/0266719 A1 | 12/2004 | McCluskie et al. | |
| 2005/0004061 A1 | 1/2005 | Krieg et al. | |
| 2005/0004062 A1 | 1/2005 | Krieg et al. | |
| 2005/0009774 A1 | 1/2005 | Krieg et al. | |
| 2005/0019340 A1 | 1/2005 | Garcon et al. | |
| 2005/0031638 A1 | 2/2005 | Dalemans et al. | |
| 2005/0032734 A1 | 2/2005 | Davis et al. | |
| 2005/0032736 A1 | 2/2005 | Krieg et al. | |
| 2005/0037403 A1 | 2/2005 | Krieg et al. | |
| 2005/0037985 A1 | 2/2005 | Krieg et al. | |
| 2005/0043529 A1 | 2/2005 | Davis et al. | |
| 2005/0049215 A1 | 3/2005 | Krieg et al. | |
| 2005/0049216 A1 | 3/2005 | Krieg et al. | |
| 2005/0054601 A1 | 3/2005 | Wagner et al. | |
| 2005/0054602 A1 | 3/2005 | Krieg et al. | |
| 2005/0059619 A1 | 3/2005 | Krieg et al. | |
| 2005/0059625 A1 | 3/2005 | Krieg et al. | |
| 2005/0070491 A1 | 3/2005 | Krieg et al. | |
| 2005/0075302 A1 | 4/2005 | Hutcherson et al. | |
| 2005/0100983 A1 | 5/2005 | Bauer et al. | |
| 2005/0101554 A1 | 5/2005 | Krieg et al. | |
| 2005/0101557 A1 | 5/2005 | Krieg et al. | |
| 2005/0119273 A1 | 6/2005 | Lipford et al. | |
| 2005/0123523 A1 | 6/2005 | Krieg et al. | |
| 2005/0130911 A1 | 6/2005 | Uhlmann et al. | |
| 2005/0148537 A1 | 7/2005 | Krieg et al. | |
| 2005/0169888 A1 | 8/2005 | Hartmann et al. | |
| 2005/0171047 A1 | 8/2005 | Krieg et al. | |
| 2005/0176672 A1 | 8/2005 | Scheule et al. | |
| 2005/0181422 A1 | 8/2005 | Bauer et al. | |
| 2005/0182017 A1 | 8/2005 | Krieg | |
| 2005/0197314 A1 | 9/2005 | Krieg et al. | |
| 2005/0209184 A1 | 9/2005 | Klinman et al. | |
| 2005/0215501 A1 | 9/2005 | Lipford et al. | |
| 2005/0233995 A1 | 10/2005 | Krieg et al. | |

(56) References Cited

U.S. PATENT DOCUMENTS

| | | |
|---|---|---|
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0249794 A1 | 11/2005 | Semple et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0223769 A1 | 10/2006 | Dow et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0202575 A1 | 8/2007 | Klinman et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |

FOREIGN PATENT DOCUMENTS

| | | |
|---|---|---|
| EP | 0302758 B1 | 3/1994 |
| EP | 1 187 629 A2 | 10/2000 |
| KR | 2001063153 | 7/2001 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 93/15207 A2 | 8/1993 |
| WO | WO 94/19945 | 9/1994 |
| WO | WO 95/05853 | 3/1995 |
| WO | WO 95/24929 A2 | 9/1995 |
| WO | WO 95/26204 | 10/1995 |
| WO | 96-02555 * | 2/1996 |
| WO | WO 96/02555 | 2/1996 |
| WO | WO 96/13277 A1 | 5/1996 |
| WO | WO 96/14074 A1 | 5/1996 |
| WO | WO 96/35782 | 11/1996 |
| WO | WO 96/40162 A1 | 12/1996 |
| WO | WO 97/03702 A1 | 2/1997 |
| WO | WO 97/12633 A1 | 4/1997 |
| WO | WO 97/26802 A1 | 7/1997 |
| WO | WO 97/28259 | 8/1997 |
| WO | WO 97/30728 A1 | 8/1997 |
| WO | WO 98/01538 A1 | 1/1998 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/37919 A1 | 9/1998 |
| WO | WO 98/40100 | 9/1998 |
| WO | WO 98/40100 A1 | 9/1998 |
| WO | WO 98/49288 A1 | 11/1998 |
| WO | WO 98/49348 A1 | 11/1998 |
| WO | WO 98/51278 A2 | 11/1998 |
| WO | WO 98/52581 | 11/1998 |
| WO | WO 98/52962 * | 11/1998 |
| WO | WO 98/52962 A1 | 11/1998 |
| WO | WO 98/55495 | 12/1998 |
| WO | WO 98/55609 A1 | 12/1998 |
| WO | WO 99/11275 | 3/1999 |
| WO | WO 99/30686 A1 | 6/1999 |
| WO | WO 99/33488 | 7/1999 |
| WO | WO 99/33868 A2 | 7/1999 |
| WO | WO 99/43350 | 9/1999 |
| WO | WO 99/51259 A2 | 10/1999 |
| WO | WO 99/52549 A1 | 10/1999 |
| WO | WO 99/55743 A1 | 11/1999 |
| WO | WO 99/56755 A1 | 11/1999 |
| WO | WO 99/58118 A2 | 11/1999 |
| WO | WO 99/61056 A2 | 12/1999 |
| WO | WO 99/62923 | 12/1999 |
| WO | WO 00/03683 A2 | 1/2000 |
| WO | WO 00/06588 A1 | 2/2000 |
| WO | WO 00/09159 A1 | 2/2000 |
| WO | WO 00/14217 A2 | 3/2000 |
| WO | WO 00/15256 A2 | 3/2000 |
| WO | WO 00/20039 | 4/2000 |
| WO | WO 00/21556 A1 | 4/2000 |
| WO | WO 00/23105 A2 | 4/2000 |
| WO | WO 00/41463 A2 | 7/2000 |
| WO | WO 00/46365 A1 | 8/2000 |
| WO | WO 00/54803 A2 | 9/2000 |
| WO | WO 00/56359 A2 | 9/2000 |
| WO | WO 00/62787 A1 | 10/2000 |
| WO | WO 00/62800 A2 | 10/2000 |
| WO | WO 00/67023 A1 | 11/2000 |
| WO | WO 00/67787 A2 | 11/2000 |
| WO | WO 00/75304 A1 | 12/2000 |
| WO | WO 01/00231 A2 | 1/2001 |
| WO | WO 01/00232 A2 | 1/2001 |
| WO | WO 01/02007 A1 | 1/2001 |
| WO | WO 01/12223 A2 | 2/2001 |
| WO | WO 01/17550 A1 | 3/2001 |
| WO | WO 01/17551 A2 | 3/2001 |
| WO | WO 01/22972 A2 | 4/2001 |
| WO | WO 01/35991 A2 | 5/2001 |
| WO | WO 01/45750 A1 | 6/2001 |
| WO | WO 01/54719 A2 | 8/2001 |
| WO | WO 01/55341 A2 | 8/2001 |
| WO | WO 01/62207 A2 | 8/2001 |
| WO | WO 01/62909 A1 | 8/2001 |
| WO | WO 01/68077 A2 | 9/2001 |
| WO | WO 01/68078 A2 | 9/2001 |
| WO | WO 01/68103 A2 | 9/2001 |
| WO | WO 01/68116 A2 | 9/2001 |
| WO | WO 01/68117 A2 | 9/2001 |
| WO | WO 01/68143 A2 | 9/2001 |
| WO | WO 01/68144 A2 | 9/2001 |
| WO | WO 01/72123 A1 | 10/2001 |
| WO | WO 02/09748 A1 | 2/2002 |
| WO | WO 02/24225 A1 | 3/2002 |
| WO | WO 02/28428 A2 | 4/2002 |
| WO | WO 02/36767 A3 | 5/2002 |
| WO | WO 02/074922 A2 | 9/2002 |
| WO | WO 02/102307 A2 | 12/2002 |

(56) References Cited

FOREIGN PATENT DOCUMENTS

| | | |
|---|---|---|
| WO | WO 03/014316 A2 | 2/2003 |
| WO | WO 03/020889 A2 | 3/2003 |
| WO | WO 03/026688 A1 | 4/2003 |
| WO | WO 03/030934 A2 | 4/2003 |
| WO | WO 03/094963 A2 | 11/2003 |
| WO | WO 03/100040 A1 | 12/2003 |
| WO | WO 2004/007743 A2 | 1/2004 |
| WO | WO 2004/026888 A2 | 4/2004 |
| WO | WO 2004/094671 A2 | 11/2004 |
| WO | WO 2006/080946 A2 | 8/2006 |
| WO | WO 2007/031877 A2 | 3/2007 |
| WO | WO 2007/038720 A2 | 4/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Klinman, D., et al., CpG motifs as immune adjuvants *Vaccine, GB, Butterworth Scientific Guildford*, 17:1:19-25.

DeLong, R. et al., "Characterization of Complexes of Oligonucleotides with Polyamidoamine Starburst Dendrimers and Effects on Intracellular Delivery", Journal of Pharmaceutical Sciences, vol. 86, No. 6, Jun. 1997.

Snider, D.P., "The Mucosal Adjuvant Activities of ADP-Ribosylating Bacterial Enterotoxins", Critical Reviews in Immunology 15(3&4):317-348 (1995).

Staats, H.F. et al., "Mucosal immunity to infection with implications for vaccine development", Current Opinion in Immunology 1994, 6:572-583.

O'Hagan, D.T., Ph.D., "Novel Delivery Systems for Oral Vaccines", 1994, pp. 1-24.

Lamm, M.E. et al., "Mechanism of IgA-Mediated Mucosal Defense", Vaccine Research, vol. 1, No. 3, 1992, pp. 169-173.

Constant, S.L. et al., Induction of TH1 and TH2 CD4+ T Cell Responses: The Alternative Approaches, Annu. Rev. Immunol. 1997, 15:297-322, 1997.

Bowersock, T.L. et al., "Evaluation of an orally administered vaccine, using hydrogels containing bacterial exotoxins Of Pasteurella haemolytica, in cattle", Am. J. Vet. Res., vol. 55, No. 4, Apr. 1994, pp. 502-509.

Hogg, J.C., "The Pathology of Asthma", APMIS 105: 735-745, 1997.

Gregoriadis, G., "Engineering liposomes for drug delivery: progress and problems", TIBTECH Dec. 1995 (vol. 13), pp. 527-537.

Sjolander, A. et al., "Kinetics, Localization and Isotype Profile of Antibody Responses to Immune Stimulating Complexes (Iscoms) Containing Human Influenza Virus Envelope Glycoprotiens", Scand. J. Immunol. 43, 164-172, 1996.

Douce, G. et al., "Mutants of *Echerichia coli* heat-labile toxin lacking ADP-ribosyltransferase activity act as nontoxic, mucosal adjuvants", Proc. Natl. Acad. Sci. USA vol. 92, pp. 1644-1648, Feb. 1995 Immunology.

Pizza, M. et al., "A Genetically Detoxified Derivative of Heat-Labile *Escherichia coli* Enterotoxin Induces Neutralizing Antibodies against the A Subunit", J. Exp. Med. vol. 180, Dec. 1994, pp. 2147-2153.

Alper Oya, H. et al., "Potential of Particulate Carriers for the Mucosal Delivery of DNA Vaccines", Biochemical Society Transactions (1997), 25, 337S.

Holmgren, J. et al., "Cholera toxin and cholera B subunit as oral-mucosal adjuvant and antigen vector systems".

O'Hagan, D.T. et al., "Controlled release microparticles for oral immunization", International Journal of Pharmaceutics, 108 (1994) 133-139.

Haneberg, B. et al., "Induction of Specific Immunoglobulin A in the Small Intestine, Colon-Rectum, and Vagina Measured by a New Method for Collection of Secretions from Local Mucosal Surfaces", Infection and Immunity, Jan. 1994, p. 15-23, pp. 1589-1595, 1995.

Tokunaga, T. et al., "Antitumor Activity of Deoxyribonucleic Acid Fraction From *Mycobacterium bovis* BCG. I. Isolation, Physicochemical Characterization, and Antitumor Activity", Jnci. vol. 72, No. 4, Apr. 1984, pp. 955-962.

Rappuoli, R. et al., "Genetic Detoxification of Bacterial Toxins: A New Approach to Vaccine Development", In Arch Allergy Immunol. 1995; 108:327-333.

DeHaan, L. et al., "Mutants of the *Escherichia coli* Heat-Labile Enterotoxin with Reduced ADP-Ribosylation Activity or No Activity Retain the Immunogenic Properties of the Native Holotoxin", Infection and Immunity, Dec. 1996, p. 5413-5416.

Kay, A.B., "TH2-Type Cytokines in Asthma", Allergy and Clinical Immunology, 1-8.

Spangler, B.D., "Structure and Function of Cholera Toxin and the Related *Escherichia coli* Heat-Labile Enterotoxin", Microbiological Reviews, Dec. 1992, p. 622-647, vol. 56, No. 4.

Eldgridge, J.H. et al., "Biodegradable Microspheres as a Vaccine Delivery System", Molecular Immunology, vol. 28, No. 3, pp. 287-294, 1991.

Lycke, N. et al., "The adjuvant effect of Vibrio cholerae and *Escherichia coli* heat-labile enterotoxins is linked to their ADP-ribosyltransferase activity", Eur. J. Immunol. 1992, 22:2277-2281.

Hornquist, E. et al., "Cholera toxin adjuvant greatly promotes antigen priming of T cells", Eur. J. Immunol. 1993, 23:2136-2143.

Tsuji, T. et al., "Immunomodulatory effects of a plasmid expressing B7-2 on human immunodeficiency virus-1-specific cell-mediated immunity induced by a plasmid encoding the viral antigen", Eur. J. Immunol. 1997, 27:782-787.

Vadolas, J. et al., "Intranasal Immunization with liposomes induces strong mucosal immune responses in mice", Eur. J. Immunol. 1995, 25: 969-975.

Maloy, K.J. et al., "Induction of Th1 and Th2 CD4+ T cell responses by oral or parenteral immunization with ISCOMS", Eur. J. Immunol. 1995. 25: 2835-2841.

Sjolander, A. et al., "Iscoms Containing Purified Quillaja Saponins Upregulate both Th1-like and Th2-like Immune Responses", Cellular Immunology 177, 69-76 (1997) Article No. CI971088.

Kukowska-Latallo, J.F. et al., "Efficient transfer of genetic material into mammalian cells using Starburst polyamidoamine dendrimers", Proc. Natl. Sci. USA, vol. 93, pp. 4897-4902, May 1996, Genetics.

Schirmbeck, R. et al., "Immunization with Soluble Hepatitis B Virus Surface Protein Elicits Murine H-2 Class I-Restricted CD8+ Cytotoxic T Lymphocyte Responses In Vivo", Journal of Immunology, 1994, 152: 1110.

Bird, A.P. et al., "CpG islands as gene markers in the vertebrate nucleus", TIG—Dec. 1987, vol. 3, No. 12 pp. 342-347.

Davis, H.L. et al., "CpG DNA Is a Potent Enhancer of Specific Immunity in Mice Immunized with Recombinant Hepatitis B Surface Antigen", The Journal of Immunology, 1998, 160: 870-876.

Mestecky, J. et al., "Prospects for Human Mucosal Vaccines", 1992, 13-23.

McGhee, J., et al., "The mucosal immune system: from fundamental concepts to vaccine development", Vaccine, 1992, 10:2:75-88.

Gallichan, W., et al., Specific secretory immune responses in the female genital tract following intrannasal immunization with a recombinant adenovirus expressing glycoprotein B of herpes simplex virus, 1995, 13:16:1589-1595.

Agrawal, S. et al., "Pharmacokinetics of Antisense Oligonucleotides", *Clin. Pharmacokinet.*, 1995, pp. 7-16, vol. 28, No. 1.

Agrawal, S., "Antisense oligonucleotides: towards clinical trials", *TIBTECH*, Oct. 1996, pp. 376-387, vol. 14, Elsevier Science.

Agrawal, S. et al., "Toxicologic Effects of an Oligodeoxynucleotide Phosphorothioate and Its Analogs Following Intravenous Administration in Rats", *Antisense & Nucleic Acid Drug Development*, 1997, pp. 575-584, vol. 7, Mary Ann Liebert, Inc.

Allison, A.C. et al., "The Development of an Adjuvant Formulation that Elicits Cell-Mediated and Humoral Immune Responses to Virus Subunit and Other Antigens", *Immunopharmacology of Infectious Diseases: Vaccine Adjuvants and Modulators of Non-Specific Resistance*, 1987, pp. 191-201, Alan R. Liss, Inc.

Anderson, G.P. et al., "$T_H2$ and '$T_H2$-like' cells in allergy and asthma: pharmacological perspectives", *TIPS*, 1994, pp. 324-332, vol. 15.

(56) References Cited

OTHER PUBLICATIONS

Anfossi, G. et al., "An oligomer complementary to *c-myb*-encoded mRNA inhibits proliferation of human myeloid leukemia cell lines", *Proc. Natl. Acad. Sci. USA*, May 1989, pp. 3379-3383, vol. 86.

Ballas, Z.K. et al., "A patient with simultaneous absence of "classical" natural killer cells (CD3−, CD16+. and NKH1+) and expansion of CD3+, CD4−, CD8−, NKH1+ subset", *J. Allergy Clin. Immunol.*, Feb. 1990, pp. 453-459, vol. 85, No. 2.

Bernhard, M.I. et al., "Monocyte-Macrophage Mediated Antibody Dependent and Independent Cell Mediated Cytotoxicity in Normals and Cancer Patients", *Proc. of AACR and ASCO*, p. C-159, vol. 22(372).

Cattaneo, R. et al., "Signals regulating hepatitis B surface antigen transcription", *Nature*, Sep. 22, 1983, pp. 336-338, vol. 305, Macmillan Journals Ltd.

Constant, P. et al., "Stimulation of Human γδ T Cells by Nonpeptidic Mycobacterial Ligands", *Science*, Apr. 8, 1994, pp. 267-270, vol. 264.

Cossum, P.A. et al., "Pharmacokinetics of a $^{14}$C-Labeled Phosphorothioate Oligonucleotide, ISIS 2105, after Intradermal Administration to Rats", *Journal of Pharmacology and Experimental Therapeutics*, 1994, pp. 89-94, vol. 269, No. 1, USA.

Davis, H.L. et al., "DNA vaccine for hepatitis B: Evidence for immunogenicity in chimpanzees and comparison with other vaccines", *Proc. Natl. Acad. Sci. USA*, Jul. 1996, pp. 7213-7218, vol. 93.

Davis, H.L., "Plasmid DNA expression systems for the purpose of immunization", *Curr. Opin. Biotechnol.*, Oct. 1997, pp. 635-646, vol. 8, No. 5.

Dematos, T. et al., "Pulsing of Dendritic Cells With Cell Lysates From Either B16 Melanoma or MCA-106 Fibrosarcoma Yields Equally Effective Vaccines Against B16 Tumors in Mice", *Journal of Surgical Oncology*, 1998, pp. 79-91, vol. 68, Wiley-Liss, Inc.

Dignam, J.D. et al., "Accurate transcription initiation by RNA polymerase II in a soluble extract from isolated mammalian nuclei", *Nucleic Acids Research*, Nov. 5, 1983, pp. 1475-1489, vol. 11, IRL Press Limited, Oxford, England.

Engleman, E.G., "Dendritic cells: Potential role in cancer therapy", *Cytotechnology*, 1997, pp. 1-8, vol. 25, Kluwer Academic Publishers, Netherlands.

Etchart, N. et al., "Class 1-restricted CTL induction by mucosal immunization with naked DNA encoding measles virus haemagglutinin", *Journal of General Virology*, 1997, pp. 1577-1580, vol. 78, No. 7.

Fields, R.C. et al., "Murine dendritic cells pulsed with whole tumor lysates mediate potent antitumor immune responses in vitro and in vivo", *Proc. Natl. Acad. Sci. USA*, Aug. 1998, pp. 9482-9487, vol. 95, The National Academy of Sciences.

Fujieda, S. et al., "Effect of OK-432 on Cytotoxic Activity in Cancer Patients without Tumor Burden", *Anticancer Research*, 1992, pp. 1941-1946, vol. 12.

Fuller, D.H. et al., "Induction of immunodeficiency virus-specific immune responses in rhesus monkeys following gene gun-mediated DNA vaccination", *J. Med. Primatol.*, 1996, pp. 236-241, vol. 25, USA.

Fynan, E.F. et al., "DNA vaccines: Protective immunizations by parenteral, mucosal, and gene-gun inoculations", *Proc. Natl. Acad. Sci. USA*, Dec. 1993, pp. 11478-11482, vol. 90.

Garrigan, K. et al., "Functional Comparison of Spleen Dendritic Cells and Dendritic Cells Cultured In Vitro From Bone Marrow Precursors", *Blood*, Nov. 1, 1996, pp. 3508-3512, vol. 88, No. 9.

Gately, M.K., "Interleukin-12: A Recently Discovered Cytokine with Potential for Enhancing Cell-Mediated Immune Responses to Tumors", *Cancer Investigation*, 1993, pp. 500-506, vol. 11, No. 4, Marcel Dekker, Inc.

Gluckman, J.C. et al., "In vitro generation of human dendritic cells and cell therapy", *Cytokines, Cellular and Molecular Therapy*, 1997, pp. 187-196, vol. 3, Martin Dunitz Ltd.

Gramzinski, R.A. et al., "Immune Response to a Hepatitis B DNA Vaccine in *Aotus* Monkeys: A Comparison of Vaccine Formulation, Route, and Method of Administration", *Molecular Medicine*, Feb. 1998, pp. 109-118, vol. 4, No. 2.

Grouard, G. et al., "The Enigmatic Plasmacytoid T Cells Develop into Dendritic Cells with Interleukin (IL)-3 and CD40-Ligand", *J. Exp. Med.*, Mar. 17, 1997, pp. 1101-1111, vol. 185, No. 6, The Rockefeller University Press.

Guery, J.C. et al., "Dendritic Cells are the Most Efficient in Presenting Endogenous Naturally Processed Self-Epitopes to Class II-Restricted T Cells", *The Journal of Immunology*, 1995, pp. 536-544, vol. 152, No. 2.

Hamblin, T.J., "Ex vivo Activation and Retransfusion of White Blood Cells", *Curr. Stud. Hematol. Blood Transf.*, 1990, pp. 249-266, vol. 57.

Hartmann, G. et al., "CpG DNA: A potent signal for growth, activation, and maturation of human dendritic cells", *Proc. Natl. Acad. Sci. USA*, Aug. 1999, pp. 9305-9310, vol. 96.

Hsu, F.J. et al., "Vaccination of patients with B-cell lymphoma using autologous antigen-pulsed dendritic cells", *Nature Medicine*, Jan. 1996, pp. 52-58, vol. 2, No. 1.

Jakob, T. et al., "Activation of Cutaneous Dendritic Cells by CpG-Containing Oligodeoxynucleotides: A Role for Dendritic Cells in the Augmentation of Th1 Responses by Immunostimualtory DNA", *The Journal of Immunology*, 1998, pp. 3042-3049, vol. 161, No. 6.

Jakob, T. et al., "Bacterial DNA and CpG-Containing Oligodeoxynucleotides Activate Curaneous Dendritic Cells and Induce IL-12 Production: Implications for the Augmentation of Th1 Responses", *Int. Arch. Allergy Immunol.*, 1999, pp. 457-461, vol. 118.

Kataoka, T. et al., "Immunotherapeutic Potential in Guinea-Pig Tumor Model of Deoxyribonucleic Acid from *Mycobacterium bovis* BCG Complexed with Poly-L-Lysine and Carboxy-Methylcellulose", *Jpn. J. Med. Sci. Biol.*, 1990, pp. 171-182, vol. 43.

Kou, K. et al., "Analysis and regulation of interferon-gamma production by peripheral blood lymphocytes from patients with bronchial asthma", *Arerugi*, Mar. 1994, Abstract, pp. 482-491, vol. 43, No. 3.

Kolitz, J.E. et al., "The Immunotherapy of Human Cancer with Interleukin 2: Present Status and Future Directions", *Cancer Investigation*, 1991, pp. 529-542, vol. 9, No. 5, Marcel Dekker, Inc.

Kuramoto, E. et al., "In Situ Infiltration of Natural Killer-Like Cells Induced by Intradermal Injection of the Nucleic Acid Fraction from BCG", *Microbiol. Immunol.*, 1989, pp. 929-940, vol. 33, No. 11.

Kuramoto, E. et al., "Changes of Host Cell Infiltration into Meth A Fibrosarcoma Tumor During the Course of Regression Induced by Injections of a BCG Nucleic Acid Fraction", *Int. J Immunopharmac.*, 1992, pp. 773-782, vol. 14, No. 5, Pergamon Press Ltd.

Lacour, J., "Clinical Trials Using Polyadenylic-Polyuridylic Acid as an Adjuvant to Surgery in Treating Different Human Tumors", *Journal of Biological Response Modifiers*, 1985, pp. 538-543, vol. 4, Raven Press, New York.

Lanzavecchia, A., "License to Kill", *Nature*, Jun. 4, 1998, pp. 413-414, vol. 393.

Li, Z. et al., "Desmin sequence elements regulating skeletal muscle-specific expression in transgenic mice", *Development*, 1993, pp. 947-959, vol. 117, The Company of Biologists Limited, Great Britain.

Liang, H. et al., "Activation of Human B Cells by Phosphorothioate Oligodeoxynucleotides", *J. Clin. Invest.*, Sep. 1996, pp. 1119-1129, vol. 98, No. 5.

Lipford, G.B. et al., "Immunostimulatory DNA: sequence-dependent production of potentially harmful or useful cytokines", *Eur. J. Immunol.*, 1997, pp. 3420-3426, vol. 27, Wiley-VCH Verleg GmbH.

Ludewig, B. et al., "Dendritic Cells Efficiently Induce Protective Antiviral Immunity", *Journal of Virology*, May 1998, pp. 3812-3818, vol. 72, No. 5.

Morahan, P.S. et al., "Comparative Analysis of Modulators of Non-specific Resistance Against Microbial Infections", *Immunopharmacology of Infection Diseases: Vaccine Adjuvants and Modulators of Non-Specific Resistance*, 1987, pp. 313-324, Alan R. Liss, Inc.

(56) References Cited

OTHER PUBLICATIONS

Nair, S.K. et al., "Regression of Tumors in Mice Vaccinated with Professional Antigen-Presenting Cells Pulsed with Tumor Extracts", *Int. J. Cancer*, 1997, pp. 706-715, vol. 70, Wiley-Liss, Inc.

Nestle, F.O. et al., "Vaccination of melanoma patients with peptide- or tumor lysate-pulsed dendritic cells", *Nature Medicine*, Mar. 1998, pp. 328-332, vol. 4, No. 3.

O'Doherty, U. et al., "Dendritic Cells Freshly Isolated from Human Blood Express CD4 and Mature into Typical Immunostimulatory Dendritic Cells after Culture in Monocyte-conditioned Medium", *J. Exp. Med.*, Sep. 1993, pp. 1067-1078, vol. 178, The Rockefeller University Press.

Okada, H. et al., "Bone Marrow-Derived Dendritic Cells Pulsed with a Tumor-Specific Peptide Elicit Effective Anti-Tumor Immunity Against Intracranial Neoplasms", *Int. J. Cancer*, 1998, pp. 196-201, vol. 78, Wiley-Liss, Inc.

Peterson, M.G. et al., "Transcription Factors: A New Frontier in Pharmaceutical Development?", *Biochemical Pharmacology*, 1994, pp. 127-128, vol. 47, No. 1, Elsevier Science Ltd., Great Britain.

Pottratz, S.T. et al., "17β-Estrodiol Inhibits Expression of Human Interleukin-6 Promoter-Reporter Constructs by a Receptor-dependent Mechanism", *The Journal of Clinical Investigation, Inc.*, Mar. 1994, pp. 944-950, vol. 93.

Prince, A.M. et al., "Successful nucleic acid based immunization of newborn chimpanzees against hepatitis B virus", *Vaccine*, 1997, pp. 916-919, vol. 15, No. 8.

Reisfeld, R.A., "Monoclonal Antibodies in Cancer Immunotherapy", *Clinics in Laboratory Medicine*, Jun. 1992, pp. 201-216, vol. 12, No. 2.

Ridge, J.P. et al., "A conditioned dendritic cell can be a temporal bridge between a $CD4^+$ T-helper and a T-killer cell", *Nature*, Jun. 4, 1988, pp. 474-478, vol. 393.

Robinson, S.P. et al., "Developmental Aspects of Dendritic Cells In Vitro and In Vivo", *Leukemia and Lymphoma*, 1997, pp. 477-490, vol. 29, Overseas Publishers Association Amsterdam B.V.

Robinson, H.L., "Nucleic acid vaccines: an overview", *Vaccine*, 1997, pp. 785-787, vol. 15, No. 8, Elsevier Science Ltd., Great Britain.

Rojanasakul, Y., "Antisense oligonucleotide therapeutics: drug delivery and targeting", *Advanced Drug Delivery Reviews*, 1996, pp. 115-131, vol. 18, Elsevier Science B.V.

Romani, N. et al., "Generation of mature dendritic cells from human blood. An improved method with special regard to clinical applicability", *Journal of Immunological Methods*, 1996, pp. 137-151, vol. 196, Elsevier Science B.V.

Rosenberg, S.A., "Immunotherapy of Cancer by Systemic Administration of Lymphoid Cells Plus Interleukin-2", *Journal of Biological Response Modifiers*, 1984, pp. 501-511, vol. 3, Raven Press, New York.

Rosenberg, S.A. et al., "Observations on the Systemic Administration of Autologous Lymphokine-Activated Killer Cells and Recombinant Interleukin-2 to Patients with Metastatic Cancer", *N. E. J. of Med.*, 1985, pp. 1485-1492, vol. 113, No. 23.

Rosenberg, S.A. et al., "Immunologic and therapeutic evaluation of a synthetic peptide vaccine for the treatment of patients with metastatic melanoma", *Nature Medicine*, Mar. 1998, pp. 321-327, vol. 4, No. 3.

Sands, H. et al., "Biodistribution and Metabolism of Internally $^3$H-Labeled Oligonucleotides. I. Comparison of a Phosphodiester and a Phosphorothioate", *Molecular Pharmacology*, 1994, pp. 932-943, vol. 45.

Sarmiento, U.M. et al., "In Vivo Toxicological Effect of *rel* A Antisense Phosphorothioates in CD-1 Mice", *Antisense Research and Development*, 1994, pp. 99-107, vol. 4, Mary Ann Liebert, Inc.

Schoenberger S.P. et al., "T-cell help for cytotoxic T lymphocytes is mediated by CD40-CD40 interactions", *Nature*, Jun. 4, 1988, pp. 480-483, vol. 393.

Sedegah, M. et al., "Protection against malaria by immunization with plasmid DNA encoding circumsporozoite protein", *Proc. Natl. Acad. Sci. USA*, Oct. 1994, pp. 9866-9870, vol. 91.

Shimada, S. et al., "Antitumor Activity of the DNA Fraction from *Mycobacterium bovis* BCG. II. Effects on Various Syngeneic Mouse Tumors", *JNCI*, Mar. 1985, pp. 681-688, vol. 74, No. 3.

Shimada, S. et al., "In vivo Augmentation of Natural Killer Cell Activity with a Deoxyribonucleic Acid Fraction of BCG", *Jpn. J. Cancer Res.*, Aug. 1986, pp. 808-816, vol. 77.

Sparwasser, T. et al., "Bacterial DNA and immunostimulatory CpG oligonucleotides trigger maturation and activation of murine dendritic cells", *Eur. J. Immunol.*, 1998, pp. 2045-2054, vol. 28, Wiley-VCH Verlag GmbH.

Stein, C.A. et al., "Antisense Oligonucleotides as Therapeutic Agents—Is the Bullet Really Magical?", *Science*, Aug. 20, 1993, pp. 1004-1012, vol. 261.

Steinman, R.M., "Dendritic cells and immune-based therapies", *Experimental Hematology*, 1996, pp. 859-862, vol. 24.

Stevenson, H.C. et al., "The Treatment of Cancer with Activated Cytotoxic Leukocyte Subsets", *Artif. Organs*, 1988, pp. 128-136, vol. 12, No. 2.

Threadgill, D.S. et al., "Mitogenic synthetic polynucleotides suppress the antibody response to a bacterial polysaccharide", *Vaccine*, 1998, pp. 76-82, vol. 16, No. 1, Elsevier Science Ltd., Great Britain.

Tjoa, B.A. et al., "Evaluation of Phase I/II Clinical Trails in Prostate Cancer With Dendritic Cells and PSMA Peptides", *The Prostate*, 1998, pp. 39-44, vol. 36, Wiley-Liss, Inc.

Topalian, S.L. et al., "Expansion of human tumor infiltrating lymphocytes for use in immunotherapy trials", *Journal of Immunological Methods*, 1987, pp. 127-141, vol. 102.

Torpey III, D. et al., "Effects of Adoptive Immunotherapy with Autologous $CD8^+$T Lymphocytes on Immunologic Parameters: Lymphocyte Subsets and Cytotoxic Activity", *Clinical Immunology and Immunopathology*, Sep. 1993, pp. 263-272, vol. 68, No. 3, Academic Press, Inc.

Valenzuela, P. et al., "Synthesis and assembly of hepatitis B virus surface antigen particles in yeast", *Nature*, Jul. 22, 1982, pp. 347-350, vol. 298, Macmillan Journals Ltd.

Van Schooten, W.C.A. et al., "Biological properties of dendritic cells: implications to their use in the treatment of cancer", *Molecular Medicine Today*, Jun. 1997, pp. 254-260, Elsevier Science Ltd.

Vogels, M.T.E. et al., "Use of Immune Modulators in Nonspecific Therapy of Bacterial Infections", *Antimicrobial Agents and Chemotherapy*, Jan. 1992, pp. 1-5, vol. 36, No. 1.

Waag, D.M. et al., "Injection of Inactivated Phase I *Coxiella burnetti* Increases Non-specific Resistance to Infection and Stimulates Lymphokine Production in Mice", *Annals New York Academy of Sciences*, 1990, pp. 203-214, vol. 590.

Walker, C. et al., "Activated T Cells and Cytokines in Bronchoalveolar Lavages from Patients with Various Lung Diseases Associated with Eosinophilia", *Am. J. Respir. Crit. Care Med.*, 1994, pp. 1038-1048, vol. 150.

Walker, P.S. et al., "Immunostimulatory oligodeoxynucleotides promote protective immunity and provide systemic therapy for leishmaniasis via IL-12- and IFN-γ-dependent mechanisms", *Proc. Natl. Acad. Sci. USA*, Jun. 1999, pp. 6970-6975, vol. 96.

Wang, B. et al, "Gene inoculation generates immune responses against human immunodeficiency virus type I", *Proc. Natl. Acad. Sci. USA*, May 1993, pp. 4156-4160, vol. 90.

Weiner, G.J. et al., "Immunostimulatory oligodeoxynucleotides containing the CpG motif are effective as immune adjuvants in tumor antigen immunization", *Proc. Natl. Acad. Sci. USA*, Sep. 1997, pp. 10833-10837, vol. 94.

Xiang, Z.Q. et al., "The effect of interferon-γ on genetic immunization", *Vaccine*, 1997, pp. 896-898, vol. 15, No. 8, Elsevier Science Ltd., Great Britain.

Yang, S. et al., "Immunotherapeutic Potential of Tumor Antigen-Pulsed and Unpulsed Dendritic Cells Generated from Murine Bone Marrow", *Cellular Immunology*, 1997, pp. 84-95, vol. 179, Academic Press.

Zelphati, O. et al., "Inhibition of HIV-1 Replication in Cultured Cells with Antisense Oligonucleotides Encapsulated in Immunoliposomes", *Antisense Research and Development*, 1993, pp. 323-338, vol. 3, Mary Ann Liebert, Inc.

Davis, et al., "CpG DNA overcomes hyporesponsiveness to hepatitis B vaccine in orangutans", *Vaccine* 18:1920-1924 (2000).

(56) References Cited

OTHER PUBLICATIONS

Davis, H.L., "Plasmid DNA expression systems for the purpose of immunization", *Current Biology*, 16:42:36 (1997).
Doe, et al., "Induction of cytotoxic T lymphocytes by intramuscular immunization with plasmic DNA is facilitated by bone marrow-derived cells", *Proc. Natl. Acad. Sci. USA*, 93:8578-8583 (1996).
Jones, et al., "Synthetic oligodeoxynucleotides containing CpG motifs enhance immunogenicity of a peptide malaria vaccine in Aotus monkeys", *Vaccine*, 3065-3071 (1999).
Kataoka, et al., "Antitumor activity of synthetic oligonucleotides with sequences from cDNA encoding proteins of *Mycobacterium bovis* BCG", Jpn. J. Cancer Res., 83:244-247 (1992).
Klinman, et al., "Immune recognition of foreign DNA: a cure for bioterrorism", *Immunity*, 11:123-129 (1999).
Threadgill, et al., "Mitogenic synthetic polynucleotides suppress the antibody response to a bacterial polysaccharide", *Vaccine* 16(1):76-82 (1998).
McCluskie et al., "Cutting Edge: CpG DNA is a Potent Enhancer of Systemic and Mucosal Immune Responses Against Hepatitis B Surface Antigen with Intranasal Administration to Mice", *J. Immunol.*, 161:4463,4466, 1998.
Choi AH et al., "The level of protection against rotavirus shedding in mice following immunization with a chimeric VP6 protein is dependant on the route and the coadministered adjuvant", *Vaccine.* Mar 15, 2002;20(13-14): 1733-40.
Davis, HL, "Use of CpG DNA for enhancing specific immune responses", *Curr Top Microbiol Immunol.* 2000; 247: 171-83.
Dumais, N. et al., "Mucosal immunization with inactivated human immunodeficiency virus plus CpG oligodeoxynucleoties induce genital immune responses and protection against intravaginal challenge", J. Infect. Dis. Oct. 15, 2002; 186(8):I098-105. Epub Sep. 2002.
Gallichan, W. Scott et al., "Intranasal Immunization with CpG Oligodeoxynucleotides as an Adjuvant Dramatically Increases IgA and Protection Against Herpes Simplex Virus-2 in the Genital Tract", *The Journal of Immunology*, 2001, 166: 3451-3457.
Hartmann, G et al., "Delineation of a CpG Phosphorothiaote Oligodeoxynucleotide for Activating Primate Immune Responses In Vitro and In Vivo", *The Journal of Immunology*, 2000, 164: 1617-1624.
Kovarik, J et al., "CpG Oligodeoxynucleotides Can Circumvent the Th2 Polarization of Neonatal Responses to Vaccines But May Fail to Fully Redirect Th2 Responses Established by Neonatal Priming", *The Journal of Immunology*, 1999, 162: 1611-1617.
Kovarik, J. et al., "Adjuvant effect of CpG oligodeoxynucleotides on responses against T-independent type 2 antigens", *Immunology.* Jan. 2001; 102(1): 67-76.
Krieg, AM et al., "Bacterial DNA or oligonucleotides containing CpG motifs protect mice from lethal L. monocytogenes challenge", Abstract from 1996 meeting on *Molecular Approaches to the Control of Infectious Diseases*, Cold Spring Harbor Laboratory, Sep. 9-13, 1996. p. 116.
Krieg, AM, "CpG oligoneucleotides as immune adjuvants", *Ernst Schering Res. Found Workshop*, 2000; (30): 105-18.
Krieg, AM, "Immune Effects and mechanisms of action of CpG motifs", *Vaccine.* Nov. 8, 2001; 19(6): 618-22.
Krieg, Am et al., "Enhancing vaccines with immune stimulatory CpG DNA", *Curr Opin Mol Ther*. Feb. 2001; 3(I):15-24.
Liu, Hsin-Ming et al., "Immunostimulatory CpG Oligodeoxynucleotides Enhance the Immune Responses to Vaccine Strategies Involving Granulocyte-Macrophage Colony-Stimulating Factor", *Blood*, vol. 92, No. 10 Nov. 15, 1998: pp. 3730-3736.
Malanchere-Bres, E et al., "CpG Oligodeoxynucleotides with Hepatitis B Surface Antigen (HBsAg) for Vaccination in HBsAg-Transgenic Mice", *Journal of Virology*, Jul. 2001, p. 6482-6491.
Brazolot Millan, Cynthia L. et al., "CpG DNA can induce strong Thl humoral and cell-mediated immune responses against hepatitis B surface antigen in young mice", *Proc. Natl. Acad. Sci. USA*, vol. 95, pp. 15553-15558, Dec. 1998 Immunology.

McCluskie, M.J. et al., "Muscol immunization with DNA vaccines", *Microbes Infect.* Jul. 1999; 1(9): 685-98.
McCluskie, MJ et al., "CpG DNA as mucosal adjuvant", *Vaccine*. Sep. 1999; 18(3-4): 231-7.
McCluskie, MJ et al., "The role of CpG in DNA vaccines", *Springer Semin Immunopathol*. 2000; 22(1-2): 125-32.
McCluskie, MJ et al., "CpG DNA is an effective oral adjuvant to protein antigens in mice", *Vaccine*. Nov. 22, 2000; 19(7-8): 950-7.
McCluskie, MJ et al., "Intranasal immunization of mice with CpG DNA induces strong systematic and mucosal responses that are influenced by other mucosal adjuvants and antigen distribution", *Mol Med*. Oct. 2000; 6(10): 867-77.
McCluskie, MJ et al., "Oral, intrarectal and intranasal immunizations using CpG and non-CpG oligodeoxynucleotides as adjuvants", *Vaccine* 19 (2001) 413-422.
McCluskie, MJ et al., "The potential of CpG oligodeoxynucleotides as muscol adjuvants", *Crit Rev Immunol*. 2001; 21(1-3): 103-20.
McCluskie, MJ et al., "The use of CpG DNA as mucosal vaccine adjuvant", *Curr Opin Investig Drugs*. Jan. 2001; 2(1): 35-9.
McCluskie, MJ et al., "The potential of oligodeoxynucleotides as mucosal and parenteral adjuvants", *Vaccine*. Mar. 21, 2001; 19(17-19):2657-60.
McCluskie, MJ et al., "Mucosal immunization of mice using CpG DNA and/or mutants of the heat-labile enterotoxin of *Escherichia coli* as adjuvants", *Vaccine*. Jun. 14, 2001; 19(27): 3759-68.
McCluskie, MJ et al., "Parenteral and mucosall prime-boost immunization strategies in mice with hepatitis B surface antigen and CpG DNA", *FEMS Immunol Med Microbiol*. Feb. 18, 2002; 32(3): 179-85.
Pal, S. et al, "Immunization with the *Chlamydia trachomatis* mouse pneumonitis major outer membrane protein by use of CpG oligodeoxynucleotides as an adjuvant induces a protective immune response against an intranasal chlaymdial challenge", *Infect Immun.* Sep. 2002; 70(9): 4812-7.
Payette PJ et al., "History of vaccines and positioning of current trends", *Curr Drug Targets Infect Disord*. Nov. 2001; 1(3): 241-7.
Sajic D et al., "Parameters of CpG oligodeoxynucleotide-induced protection against intravaginal HSV-2 challenge", *J Med Virol*. Dec. 2003; 71(4):561-568.
Weeratna, RD et al., "CpG ODN allows lower doses of antigen against hepatitis B surface antigen in BALB/c mice", *Immunol Cell Biol*. Feb. 2003; 81(1): 59-62.
Weeratna, RD et al., "CpG ODN can redirect the Th bias of established Th2 immune responses in adult and young mice",*FEMS Immunol Med Microbiol* Dec. 2001; 32(1): 65-71.
Weeratna, RD., "Priming of immune responses to hepatitis B surface antigen in young mice immunized in the presence of maternally derived antibodies", *FEMS Immunol Med Microbiol*. Apr. 2001; 30(3): 241-7.
Weeratna, RD, "CpG DNA induces stronger immune responses with less toxicity than other adjuvants", *Vaccine*. Mar. 6, 2000; 18(17): 1755-62.
Adya N et al., Expansion of CREB's DNA recognition specificity by Tax results from interaction with Ala-Ala-Arg at positions 282-284 near the conserved DNA-binding domain of CREB. *Proc Natl Acad Sci USA* 91(12):5642-6, Jun. 7, 1994.
Angier, N., Microbe DNA Seen as Alien by Immune System, *New York Times*, Apr. 11, 1995.
Azad RF et al., Antiviral Activity of a Phosphorothioate Oligonucleotide Complementary to RNA of the Human Cytomegalovirus Major Immediate-Early Region. *Antimicrobial Agents and Chemotherapy*, 37:1945-1954 Sep. 1993.
Azuma, Biochemical and Immunological Studies on Cellular Components of Tubercle Bacilli, *Kekkaku*, vol. 69, 9:45-55, 1992.
Ballas ZK et al., Induction of NK activity in murine and human cells by CpG motifs in oligodeoxynucleotides and bacterial DNA. *J. Immunol* 157(5):1840-5, 1996.
Bayever, E., Systemic Administration of a Phosphorothioate Oligonucleotide with a Sequence Complementary to p53 for Acute Myelogenous leukemia and Myelodysplastic Syndrome: Initial Results of a Phase I Trial, *Antisense Res. & Dev.* (1993), 3:383-390.

(56) References Cited

OTHER PUBLICATIONS

Bennett RM et al., DNA binding to human leukocytes. Evidence for a receptor-mediated association, internalization, and degradation of DNA. *J Clin Invest* 76(6):2182-90, 1985.
Berg DJ et al., Interleukin-10 is a central regulator of the response to LPS in murine models of endotoxic shock and the Shwartzman reaction but not endotoxin tolerance. *J Clin Invest* 96(5):2339-47, 1995.
Blanchard DK et al., Interferon-gamma induction by lipopolysaccharide: dependence on interleukin 2 and macrophages. *J Immunol* 136(3):963-70, 1986.
Blaxter et al., Genes expressed in *Brugia malayi* infective third stage larvae. *Molecular and Biochemical Parasitology*, 77:77-93.
Boggs RT et al., Characterization and modulation of immune stimulation by modified oligonucleotides. *Antisense Nucleic Acid Drug Dev* 7(5):461-71, Oct. 1997.
Branda RF et al., Amplification of antibody production by phosphorothioate oligodeoxynucleotides. *J. Lab Clin Med* 128(3):329-38, Sep. 1996.
Branda et al., Immune Stimulation by an Antisense Oligomer Complementary to the rev gene of HIV-1. *Biochemical Pharmacology*, vol. 45, 10:2037-2043, 1993.
Chace, J. et al., Regulation of Differentiation in CD5+ and Conventional B Cells, *Clinical Immunology and Immunopathology*, (1993), 68:3:327-332.
Chang YN et al., The palindromic series I repeats in the simian cytomegalovirus major immediate-early promoter behave as both strong basal enhancers and cyclic AMP response elements. *J Virol* 64(1):264-77, Jan. 1990.
Chu RS et al., CpG oligodeoxynucleotides act as adjuvants that switch on T helper 1 (Th 1) immunity. *J Exp Med* 186(10):1623-31, Nov. 17, 1997.
Chow Y et al., Improvement of Hepatitis B Virus DNA Vaccines by Plasmids Coexpressing Hepatitis B Surface Antigen and Interleukin-2, *Journal of Virology*, vol. 71, No. 1, pp. 169-178, Jan. 1997.
Chow Y et al.; Development of Th1 and Th2 Populations and the Nature of Immune Responses to Hepatitis B Virus DNA Vaccines Can Be Modulated by Codelivery of Various Cytokine Genes, *The Journal of Immunology*, 160:1320-1329, 1998.
Corr M et al., Gene Vaccination with Naked Plasmid DNA: Mechanism of CTL Priming, *J. Exp. Med*, vol. 184, 155-1560, Oct. 1996.
Cowdery JS et al., Bacterial DNA induces NK cells to produce IFN-ganuna in vivo and increases the toxicity of lipopolysaccharides. *J Immunol* 156(12):4570-5, Jun. 15, 1996.
Crosby et al., The Early Responses Gene FGFI-C Encodes a Zinc Finger Transcriptional Activator and is a Member of the GCGGGGGCG (GSG) Element-Binding Protein Family. *Mol. Cell. Biol.*, 2:3835-3841, 1991.
Crystal, Transfer of Genes to Humans: Early Lessons and Obstacles to Success. *Science*, vol. 270, pp. 404-410, 1995.
D'Andrea A et al., Interleukin 10 (IL-10) inhibits human lymphocyte interferon gamma-production by suppressing natural killer cell stimulatory factor/IL-12 synthesis in accessory cells. *J Exp Med* 178(3):1041-8, 1993.
Daheshia M et al., Immune induct on and modulation by topical ocular administration of plasmid DNAoding Antigens and cytokines, *Vaccine*, vol. 16, No. 11/12, pp. 1103-1110, 1998.
Daynes RA et al., Induction of Common Mucosal Immunity by Hormonally Immunomodulated Peripheral Immunization, *Infection and Immunity*, vol. 64, No. 4, pp. 1100-1109, Apr. 1996.
Englisch et al., Chemically Modified Oligonucleotides as Probes and Inhibitors, *Angew. Chem. Int. Ed Engl.* 30:613-629, 1991.
Erb KJ et al., Infection of mice with *Mycobacterium bovis*-Bacillus Calmette-Guerin (BCG) suppresses allergen induced airway eosinophilia. *J Exp Med* 187(4):561-9, Feb. 16, 1998.
Etlinjer, Carrier sequence selection—one key to successful vaccines, *Immunology Today*, vol. 13, 2:52-55, 1992.
Fox RI, Mechanism of action of hydroxychloroquine as an antirheumatic drug. *Chemical Abstracts*, 120:15, Abstract No. 182630 (Apr. 29, 1994).

Gordon et al., Safety, Immunogenicity, and Efficacy of a Recombinantly Produced *Plasmodium falciparum* Circumsporozoite Protein-Hepatitis B Surface Antigen Subunit Vaccine, *JID*, 171, pp. 1576-1585, Jun. 1995.
Gura, T., Antisense Has Growing Pains. *Science* (1995), 270:575-576.
Hadden J et al., Immunostimulants. *TIPS*, (1993), 141:169-174.
Hadden J et al., Immunopharmacology, *JAMA*, (1992)268:20:2964-2969.
Halpern MD et al., Bacterial DNA induces murine interferon-gamma production by stimulation of interleukin-12 and tumor necrosis factor-alpha. *Cell Immunol* 167(1):72-8, 1996.
Hatzfeld J., Release of Early Human Hematopoietic Progenitors from Quiescence by Antisense Transforming Growth Factor β1 or Rb Oligonucleotides, *J. Exp. Med.*, (1991) 174:925-929.
Heppner et al., Safety, Immunogenicity, and Efficacy of *Plasmodium falciparum* Repeatless Circumsporozoite Protein Vaccine Encapsulated in Liposomes, *JID*, 174, pp. 361-366, Aug. 1996.
Highfield PE, Sepsis: the More, the Murkier. *Biotechnology*, 12:828, Aug. 12, 1994.
Hoeffler JP et al., Identification of multiple nuclear factors that interact with cyclic adenosine 3',5'-monophosphate response element-binding protein and activating transcription factor-2 by protein-protein interactions. *Mol Endocrinol* 5(2):256-66, Feb. 1991.
Horspool JH et al., Nucleic Acid Vaccine-Induced Immune Responses Require CD28 Costimulation and Are Regulated by CTLA4, *The Journal of Immunology*, 160:2706-2714, 1998.
Iguchi-Ariga SM and Shaffner W, CpG methylation of the cAMP-responsive enhancer/promoter sequence TGACGTCA abolishes specific factor binding as well as transcriptional activation. *Genes Dev* 3(5):612-9, May 1989.
Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43-52.
Ishikawa R et al., IFN induction and associated changes in splenic leukocyte distribution. *J Immunol* 150(9):3713-27, May 1, 1993.
Kim JJ et al., In Vivo Engineering of a Cellular Immune Response by Coadministration of IL-12 Expression Vector With a DNA Immunogen, *The Journal of Immunology*, 158:816-826, 1997.
Kimura Y et al., Binding of Oligoguanylate to Scavenger Receptors Is Required for Oligonucleotides to Augment NK Cell Activity and Induce IFN, *J. Biochem.*, vol. 116, 5:991-994, 1994.
Kline in et al., CpG motif oligonucleotides are effective in prevention of eosinophilic inflammation in a murine model of asthma. *J Invest Med* 44(7):380A, 1996.
Kline JN et al., Immune redirection by CpG oligonucleotides. Conversion of a Th2 response to a Th1 response in a murine model of asthma. *J Invest Med* 45(3):282A, 1997.
Kline in et al., CpG oligonucleotides can reverse as well as prevent Th2-mediated inflammation in a murine model of asthma. *J Invest Med* 45(7):298A, 1997.
Klinman DM et al., Contribution of CpG Motifs to the Immunogenicity of DNA Vaccines, *The Journal of Immunology*, 158:3635-3639, 1997.
Klinman DM et al., CpG motifs present in bacteria DNA rapidly induce lymphocytes to secrete interleukin 6 interleukin 12, and interferon gamma. *Proc Natl Acad Sci USA* 93(7):2879-83, 1996.
Krieg AM, An innate immune defense mechanism based on the recognition of CpG motifs in microbial DNA. *J Lab Clin Med* 128(2):128-33, 1996.
Krieg AM et al., Uptake of oligodeoxyribonucleotides by lymphoid cells is heterogeneous and inducible. *Antisense Res Dev* 1(2):161-71, Summer 1991.
Krieg AM et al., Oligodeoxynucleotide modifications determine the magnitude of B cell stimulation by CpG motifs. *Antisense Nucleic Acid Drug Dev* 6(2):133-9, Summer.1996.
Krieg AM et al., "Modification of antisense phosphodiester oligodeoxynucleotides by a 5' cholesteryl moiety increases cellular association and improves efficacy", *Proc. Natl. Acad Sci.*, (1993), 90:1048-1052.

(56) References Cited

OTHER PUBLICATIONS

Krieg AM et al., "CpG DNA: A Pathogenic Factor in Systemic Lupus Erythematosus?", *Journal of Clinical Immunology*, (1995) 15:6:284-292.
Krieg AM et al, Phosphorothioate Oligodeoxynucleotides: Antisense or Anti-Protein?, *Antisense Research and Development*, (1995), 5:241.
Krieg AM et al., "Leukocyte Stimulation by Oligodeoxynucleotides", *Applied Antisense Oligonucleotide Technology*, (1998), 431-448.
Krieg AM et al., CpG motifs in bacterial DNA trigger direct B-cell activation. *Nature* 374:546-9, 1995.
Krieg AM et al, "The role of CpG dinuleotides in DNA vaccines", Trends in Microbiology, vol. 6, pp. 23-27, Jan. 1998.
Krieg AM el al, A Role for Endogenous Retroviral Sequences in the Regulation of Lymphocyte Activation, the Journal of Immunology, vol. 143, 2448-2451.
Krieg AM et al., Sequence motifs in adenoviral DNA block immune activation by stimulatory CpG motifs, *Proc. Natl. Acad Sci. USA*, vol. 95, pp. 12631-12636, Oct. 1998.
Kuramoto et al., Oligonucleotide Sequences Required for Natural Killer Cell Activation, *Jpn. J. Cancer Res.*, 83:1128-1131, Nov. 1992.
Larsen DL et al., Coadministration of DNA Encoding Interleukin-6 and Hemagglutinin Confers Protection from Influenza Virus Challenge in Mice, *Journal of Virology*, vol. 72, No. 2, pp. 1704-1708, Feb. 1998.
Lee SW et al., Optimal Induction of Hepatitis C Virus Envelope-Specific Immunity by Bicistronic Plasmid DNA Inoculation with the Granulocyte-Macrophage Colony-Stimulating Factor Gene, *Journal of Virology*, vol. 72, No. 10, pp. 8430-8436, Oct. 1998.
Leonard et al., Conformation of Guanine 8-Oxoadenine Base Pairs in the Crystal Structure of d(CGCGAATT(08A)GCG). *Biochemistry*, 31(36):8415-8420, 1992.
Lipford GB et al., Bacterial DNA as immune cell activator, *Trends Microbiol*, 6(12): 496-500, Dec. 1998.
Lowell et al., Proteosomes,-Emulsomes, and Cholera Toxin B Improve Nasal Immunogenicity of Human Immunodeficiency Virus gp160 in Mice: Induction of Serum, Intestinal, Vaginal, and Lung IgA and IgG, *The Journal of Infectious Diseases*, 175:292-301, 1997.
Lu Y et al., Macrophage inflammatory protein-1α (MIP-1α) expression plasmid enhances DNA vaccine-induced immune response against HIV-1, *Clin Exp Immunol* 115:335-341, 1999.
Macfarlane DE and Manzel L, Antagonism of immunostimulatory CpG-oligodeoxynucleotides by quinacrine, chloroquine, and structurally related compounds. *J Immunol* 160(3):1122-31, Feb. 1, 1998.
Mallon et al., Comparison of antibody response by use of synthetic adjuvant system and Freund complete adjuvant in rabbits, *Am J Vet Res*, vol. 52, No. 9, pp. 1503-1506, Sep. 1991.
Mannino RJ et al., Lipid Matrix-Based Vaccines for Mucosal and Systemic Immunization, pp. 363-387.
Mastrangelo et al. *Seminars in Oncology*. vol. 23, 1:4-21, 1996.
Matson S and Krieg AM, Nonspecific suppression of [3H]thymidine incorporation by "control" oligonucleotides. *Antisense Res Dev* 2(4):325-30, Winter 1992.
McIntyre KW et al., A sense phosphorothioate oligonucleotide directed to the initiation codon of transcription factor NF-kappa B p65 causes sequence-specific immune stimulation. *Antisense Res Dev* 3(4):309-22, Winter 1993.
Messina et al., The Influence of DNA Structure on the in vitro Stimulation of Murine Lymphocytes by Natural and Synthetic Polynucleotide Antigens. *Cellular Immunology*, 147:148-157, 1993.
Messina et al., Stimulation of in vitro Murine Lymphocyte Proliferation by Bacterial DNA. *J. Immunol.*, vol. 147, 6:1759-1764, Sep. 15, 1991.
Mojcik, C., et al., "Administration of a Phosphorothioate Oligonucleotide Antisense Murine Endogenous Retroviral MCF env Causes Immune Effect in vivo in a Sequence-Specific Manner", *Clinical Immunology and Immunopathology*,(1993), 67:2:130-136.

Moldoveanu Z et al., CpG DNA, a novel immune enhancer for systemic and mucosal immunization with influenza virus, *Vaccine*, vol. 16, No. 11/12, pp. 1216-1224, 1998.
Mottram et al., A novel CDC2-related protein kinase from leishmania mexicana LnunCRK1 is post-translationally regulated during the life cycle. *J. Biol. Chem.* 268:28, 21044-21052 (Oct. 1993).
Neuzil KM et al., Adjuvants influence the quantitative and qualitative immune response in BALB/c mice immunized with respiratory syncytial virus FG subunit vaccine, *Vaccine*, vol. 15, No. 5, pp. 252-532, 1997.
*New England BIOLABS Biolabs 1988-1989 Catalog*.
Nyce JW and Metzger WJ, DNA antisense therapy for asthma in an animal model. *Nature* 385:721-725, Feb. 20, 1997.
Okada E et al., Intranasal Immunization of a DNA Vaccine with IL-12- and Granulocyte-Macrophage Colony-Stimulating Factor (GM-CSF)-Expressing Plasmids in Liposomes Induces Strong Mucosal and Cell-Mediated Immune Responses Against HIV-1 Antigens, *The Journal of Immunology*, 159:3638-3647, 1997.
Pisetsky et alo., Stimulation of Murine Lymphocyte Proliferation . . . Simplex Virus., *Life Science*, 54:101-107, (1994).
Pisetsky, D., "Stimulation of in vitro proliferation of murine lymphocytes by synthetic oligodeoxynucleotides", *Molecular Biology Repairs*, (1993) 18:217-221.
Pisetsky, The Immunological Properties of DNA, *The Journal of Immunology*, pp. 421-423 (1996).
Pisetsky, Immunological Consequences of Nucleic Acid Therapy, *Antisense Research and Development*, 5:219-225 (1995).
Raz E et al., Preferential induction of a Th1 immune response and inhibition of specific IgE antibody formation by plasmid DNA immunization. *Proc Natl Acad Sci USA* 93(10):5141-5, May 14, 1996.
Ribi E et al., Preparation and Antitumor Activity of Nontoxic Lipid A, *Cancer Immunol Immunother*, 12:91-96, 1982.
Roman M et al., Immunostimulatory DNA sequences function as T helper-1-promoting adjuvants. *Nat Med* 3(8):849-54, Aug. 1997.
Sato et al., Immunostimulatory DNA Sequences Necessary for Effective Intradermal Gene Immunization, *Science*, vol. 273, pp. 352-354, 1996.
Schnell et al., Identification and characterization of a *Saccharomyces cerevisiae* gene (PAR1) conferring resistance to iron chelators. *Eur J. Biochem.*, 200:487-493.
Schultz N et al., Effect of DETOX as an adjuvant for melanoma vaccine, *Vaccine*, vol. 13, No. 5, pp. 503-508, 1995.
Schwartz DA et al., Endotoxin responsiveness and grain dust-induced inflammation in the lower respiratory tract. *Am J Physiol* 267(5 Pt 1):L609-17, 1994.
Schwartz DA et al., The role of endotoxin in grain dust-induced lung disease. *Am J Respir Crit Care Med* 152(2):603-8, 1995.
Schwartz DA et al., CpG motifs in bacterial DNA cause inflammation in the lower respiratory tract. *J Clin Invest* 100(1):68-73, Jul. 1, 1997.
Shirakawa T et al., The inverse association between tuberculin responses and atopic disorder. *Science* 275(5296):77-9, Jan. 1997.
Sin J et al., IL-12 Gene as a DNA Vaccine Adjuvant in a Herpes Mouse Model: IL-12 Enhances Th1-Type CD4+ Cell-Mediated Protective Immunity Against Herpes Simplex Virus-2 Challenge, *The Journal of Immunology*, 162:2912-2921, 1999.
Sin J et al., In Vivo Modulation of Vaccine-Induced Immune Responses toward a Th-1 Phenotype Increases Potency and Vaccine Effectiveness in a Herpes Simplex Virus Type 2 Mouse Model, *Journal of Virology*, vol. 73, No. 1, pp. 501-509, Jan. 1999.
Sparwasser T et al., Macrophages sense pathogens via DNA motifs: induction of tumor necrosis factor-alpha-mediated shock. *Eur J Immunol* 27(7):1671-9, Jul. 1997.
Stein CA et al., Oligonucleotides as inhibitors of gene expression: a review. *Cancer Research*, 48:2659-2668, 1988.
Stull et al., Antigene, Ribozyme, and Aptamer Nucleic Acid Drugs: Progress and Prospects, *Pharmaceutical Res.*, vol. 12, 4:465-483, 1995.
Subramanian et al., Theoretical Considerations on the "Spine of Hydration" in the Minor Groove of d(CGCGAATTCGCG) d(GCGCTTAAGCGC): Monte Carlo Computer Simulation. *Proc. Nat'l. Acad. Sci. USA*, 85:1836-1840, 1988.
Sun S et al., Mitogenicity of DNA from Different Organisms for Murine B Cells, *The Journal of Immunology*, pp. 3119-3125.

(56) References Cited

OTHER PUBLICATIONS

Tanaka T et al., An antisense Oligonucleotide complementary to a sequence in IG2b increases G2b germline transcripts stimulates B cell DNA synthesis and inhibits immunoglobulin secretion. *J. Exp. Med*, 175:597-607, 1992.

Tang D et al., Genetic immunization is a simple method for eliciting an immune response, *Nature*, vol. 356, pp. 152-154, Mar. 12, 1992.

Thoelen et al., Safety and immunogenicity of a hepatitis B vaccine formulated with a novel adjuvant system, *Vaccine*, vol. 16, No. 17, pp. 708-714, 1998.

Thorne PS., Experimental grain dust atmospheres generated by wet and dry aerosolization techniques. *Am. J Ind Med* 25(1):109-12, 1994.

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol. Immunol.*, vol. 36, 1:55-66, 1992.

Tokunaga et al., A Synthetic Single-Stranded DNA, Ply (dG, dC), Induces Interferon α/β and -γ, Augments Natural Killer Activity and Suppresses Tumor Growth. *Jpn. J. Cancer Res.*, 79:682-686, Jun. 1988.

Tomasi M et al., Strong mucosal adjuvanticity of cholera toxin within lipid particles of a new multiple emulsion delivery system for oral immunization, *Eur. J. Immunol.*, 27:2720-2725, 1997.

Tsuji T et al., Enhancement of Cell-Mediated Immunity Against HIV-1 Induced by Coinoculation of Plasmid-Encoded HIV-1 Antigen with Plasmid Expressing IL-12, *Journal of Immunology*, 158:4008-4013, 1997.

Uhlmann et al., Antisense Oligonucleotides: A New Therapeutic Principle. *Chemical Reviews*, 90:543-584, 1990.

Usinger, A comparison of antibody responses to veterinary vaccine antigens potentiated by different adjuvants, *Vaccine*, vol. 15, No. 17/19, pp. 1902-1907, 1997.

Vosika G et al., Phase I Study of Intravenous Mycobacterial Cell Wall Skeleton and Trehalose Cimycolate Attached To Oil Droplets, *Journal of Biological Response Modifiers*, 3:620-626, 1984.

Vosika G et al., Phase I-II Study of Intralesional Immunotherapy with Oil-Attached *Mycobacterium smegmatis* Cell Wall Skeleton and Trehalose Dimycolate, *Cancer Immunol Immunother*, 6, 135-142 (1979).

Wagner RW, Gene inhibition using antisense oligodeoxynucleotides. *Nature*, 372:L333-335, 1994.

Wallace et al., Oligonucleotide probes for the screening of recombinant DNA libraries. *Methods in Enzymology*, 152:432-442(1987).

Weeratna R et al., Reduction of Antigen Expression from DNA Vaccines by Coadministered Oligodeoxynucleotides, *Antisense & Nucleic Drug Development*, 8:351-356, 1998.

Weiss R., Upping the Antisense Ante: Scientists bet on profits from reverse genetics. *Science*, 139:108-109, 1991.

Weiss R., A Plasmid Encoding Murine Granulocyte-Macrophage Colony-Stimulating Factor Increases Protection Conferred by a Malaria DNA Vaccine, *The Journal of Immunology*, vol. 161, pp. 2325-2332, 1998.

Whalen R, DNA Vaccines for Emerging Infection Diseases: What If?, *Emerging Infectious Disease*, vol. 2, 3:168-175, 1996.

Wu Gy et al., Receptor-mediated gene delivery and expression in vivo. *J. Biol. Chem.*, 263:14621-14624, 1988.

Wu-Pong S., Oligonucleotides: Opportunities for Drug Therapy and Research. *Pharmaceutical Technology*, 18:102-114, 1994.

Xin KQ et al., Intranasal administration of human immunodeficiency virus type-1 (HIV-1) DNA vaccine with interleukin-2 expression plasmid enhances cell-mediated immunity against HIV-1, *Immunology*, 94:438-444, 1998.

Yamamoto S et al., DNA from bacteria, but not from vertebrates, induces interferons, activates natural killer cells and inhibits tumor growth. *Microbiol Immunol* 36(9):983-97, 1992.

Yamamoto S et al., In vitro augmentation of natural killer cell activity and production of interferon-alpha/beta and —gamma with deoxyribonucleic acid fraction from *Mycobacterium bovis* BCG. *Jpn J Cancer Res* 79:866-73, Jul. 1988.

Yamamoto S., Mode of Action of Oligonucleotide Fraction Extracted from *Mycobacterium bovis* Bcg, *Kekkaku*, vol. 69, 9:29-32, 1994.

Yamamoto S et al., Unique Palindromic Sequences in Synthetic Oligonucleotides are Required to Induce INF and Augment INF-Mediated Natural Killer Activity. *J. Immunol.*, vol. 148, 12:4072-4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.*, 4:119-123, 1994.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol.*, vol. 38, 10:831-836, 1994.

Yamamoto T et al., Synthetic Oligonucleotides with Certain Palindromes Stimulate Interferon Production of Human Peripheral Blood Lymphocytes in vitro. *Jpn. J. Cancer Res.*, 85:775-779, 1994.

Yi, Ae-Kyung et al., IFN-γ Promotes IL-6 and IgM Secretion in Response to CpG Motifs in Bacterial DNA and Oligonucleotides, *The Journal of Immunology*, pp. 558-564 (1996).

Yi, Ae-Kyung et al., Rapid Immune Activation by CpG Motifs in Bacterial DNA, *The Journal of Immunology*, pp. 5394-5402 (1996).

Zhao Q et al., Stage-specific oligonucleotide uptake in murine bone marrow B-cell precursors. *Blood* 84(11):3660-6, Dec. 1, 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53-66, Spring 1993.

Aderem et al., Toll-like receptors in the induction of the innate immune response. Nature. Aug. 17, 2000;406(6797):782-7.

Askew et al., CpG DNA induces maturation of dendritic cells with distinct effects on nascent and recycling MHC-II antigen-processing mechanisms. J Immunol. Dec. 15, 2000;165(12):6889-95.

Bauer et al., DNA activates human immune cells through a CpG sequence-dependent manner. Immunology. Aug. 1999;97(4):699-705.

Broide et al., DNA-Based immunization for asthma. Int Arch Allergy Immunol. Feb.-Apr. 1999;118(2-4):453-6.

Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.

Calarota et al., Cellular cytotoxic response induced by DNA vaccination in HIV-1-infected patients. Lancet. May 2, 1998;351(9112):1320-5.

Carson et al., Oligonucleotide adjuvants for T helper 1 (Th1)-specific vaccination. J Exp Med. Nov. 17, 1997;186(10):1621-2.

Chace et al., Bacterial DNA-induced NK cell IFN-gamma production is dependent on macrophage secretion of IL-12. Clin Immunol Immunopathol. Aug. 1997;84(2):185-93.

Chelvarajan et al., CpG oligodeoxynucleotides overcome the unresponsiveness of neonatal B cells to stimulation with the thymus-independent stimuli anti-IgM and TNP-Ficoll. Eur J Immunol. Sep. 1999;29(9):2808-18.

Chen et al., Protective immunity induced by oral immunization with a rotavirus DNA vaccine encapsulated in microparticles. J Virol. Jul. 1998;72(7):5757-61.

Dalpke et al., Phosphodiester CpG oligonucleotides as adjuvants: polyguanosine runs enhance cellular uptake and improve immunostimulative activity of phosphodiester CpG oligonucleotides in vitro and in vivo. Immunology. May 2002;106(1):102-12.

Deml et al., Immunostimulatory CpG motifs trigger a T helper-I immune response to human immunodeficiency virus type-1 (HIV-1) gp 160 envelope proteins. Clin Chem Lab Med. Mar. 1999;37(3):199-204.

Elkins et al., Bacterial DNA containing CpG motifs stimulates lymphocyte-dependent protection of mice against lethal infection with intracellular bacteria. J Immunol. Feb. 15, 1999;162(4):2291-8.

Freidag et al., CpG oligodeoxynucleotides and interleukin-12 improve the efficacy of *Mycobacterium bovis* BCG vaccination in mice challenged with *M. tuberculosis*. Infect Immun. May 2000;68(5):2948-53.

(56) References Cited

OTHER PUBLICATIONS

Gouttefangeas et al., Problem solving for tumor immunotherapy. Nat Biotechnol. May 2000;18(5):491-2.
Hartmann et al., CpG DNA and LPS induce distinct patterns of activation in human monocytes. Gene Ther. May 1999;6(5):893-903.
Hartmann et al., Mechanism and function of a newly identified CpQ DNA motif in human primary B cells. J Immunol. Jan. 15, 2000;164(2):944-53.
Hedley et al., Microspheres containing plasmid-encoded antigens elicit cytotoxic T-cell responses. Nat Med. Mar. 1998;4(3):365-8.
Heeg et al., CpG DNA as a Th1 trigger. Int Arch Allergy Immunol. Feb. 2000;121(2):87-97.
Hopkin et al., BioMedNet, Issue 57, Jun. 25, 1999.
Horner et al., Optimized conjugation ratios lead to allergen immunostimulatory oligodeoxynucleotide conjugates with retained immunogenicity and minimal anaphylactogenicity. J Allergy Clin Immunol. Sep. 2002;110(3):413-20.
Horner et al., Mucosal adjuvanticity of immunostimulatory DNA sequences. Springer Semin Immunopathol. 2000;22(1-2):133-46.
Huang et al., Induction and regulation of Th1-inducing cytokines by bacterial DNA, lipopolysaccharide, and heat-inactivated bacteria. Infect Immun. Dec. 1999;67(12):6257-63.
Iho et al., Oligodeoxynucleotides containing palindrome sequences with internal 5'-CpG-3' act directly on human NK and activated T cells to induce IFN-gamma production in vitro. J Immunol. Oct. 1, 1999; 163(7):3642-52.
Ioannou et al., The immunogenicity and protective efficacy of bovine herpesvirus I glycoprotein D plus Emulsigen are increased by formulation with CpQ oligodeoxynucleotides. J Virol. Sep. 2002;76(18):9002-10.
Jiang et al., Enhancing immunogenicity by CpG DNA. Curr Opin Mol Ther. Apr. 2003;5(2):180-5. Abstract.
Jones et al., Poly(DL-lactide-co-glycolide)-encapsulated plasmid DNA elicits systemic and mucosal antibody responses to encoded protein after oral administration. Vaccine. Jun. 1997;15(8):814-7.
Juffermans et al., CpG oligodeoxynucleotides enhance host defense during murine tuberculosis. Infect Immun. Jan. 2002 ;70(1):147-52.
Klinman et al., Therapeutic applications of CpG-containing oligodeoxynucleotides. Antisense Nucleic Acid Drug Dev. Apr. 1998;8(2):181-4.
Klinman et al., Immunotherapeutic applications of CpG-containing oligodeoxynucleotides. Drug News Perspect. Jun. 2000 ;13(5):289-96.
Klinman et al., Activation of the innate immune sytem by CpG oligodeoxynucleotides: immunoprotective activity and safety. Springer Semin Immunopathol. 2000;22(1-2):173-83.
Kranzer et al. CpG-oligodeoxynucleotides enhance T-cell receptor-triggered interferon-gamma production and up-regulation of CD69 via induction of antigen-presenting cell-derived interferon type I and interleukin-12. Immunology. Feb. 2000;99(2):170-8.
Krieg et al., Immune effects and therapeutic applications of CpG motifs in bacterial DNA. Immunopharmacology. Jul. 25, 2000;48(3):303-5.
Krieg et al., American College of Rheumatology 58th National Scientific Meeting. Minneapolis, Minnesota, Oct. 22, 1994. Abstracts. Arthritis Rheum. Sep. 1994;37(9 Suppl).
Krieg et al., CpG motifs in bacterial DNA and their immune effects. Annu Rev Immunol. 2002;20:709-60. Epub Oct. 4, 2001.
Krieg et al., Causing a commotion in the blood: immunotherapy progresses from bacteria to bacterial DNA. Immunol Today. Oct. 2000;21(10):521-6.
Krieg et al., Chapter 8: Immune Stimulation by Oligonucleotides. in Antisense Research and Application. Crooke, editor. 1998; 243-62.
Krieg et al., Mechanisms and applications of immune stimulatory CpG oligodeoxynucleotides. Biochim Biophys Acta. Dec. 10, 1999;1489(1):107-16.
Krieg et al., The CpG motif: Implications for clinical immunology. BioDrugs. Nov. 1, 1998;10(5):341-6.
Krieg, The role of CpG motifs in innate immunity. Curr Opin Immunol. Feb. 2000;12(1):35-43.
Krieg et al., Mechanism of action of CpG DNA. Curr Top Microbiol Immunol. 2000;247:1-21.
Krieg et al., Mechanisms and therapeutic applications of immune stimulatory CpG DNA. Pharmacol Ther. Nov. 1999;84(2):113-20.
Krieg et al., CpG DNA induces sustained IL-12 expression in vivo and resistance to Listeria monocytogenes challenge. J Immunol. Sep. 1, 1998;161(5):2428-34.
Krieg, Lymphocyte activation by CpG dinucleotide motifs in prokaryotic DNA. Trends Microbiol. Feb. 1996;4(2):73-6.
Kringel et al., CpG-oligodeoxynucleotides enhance porcine immunity to Toxoplasma gondii. Vet Parasitol. Aug. 13, 2004;123(1-2):55-66.
Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.
LeClerc et al., The preferential induction of a Th1 immune response by DNA-based immunization is mediated by the immunostimulatory effect of plasmid DNA. Cell Immunol. Aug. 1, 1997;179(2):97-106.
MacGregor et al., First human trial of a DNA-based vaccine for treatment of human immunodeficiency virus type 1 infection: safety and host response. J Infect Dis. Jul. 1998;178(1):92-100.
Martin-Orozco et al., Enhancement of antigen-presenting cell surface molecules involved in cognate interactions by immunostimulatory DNA sequences. Int Immunol. Jul. 1999;11(7):1111-8.
McCluskie et al., Novel strategies using DNA for the induction of mucosal immunity. Crit Rev Immunol. 1999;19(4):303-29.
McCluskie et al., Immunization against hepatitis B virus by mucosal administration of antigen-antibody complexes. Viral Immunol. 1998;11(4):245-52.
McCluskie et al., Route and method of delivery of DNA vaccine influence immune responses in mice and non-human primates. Mol Med. May 1999;5(5):287-300.
Merad et al., Proc Annu Meet Am Assoc Cancer Res. Mar. 2001; 42. Abstract.
Mitchell et al., RNA transfected dendritic cells as cancer vaccines. Curr Opin Mol Ther. Apr. 2000;2(2):176-81.
Moss et al., In vitro immune function after vaccination with an inactivated, gp120-depleted HIV-1 antigen with immunostimulatory oligodeoxynucleotides. Vaccine. Jan. 6, 2000;18(11-12):1081-7.
Peng et al., CpG oligodeoxynucleotide vaccination suppresses IgE induction but may fail to down-regulate ongoing IgE responses in mice. Int Immunol. Jan. 2001;13(1):3-11.
Pink et al., 4th meeting on Novel Adjuvants Currently in/close to Human Clinical Testing World Health Organization—organisation Mondiale de la Sante Fondation Merieux, Annecy, France, Jun. 23-25, 2003. Vaccine. Jun. 2, 2004;22(17-18):2097-102.
Pisetsky et al., Immunological properties of bacterial DNA. Ann NY Acad Sci. Nov. 27, 1995;772:152-63.
Pisetsky, The influence of base sequence on the immunostimulatory properties of DNA. Immunol Res. 1999;19(1):35-46.
Pisetsky et al., Immune activation by bacterial DNA: a new genetic code. Immunity. Oct. 1996;5(4):303-10.
Rankin at al., CpG motif identification for veterinary and laboratory species demonstrates that sequence recognition is highly conserved. Antisense Nucleic Acid Drug Dev. Oct. 2001;11(5):333-40.
Rankin et al., CpG-containing oligodeoxynucleocotidcs augment and switch the immune responses of cattle to bovine herpesvirus-1 glycoprotein D. Vaccine. Jul. 26, 2002;20(23-24):3014-22.
Ray et al., Experimental Biology 2001. Orlando, Florida, USA. Mar. 31-Apr. 4, 2001. Abstracts, part II. FASEB J. Mar. 8, 2001;15(5):A1007.
Rothenfusser et al., Recent advances in immunostimulatory CpG oligonucleotides. Curr Opin Mol Ther. Apr. 2003;5(2):98-106.
Sandler et al., CpG oligonucleotides enhance the tumor antigen-specific immune response of a granulocyte macrophage colony-stimulating factor-based vaccine strategy in neuroblastoma. Cancer Res. Jan. 15, 2003;63(2):394-9.
Schwartz et al., Bacterial DNA or oligonucleotides containing unmethylated CpG motifs can minimize lipopolysaccharide-induced inflammation in the lower respiratory tract through an IL-12-dependent pathway. J Immunol. Jul. 1, 1999;163(1):224-31.

(56) References Cited

OTHER PUBLICATIONS

Sester et al., Phosphorothioate backbone modification modulates macrophage activation by CpG DNA. J Immunol. Oct. 15, 2000;165(8):4165-73.
Singh et al., Advances in vaccine adjuvants. Nat Biotechnol. Nov. 1999;17(11):1075-81.
Sparwasser et al., Bacterial DNA causes septic shock. Nature. Mar. 27, 1997;386(6623):336-7.
Stacey et al. Immunostimulatory DNA as an adjuvant in vaccination against Leishmania major. Infect Immun. Aug. 1999;67(8):3719-26.
Sun et al. Type I interferon-mediated stimulation of T cells by CpG DNA. J Exp Med. Dec. 21, 1998;188(12):2335-42.
Sun et al. Multiple effects of immunostimulatory DNA on T cells and the role of type I interferons. Springer Semin Immunopathol. 2000;22(1-2):77-84.
Tacket et al., Phase 1 safety and immune response studies of a DNA vaccine encoding hepatitis B surface antigen delivered by a gene delivery device. Vaccine. Jul. 16, 1999;17(22):2826-9.
Tighe et al., Conjugation of protein to immunostimulatory DNA results in a rapid, long-lasting and potent induction of cell-mediated and humoral immunity. Eur J Immunol. Jul. 2000;30(7):1939-47.
Tortora et al., Oral antisense that targets protein kinase A cooperates with taxol and inhibits tumor growth, angiogenesis, and growth factor production. Clin Cancer Res. Jun. 2000;6(6):2506-12.
Ugen et al., DNA vaccination with HIV-1 expressing constructs elicits immune responses in humans. Vaccine. Nov. 1998;16(19):1818-21.
Uhlmann et al., Recent advances in the development of immunostimulatory oligonucleotides. Curr Opin Drug Discov Devel. Mar. 2003;6(2):204-17.
Vollmer et al., Highly immunostimulatory CpG-free oligodeoxynudeotides for activation of human leukocytes. Antisense Nucleic Acid Drug Dev. Jun. 2002;12(3):165-75.
Vollmer et al., Characterization of three CpG oligodeoxynucleotide classes with distinct immunostimulatory activities. Eur J Immunol. Jan. 2004;34(I):251-62.
Wagner, Interactions between bacterial CpG-DNA and TLR9 bridge innate and adaptive immunity. Curr Opin Microbiol. Feb. 2002;5(1):62-9.
Wang et al., Synergy between CpG- or non-CpG DNA and specific antigen for B cell activation. Int Immunol. Feb. 15, 2003;15(2):223-31.
Wang et al., Induction of antigen-specific cytotoxic T lymphocytes in humans by a malaria DNA vaccine. Science. Oct. 16, 1998;282(5388):476-80.
Weigel et al., Comparative analysis of murine marrow-derived dendritic cells generated by Flt3L or GM-CSF/IL-4 and matured with immune stimulatory agents on the in vivo induction of antileukemia responses. Blood. Dec. 1, 2002;100(12):4169-76. Epub Aug. 8, 2002.
Wernette et al., CpG oligodeoxynucleotides stimulate canine and feline immune cell proliferation. Vet Immunol Immunopathol. Jan. 15, 2002;84(3-4):223-36.
Wyatt et al. Combinatorially selected guanosine-quartet structure is a potent inhibitor of human.immunodeficiency virus envelope-mediated cell fusion. Proc Natl Acad Sci U S A. Feb. 15, 1994;91(4):1356-60.
Yi et al. Rapid induction of mitogen-activated protein kinases by immune stimulatory CpG DNA. J lmmunol. Nov. 1, 1998;161(9):4493-7.
Yi et al. CpG oligodeoxyribonuckotides rescue mature spleen B cells from spontaneous apoptosis and promote cell cycle entry. J Immunol. Jun. 15, 1998;160(12):5898-906.
Zhao et al., Pattern and kinetics of cytokine production following administration of phosphorothioate oligonucleotides in mice. Antisense Nucleic Acid Drug Dev. Oct. 1997;7(5):495-502.
Arulanandam et al., Modulation of mucosal and systemic immunity by intranasal interleukin 12 delivery. Vaccine. Jan. 21, 1999;17(3):252-60.

Grdic et al., The mucosal adjuvant effects of cholera toxin and immune-stimulating complexes differ in their requirement for IL-12, indicating different pathways of action. Eur J Immunol. Jun. 1999;29(6):1774-84.
Marinaro et al., Use of intranasal IL-12 to target predominantly Th1 responses to nasal and Th2 responses to oral vaccines given with cholera toxin. J Immunol. Jan. 1, 1999;162(1):114-21.
Simmons et al., Impaired resistance and enhanced pathology during infection with a noninvasive, attaching-effacing enteric bacterial pathogen, Citrobacter rodentium, in mice lacking IL-12 or IFN-gamma. J Immunol. Feb. 15, 2002;15 168(4):1804-12.
U.S. Appl. No. 09/167,039, filed Oct. 5, 1998, Raz et al.
Notice of Opposition in EP Application No. 99925754.6 dated May 25, 2007.
Response to Opposition in EP Application No. 99925754.6 dated Jun. 24, 2008.
Press Release, Jan. 2007, "Coley Pharmaceutical Group Updates Hepatitis C Drug Development Strategy".
Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".
Agrawal et al., Chapter 19: Pharmacokinetics and bioavailability of antisense oligonucleotides following oral and colorectal administrations in experimental animals. 1998: 525-43.
Anitescu et al., Interleukin-10 functions in vitro and in vivo to inhibit bacterial DNA-induced secretion of interleukin-12. J Interferon Cytokine Res. Dec. 1997;17(12):781-8.
Bennett, Intracellular delivery of oligonucleotides with cationic liposomes. In: Delivery Strategies for Antisense Oligonucleotide Therapeutics. Akthar, Ed. 1995:223-32.
Branda et al., B-cell proliferation and differentiation in common variable immunodeficiency patients produced by an antisense oligomer to the rev gene of HIV-1. Clin Immunol Immunopathol. May 1996;79(2):115-21.
Brazolot Millan et al., CpG DNA can induce strong Th1 humoral and cell-mediated immune responses against hepatitis B surface antigen in young mice. Proc Natl Acad Sci U S A. Dec. 22, 1998;95(26):15553-8.
Broide et al., Immunostimulatory DNA sequences inhibit IL-5, eosinophilic inflammation, and airway hyperresponsiveness in mice. J Immunol. Dec. 15, 1998;161(12):7054-62.
Carpentier et al., Oligodeoxynucleotides containing CpG motifs can induce rejection of a neuroblastoma in mice. Cancer Res. Nov. 1, 1999;59(21):5429-32.
Cho et al., Immunostimulatory DNA-based vaccines induce cytotoxic lymphocyte activity by a T-helper cell-independent mechanism. Nat Biotechnol. May 2000; 18:509-14.
Chu et al., CpG oligodeoxynucleotides down-regulate macrophage class II MHC antigen processing. J Immunol. Aug. 1, 1999;163(3):1188-94.
Cohen, Selective anti-gene therapy for cancer: principles and prospects. Tohoku J Exp Med. Oct. 1992;168(2):351-9.
Cooper et al., Safety and immunogenicity of CPG 7909 injection as an adjuvant to Fluarix influenza vaccine. Vaccine. Aug. 13, 2004;22(23-24):3136-43.
Cooper et al., CPG 7909 adjuvant improves hepatitis B virus vaccine seroprotection in antiretroviral-treated HIV-infected adults. AIDS. Sep. 23, 2005;19(14):1473-9.
Cossum et al., Disposition of the 14C-labeled phosphorothioate oligonucleotide ISIS 2105 after intravenous administration to rats. J Pharmacol Exp Ther. Dec. 1993;267(3):1181-90.
Cowsert et al., In vitro evaluation of phosphorothioate oligonucleotides targeted to the E2 mRNA of papillomavirus: potential treatment for genital warts. Antimicrob Agents Chemother. Feb. 1993;37(2):171-7.
Crooke et al., Phosphorothioate Oligonucleotides. Therapeut Apps. 1995;ch5:63-84.
Cryz et al., European Commission COST/STD Initiative. Report of the expert panel VII. Vaccine delivery systems. Vaccine. May 1996;14(7):665-90.

(56) References Cited

OTHER PUBLICATIONS

Davila et al., Repeated administration of cytosine-phosphorothiolated guanine-containing oligonucleotides together with peptide/protein immunization results in enhanced CTL responses with anti-tumor activity. J Immunol. Jul. 1, 2000 1;165(1):539-47.
Davis et al., Chapter 18:DNA-based immunization. In Molecular and Cell Biology of Human Gene Therapeutics. Dickson, Ed. 1995; p. 368.
Davis et al., CpG DNA overcomes hyporesponsiveness to hepatitis B vaccine in orangutans. Vaccine. Mar. 17, 2000 17;18(18):1920-4.
Davis et al., Single-agent monoclonal antibody efficacy in bulky non-Hodgkin's lymphoma: Results of a phase II trial of Rituximab. J. Clin. Oncol. 1999;17:1851-7.
Davis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.
Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.
De La Rosa et al., Microbiological quality of pharmaceutical raw materials. Pharm Acta Helv. 1995;70:227-232.
Diwan et al., Biodegradable nanoparticle mediated antigen delivery to human cord blood derived dendritic cells for induction of primary T cell responses. J Drug Target. 2003;11(8-10):495-507. Abstract Only.
Eastcott et al., Oligonucleotide containing CpG motifs enhances immune response to mucosally or systemically administered tetanus toxoid. Vaccine. Feb. 8, 2001;19(13-14):1636-42.
Fields et al., Fields' Virology. 2001;1:1153.
Filion et al., Major limitations in the use of cationic liposomes for DNA delivery. Int J Pharmaceut. 1998; 162:159-70.
Fraley et al., New generation liposomes: The engineering of an efficient vehicle for intracellular delivery of nucleic acids. Trends Biochem Sci. 1981;6:77-80.
Gao et al., Swelling of hydroxypropyl methylcellulose matrix tablets. 2. Mechanistic study of the influence of formulation variables on matrix performance and drug release. J Pharm Sci. 1996;85:732-740.
Geissler et al., Enhancement of cellular and humoral immune responses to hepatitis C virus core protein using DNA-based vaccines augmented with cytokine-expressing plasmids. J Immunol. Feb. 1, 1997;158(3):1231-7.
Gombotz et al., Protein release from alginate matrices. Adv Drug Deliv Rev. 1998;31:267-285.
Gregoriadis et al., Liposomes for drugs and vaccines. Trends Biotechnol. 1985;3:235-41.
Hartmann et al., Spontaneous and cationic lipid-mediated uptake of antisense oligonucleotides in human monocytes and lymphocytes. J Pharmacol Exp Ther. May 1998;285(2):920-8.
Haslett et al., Strong human immunodeficiency virus (HIV)-specific CD4+ T cell responses in a cohort of chronically infected patients are associated with interruptions in anti-HIV chemotherapy. J Infect Dis. Apr. 2000;181(4):1264-72. Epub Apr. 5, 2000.
Havlir et al., Maintenance antiretroviral therapies in HIV infected subjects with undetectable plasma HIV RNA after triple-drug therapy. AIDS Clinical Trials Group Study 343 Team. N Engl J Med. Oct. 29, 1998;339(18):1261-8.
Haynes et al., Particle-mediated nucleic acid immunization. J Biotechnol. Jan. 26, 1996;44(1-3):37-42.
Higaki et al., Mechanisms involved in the inhibition of growth of a human B lymphoma cell line, B104, by anti-MHC class II antibodies. Immunol Cell Biol. Jun. 1994;72(3):205-14.
Hinkula et al., Recognition of prominent viral epitopes induced by immunization with human immunodeficiency virus type 1 regulatory genes. J Virol. Jul. 1997;71(7):5528-39.
Ho, Toward HIV eradication or remission: the tasks ahead. Science. Jun. 19, 1998;280(5371):1866-7.
Hodes, T-Cell-mediated regulation: help and suppression. In Fundamental Immunology, second edition. Paul, Ed. 1989; pp. 587-620.
Holmgren et al., Cholera toxin and cholera B subunit as oral-mucosal adjuvant and antigen vector systems. Vaccine. Sep. 1993;11(12):1179-84.
Horner et al., Immunostimulatory sequence oligodeoxynucleotide: A novel mucosal adjuvant. Clin Immunol. Apr. 2000;95(1 Pt 2):S19-29.
Imami et al., Assessment of type 1 and type 2 cytokines in HIV type 1-infected individuals: impact of highly active antiretroviral therapy. AIDS Res Hum Retroviruses. Nov. 20, 1999;15(17):1499-508.
Jacobson et al., Early viral response and on treatment response to CpG 10101 (ACTILON™), in combination with pegylated interferon and/or ribavirin, in chronic HCV genotype 1 infected patients with prior relapse response. 57th Annual Meeting of American Association for the Study of the Liver Diseases (AASLD). Oct. 30, 2006 Boston, Massachusetts; Presented Abstract #96.
Johnson et al., Non-specific resistance against microbial infections induced by polyribonucleotide complexes. In: Immunopharmacology of infection diseases: Vaccine adjuvants and modulators of non-specific resistance. 1987: 291-301.
Klinman et al., Repeated administration of synthetic oligodeoxynucleotides expressing CpG motifs provides long-term protection against bacterial infection. Infect Immun. Nov. 1999;67(11):5658-63.
Knipe et al., Fields' Virology. 2001;1:1004-16.
Knipe et al., eds., Fields' Virology. 2001;1:1564.
Krieg et al., Direct immunologic activities of CpG DNA and implications for gene therapy. J Gene Med. Jan.-Feb. 1999;1(1):56-63.
Krieg et al., Applications of immune stimulatory CpG DNA for antigen-specific and antigen-nonspecific cancer immunotherapy. Eur J Canc. Oct. 1999 35/Supp14:S10. Abstract #14.
Krieg et al., P-chirality-dependent immune activation by phosphorothioate CpG oligodeoxynucleotides. Oligonucleotides. 2003;13(6):491-9.
Krieg et al., Chapter 17:Immune stimulation by oligonucleotides. In Antisense Drug Tech. 2001;1394:471-515.
Krieg et al., How to exclude immunostimulatory and other nonantisense effects of antisense oligonucleotides. Manual of Antisense. 1999:79-89.
Krieg et al., CpG DNA: a novel immunomodulator. Trends Microbiol. Feb. 1999;7(2):64-5.
Krieg et al., Unmethylated CpG DNA protects mice from lethal listeria monocytogenes challenge. Vaccines. 1997; 97:77-9.
Krieg et al., Infection. In: McGraw Hill Book. 1996:242-3.
Krieg, Therapeutic potential of Toll-like receptor 9 activation. Nat Rev Drug Discov. Jun. 5, 2006;5(6):471-84.
Krieg et al., Induction of systemic TH1-like innate immunity in normal volunteers following subcutaneous but not intravenous administration of CPG 7909, a synthetic B-class CPG oligodeoxynucleotide TLR9 agonist. J Immunother. Nov.-Dec. 2004;27(6):460-71.
Krieg et al., Now I know my CpGs.Trends Microbiol. Jun. 2001;9(6):249-52.
Krieg, Signal transduction induced by immunostimulatory CpG DNA. Springer Semin Immunopathol. 2000;22(1-2):97-105.
Krieg et al., Antiinfective applications of toll-like receptor 9 agonists. Proc Am Thorac Soc. Jul. 2007;4(3):289-94.
Kulkarni et al., Effect of dietary nucleotides on response to bacterial infections. JPEN J Parenter Enteral Nutr. Mar.-Apr. 1986;10(2):169-71.
Kuramoto et al., Oligonucleotide sequences required for natural killer cell activation. Jpn J Cancer Res. Nov. 1992;83(11):1128-31.
Lee et al., Immuno-stimulatory effects of bacterial-derived plasmids depend on the nature of the antigen in intramuscular DNA inoculations. Immunology. Jul. 1998;94(3):285-9.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Letsinger et al., Synthesis and properties of modified oligonucleotides. Nucleic Acids Symp Ser. 1991;(24):75-8.
Litzinger et al., Fate of cationic liposomes and their complex with oligonucleotide in vivo. Biochim Biophys Acta. Jun. 11, 1996;1281(2):139-49.

(56) References Cited

OTHER PUBLICATIONS

Liu et al., Recombinant interleukin-6 protects mice against experimental bacterial infection. Infect Immun. Oct. 1992;60(10):4402-6.
Liu et al., CpG ODN is an effective adjuvant in immunization with tumor antigen. J Invest Med. Sep. 7, 1997;45(7):333A.
Liu et al., Immunization of non-human primates with Dna vaccines. Vaccine. Jun. 15, 1997;8(8):909-12.
Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis. Curr Top Microbiol Immunol. 1988;141:282-9.
MacFarlane et al., Unmethylated CpG-containing oligodeoxynucleotides inhibit apoptosis in WEHI 231 B lymphocytes induced by several agents: evidence for blockade of apoptosis at a distal signalling step. Immunology. Aug. 1997;91(4):586-93.
Major et al., Chapter 34 Hepatitis C Viruses. In Fields' Virology. 2001; 1:1127-61.
Maltese et al., Sequence context of antisense RelA/NF-kappa B phosphorothioates determines specificity. Nucleic Acids Res. Apr. 11, 1995;23(7):1146-51.
Manegold et al., Addition of PF-3512676 (CpG 7909) to a taxane/platinum regimen for first-line treatment of unresectable non-small cell lung cancer (NSCLC) improves objective response—Phase II clinical trial. Pfizer Poster. 2005. Abstract 1131.
Manzel et al., CpG-oligodeoxynucleotide-resistant variant of WEHI 231 cells. J Leukoc Biol. Nov. 1999;66(5):817-21.
Matsukura et al., Regulation of viral expression of human immunodeficiency virus in vitro by an antisense phosphorothioate oligodeoxynucleotide against rev (art/trs) in chronically infected cells. Proc Natl Acad Sci U S A. Jun. 1989;86(11):4244-8.
McCluskie et al., CpG DNA as mucosal adjuvant. Immunol Letts. 1999;69(1):30-1. Abstract #5.2.
McCluskie et al., CpG DNA as mucosal adjuvant. Vaccine. 2000;18:231-71.
McCluskie et al., Novel adjuvant systems. Curr Drug Targets Infect Disord. Nov. 2001;1(3):263-71.
McCluskie et al., Treatment of intravaginal HSV-2 infection in mice: a comparison of CpG oligodeoxynucleotides and resiquimod (R-848). Antiviral Res. Feb. 2006;69(2):77-85. Epub Dec. 5, 2005.
McCluskie et al., Enhancement of infectious disease vaccines through TLR9-dependent recognition of CpG DNA. Curr Top Microbiol Immunol. 2006;311:155-78. Abstract Only.
McHutchison et al., Early viral response to CpG 10101, in combination with pegylated interferon and/or ribavirin, in chronic HCV genotype 1 infected patients with prior relapse response. 41$^{st}$ Annual Meeting of European Association for the Study of the Liver (EASL). Apr. 26-30, 2006. Vienna, Austria; Submitted Abstract.
McHutchison et al., Final results of a multi-center phase 1B, randomized, placebo-controlled, dose-escalation trial of CpG 10101 in patients with chronic hepatitis C virus. 41$^{st}$ Annual Meeting of European Association for the Study of the Liver (EASL). Apr. 30, 2006. Vienna, Austria; Presented Abstract #111.
McHutchison et al., Early clinical results with CpG 10101, a new investigational antiviral TLR9 agonist being developed for treatment of subjects chronically infected with hepatitis C virus. 12$^{th}$ International Symposium on Viral Hepatitis and Liver Disease (ISVHLD). Jul. 3, 2006, Paris, France; Presented Abstract #O105.
Ochiai et al., Studies on lymphocyte subsets of regional lymph nodes after endoscopic injection of biological response modifiers in gastric cancer patients. Int J Immunotherapy. 1986;11(4):259-65.
Oehen et al., Antiviral protection after DNA vaccination is short lived and not enhanced by CpG DNA. Immunology. Feb. 2000;99(2):163-9.
Perlaky et al., Growth inhibition of human tumor cell lines by antisense oligonucleotides designed to inhibit p120 expression. Anticancer Drug Des. Feb. 1999;8(1):3-14.
Pisetsky et al., The influence of base sequence on the immunological properties of defined oligonucleotides. Immunopharmacology. Nov. 1998;40(3):199-208.
Polanczyk et al., Immunostimulatory effects of DNA and CpG motifs. Cent Eur J of Immunol. 2000;25(3):160-6.
Ratajczak et al., In vivo treatment of human leukemia in a scid mouse model with c-myb antisense oligodeoxynucleotides. Proc Natl Acad Sci U S A. Dec. 15, 1992;89(24):11823-7.
Raz et al., Potential role of immunostimulatory DNA sequences (ISS) in genetic immunization and autoimmunity. ACR Poster Session C: Cytokines and Inflammatory Mediators. Oct. 20, 1996; Abstract 615.
Robertson et al., Crohn's trial shows the pros of antisense. Nat Biotechnol. Mar. 1997;15(3):209.
Rynkiewicz et al., Marked enhancement of antibody response to anthrax vaccine adsorbed with Cpg 7909 in healthy volunteers. 45$^{th}$ Intersci. Conf. Antimicrob. Agents Chemother. Sep. 21-24, 2005; New Orleans, Louisiana. Meeting Poster.
Satoh et al., The study of mechanisms in CpG oligodeoxynucleotides-induced aggravation in murine allergic contact dermititis to 2,4-dinitrofluorobenzene. Fukushima Igaku Zasshi. 2002;52(3):237-50. Abstract Only.
Schijns et al., Immunological concepts of vaccine adjuvant activity. Curr Opin Immunol. 2000;12:456-463.
Sedegah et al., Interleukin 12 induction of interferon gamma-dependent protection against malaria. Proc Natl Acad Sci U S A. Oct. 25, 19994;91(22):10700-2.
Shalaby, Development of oral vaccines to stimulate mucosal and systemic immunity: barriers and novel strategies. Clin Immunol Immunopathol. Feb. 1995;74(2):127-34.
Sidman et al., Gamma-interferon is one of several direct B cell-maturing lymphokines. Nature. Jun. 28-Jul. 4 1984;309(5970):801-4.
Sonehara et al., Hexamer palindromic oligonucleotides with 5'-CG-3' motif(s) induce production of interferon. J Interferon Cytokine Res. Oct. 1996;16(10):799-803.
Sparwasser et al., Immunostimulatory CpG-oligodeoxynucleotides cause extramedullary murine hemopoiesis. J Immunol. Feb. 15, 1999;162(4):2368-74.
Stein et al., Problems in interpretation of data derived from in vitro and in vivo use of antisense oligodeoxynucleotides. Antisense Res Dev. 1994 Summer;4(2):67-9.
Stein et al., Non-antisense effects of oligodeoxynucleotides. Antisense Technology. 1997; Ch. 11: 241-64.
Sun et al., DNA as an adjuvant: capacity of insect DNA and synthetic oligodeoxynucleotides to augment T cell responses to specific antigen. J Exp Med. Apr. 6, 1998;187(7):1145-50.
Van Ojik et al., Phase I/II study with CpG 7909 as adjuvant to vaccination with Mage-3 protein in patients with Mage-3 positive tumors. Ann Oncol. 2003;13:157. Abstract 579O.
Vlassov et al., In Vivo pharmacokinetics of oligonucleotides following administration by different routes. CRC Press, Inc. Chapter 5. 1995:71-83.
Wagner et al., CpG motifs are efficient adjuvants for genetic vaccines to induce antigen-specific.protective anti-tumor T cell responses. 2000;203:429. Abstract R46.
Weeratna et al., TLR agonists as vaccine adjuvants: comparison of CpG ODN and Resiquimod.(R-848). Vaccine. 2005;23:5263-5270.
Weiner, The immunobiology and clinical potential of immunostimulatory CpG oligodeoxynucleotides. J Leukoc Biol. Oct. 2000;68(4):455-63.
Weiner et al., Immunostimulatory CpG oligodeoxynucleotide is effective as an adjuvant in inducing production of anti-idiotype antibody and is synergistic with GMCSF. Blood. Nov. 15, 1996;88(10):Suppl. 1 pt. 1. Abstract #348.
Whalen et al., DNA-mediated immunization to the hepatitis B surface antigen. Activation and entrainment of the immune response. Ann N Y Acad Sci. Nov. 1995 27;772:64-76.
Whitesell et al., Stability, clearance, and disposition of intraventricularly administered oligodeoxynucleotides: implications for therapeutic application within the central nervous system. Proc Natl Acad Sci U S A. May 15, 1993;90(10):4665-9.
Whitmore et al., LPD lipoplyplex initiates a potent cytokine response and inhibits tumor growth. Gene Ther. 1999;6:1867-75.
Wooldridge et al., Select unmethylated CpG oligodeoxynucleotide improve antibody dependent cellular cytotoxicity in vitro and in vivo. Proc Am Assoc Cancer Res. Mar. 1996;37(3253):477. Abstract.

(56) References Cited

OTHER PUBLICATIONS

Wooldridge et al., Immunostimulatory oligodeoxynucleotides containing CpG motifs enhance the efficacy of monoclonal antibody therapy of lymphoma. Blood. Apr. 15, 1997;89(8):2994-8.
Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4. Japanese.
Yamamoto et al., Oligodeoxyribonucleotides with 5'-ACGT-3' or 5'-TCGA-3' sequence induce production of interferons. Curr Top Microbiol Immunol. 2000;247:23-39.
Yamamoto, Cytokine production inducing action of oligo DNA. Rinsho Meneki. 1997; 29(9): 1178-84. Japanese.
Yew et al., Contribution of plasmid DNA to inflammation in the lung after administration of cationic lipid:pDNA complexes. Hum Gene Ther. Jan. 20, 1999;10:223-34.
Yi et al., CpG DNA rescue of murine B lymphoma cells from anti-IgM-induced growth arrest and programmed cell death is associated with increased expression of c-myc and bcl-xL. J Immunol. Dec. 1, 1996;157(11):4918-25.
Zhao et al., Modulation of oligonucleotide-induced immune stimulation by cyclodextrin analogs. Biochem Pharmacol. Nov. 22, 1996;52(10):1537-44.
Zimmermann et al., CpG oligodeoxynucleotides trigger protective and curative TH1 responses in lethal murine leishmaniasis. J Immunol. Apr. 15, 1998;160(8):3627-30.
Freytag et al., Mucosal adjuvants. Vaccine. Mar. 7, 2005;23(15):1804-13.
Lamm et al., Mechanisms of Ig-A mediated mucosal defense. Vaccine Research. 1992;1(3):169-173.
Snider, The mucosal adjuvant activities of ADP-ribosylating bacterial enterotoxins. Crit Rev Immunol. 1995;15(3-4):317-48.
Stevceva et al., Mucosal HIV vaccines: where are we now? Curr HIV Res. Jan. 2004;2(1):1-10.
Decision revoking the European Patent (Art. 101(2) and 101(3)(b) EPC) mailed Dec. 28, 2009 in connection with European Application No. 99925754.6 (European Patent No. 1 077 722).
The minutes in accordance with Rule 124(4) EPC mailed Dec. 28, 2009 in connection with European Application No. 99925754.6 (European Patent No. 1 077 722).
Cooper et al., CPG 7909, an immunostimulatory TLR9 agonist oligodeoxynucleotide, as adjuvant to Engerix-B HBV vaccine in healthy adults: a double-blind phase I/II study. J Clin Immunol. Nov. 2004;24(6):693-701.
Davis et al., DNA vaccines for prophylactic or therapeutic immunization against hepatitis B virus. Mt Sinai J Med. Mar. 1996;66(2):84-90.
De La Rosa et al., Microbiological quality of pharmaceutical raw materials. Pharm Acta Helv. Sep. 1995;70(3):227-32.
Diwan et al., Biodegradable nanoparticle mediated antigen delivery to human cord blood derived dendritic cells for induction of primary T cell responses. J Drug Target. 2003;11(8-10):495-507.
Gao et al., Swelling of hydroxypropyl methylcellulose matrix tablets. 2. Mechanistic study of the influence of formulation variables on matrix performance and drug release. J Pharm Sci. Jul. 1996;85(7):732-40.
Gombotz et al., Protein release from alginate matrices. Adv Drug Deliv Rev. May 4, 1998;31(3):267-285.

Horner et al., Immunostimulatory DNA is a potent mucosal adjuvant. Cell Immunol. Nov. 25, 1998;190(1):77-82.
Li et al., Enhanced immune response to T-independent antigen by using CpG oligodeoxynucleotides encapsulated in liposomes. Vaccine. Oct. 12, 2001;20(1-2):148-57.
Lipford et al., CpG-containing synthetic oligonucleotides promote B and cytotoxic T cell responses to protein antigen: a new class of vaccine adjuvants. Eur J Immunol. Sep. 1997;27(9):2340-4.
McCluskie et al., CpG DNA is a potent enhancer of systemic and mucosal immune responses against hepatitis B surface antigen with intranasal administration to mice. J Immunol. Nov. 1, 1998;161(9):4463-6.
Mui et al., Immune stimulation by a CpG-containing oligodeoxynucleotide is enhanced when encapsulated and delivered in lipid particles. J Pharmacol Exp Ther. Sep. 2001;298(3):1185-92.
Mutwiri et al., Strategies for enhancing the immunostimulatory effects of CpG oligodeoxynucleotides. J Control Release. May 31, 2004;97(1):1-17.
Oxenius et al., CpG-containing oligonucleotides are efficient adjuvants for induction of protective antiviral immune responses with T-cell peptide vaccines. J Virol. May 1999;73(5):4120-6.
Schijns. Immunological concepts of vaccine adjuvant activity. Curr Opin Immunol. Aug. 2000;12(4):456-63.
Semple et al., Immunogenicity and rapid blood clearance of liposomes containing polyethylene glycol-lipid conjugates and nucleic Acid. J Pharmacol Exp Ther. Mar. 2005;312(3):1020-6.
Shao et al., CpG-containing oligodeoxynucleotide 1826 converts the weak uveitogenic rat interphotoreceptor retinoid-binding protein peptide 1181-1191 into a strong uveitogen. J Immunol. Nov. 1, 2003;171(9):4780-5.
Suzuki et al., Liposome-encapsulated CpG oligodeoxynucleotides as a potent adjuvant for inducing type 1 innate immunity. Cancer Res. Dec. 1, 2004;64(23):8754-60.
Tafaghodi et al., Induction of systemic and mucosal immune responses by intranasal administration of alginate microspheres encapsulated with tetanus toxoid and CpG-ODN. Int J Pharm. Aug. 17, 2006;319(1-2):37-43.
Tam et al., Liposomal encapsulation enhances the activity of immunostimulatory oligonucleotides Future Lipidology. Feb. 2006; 1(1): 35-46.
Ugozzoli et al., Intranasal immunization of mice with herpes simplex virus type 2 recombinant gD2: the effect of adjuvants on mucosal and serum antibody responses. Immunology. Apr. 1998;93(4):563-71.
Von Hunolstein et al., Synthetic oligodeoxynucleotide containing CpG motif induces an anti-polysaccharide type 1-like immune response after immunization of mice with Haemophilus influenzae type b conjugate vaccine. Int Immunol. Mar. 2000;12(3):295-303.
Von Hunolstein et al., The adjuvant effect of synthetic oligodeoxynucleotide containing CpG motif converts the anti-Haemophilus influenzae type b glycoconjugates into efficient anti-polysaccharide and anti-carrier polyvalent vaccines. Vaccine. Apr. 30, 2001;19(23-24):3058-66.
Wang et al., Synergy between CpG- or non-CpG DNA and specific antigen for B cell activation. Int Immunol. Feb. 2003;15(2):223-31.
Weeratna et al., TLR agonists as vaccine adjuvants: comparison of CpG ODN and Resiquimod (R-848). Vaccine. Nov. 1, 2005;23(45):5263-70.

\* cited by examiner

Figure 8  The Effect of different prime/boost strategies on systemic humoral responses.

Figure 10  Effect of prime/boost strategies on T-cell proliferation

Figure 11  Effect of prime/boost strategies on IgA in lung washes

SEQUENCE LISTING

<160> NUMBER OF SEQ ID NOS: 95

<210> SEQ ID NO 1
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1
gctagacgtt agcgt                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 2
gctagatgtt agcgt                                                    15

<210> SEQ ID NO 3
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<223> OTHER INFORMATION: Synthetic Sequence

<400> SEQUENCE: 3
gctagacgtt agcgt                                                    15

<210> SEQ ID NO 4
<211> LENGTH: 15
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
<223> OTHER INFORMATION: Synthetic Sequence

<400> SEQUENCE: 4
gctagacgtt agcgt                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 5
gcatgacgtt gagct                                                    15

<210> SEQ ID NO 6
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 6
atggaaggtc cagcgttctc                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 7
atcgactctc gagcgttctc                                                  20

<210> SEQ ID NO 8
<211> LENGTH: 20
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<223> OTHER INFORMATION: Synthetic Sequence

<400> SEQUENCE: 8
atcgactctc gagcgttctc                                                  20

<210> SEQ ID NO 9
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<223> OTHER INFORMATION: Synthetic Sequence

<400> SEQUENCE: 9
atcgactctc gagcgttctc                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 10
atggaaggtc caacgttctc                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
gagaacgctg gaccttccat                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 12
gagaacgctc gaccttccat                                                  20

```
<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
gagaacgctc gaccttcgat                                                 20

<210> SEQ ID NO 14
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<223> OTHER INFORMATION: Synthetic Sequence

<400> SEQUENCE: 14
gagaacgctg gaccttccat                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 15
gagaacgatg gaccttccat                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 16
gagaacgctc cagcactgat                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 17
tccatgtcgg tcctgatgct                                                 20

<210> SEQ ID NO 18
<211> LENGTH: 20
<212> TYPE: DNA
<213> ORGANISM: Artificial Sequence
<220> FEATURE:
<221> NAME/KEY: modified_base
<222> LOCATION: (12)...(12)
<223> OTHER INFORMATION: m5c
<223> OTHER INFORMATION: Synthetic Sequence

<400> SEQUENCE: 18
tccatgtcgg tcctgatgct                                                 20

<210> SEQ ID NO 19
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 19
tccatgacgt tcctgatgct                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 20
tccatgtcgg tcctgctgat                                               20

<210> SEQ ID NO 21
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 21 tcaacgtt                                                            8

<210> SEQ ID NO 22
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 22 tcagcgct                                                            8

<210> SEQ ID NO 23
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 23 tcatcgat                                                            8

<210> SEQ ID NO 24
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 24 tcttcgaa                                                            8

<210> SEQ ID NO 25
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 25
```

-continued

```
caacgtt                                                             7

<210> SEQ ID NO 26
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 26 ccaacgtt                                                            8

<210> SEQ ID NO 27
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 27 aacgttct                                                            8

<210> SEQ ID NO 28
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 28 tcaacgtc                                                            8

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
atggactctc cagcgttctc                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 30
atggaaggtc caacgttctc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
atcgactctc gagcgttctc                                              20

<210> SEQ ID NO 32
<211> LENGTH: 20
<212> TYPE: DNA
<213> ORGANISM: Artificial Sequence
<220> FEATURE:
```

```
<223> OTHER INFORMATION: Synthetic Sequence

<400> SEQUENCE: 32
atggaggctc catcgttctc                                              20

<210> SEQ ID NO 33
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<223> OTHER INFORMATION: Synthetic Sequence

<400> SEQUENCE: 33
atcgactctc gagcgttctc                                              20

<210> SEQ ID NO 34
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<223> OTHER INFORMATION: Synthetic Sequence

<400> SEQUENCE: 34
atcgactctc gagcgttctc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
tccatgtcgg tcctgatgct                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
tccatgccgg tcctgatgct                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
tccatggcgg tcctgatgct                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 38
tccatgacgg tcctgatgct                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
tccatgtcga tcctgatgct                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
tccatgtcgc tcctgatgct                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
tccatgtcgt ccctgatgct                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 42
tccatgacgt gcctgatgct                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
tccataacgt tcctgatgct                                          20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
tccatgacgt ccctgatgct                                          20

<210> SEQ ID NO 45
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 45
tccatcacgt gcctgatgct                                              20

<210> SEQ ID NO 46
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 46
ggggtcaacg ttgacgggg                                               19

<210> SEQ ID NO 47
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 47
ggggtcagtc gtgacgggg                                               19

<210> SEQ ID NO 48
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 48
gctagacgtt agtgt                                                   15

<210> SEQ ID NO 49
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 49
tccatgtcgt tcctgatgct                                              20

<210> SEQ ID NO 50
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 50
accatggacg atctgtttcc cctc                                         24

<210> SEQ ID NO 51
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 51
tctcccagcg tgcgccat                                                18
```

```
<210> SEQ ID NO 52
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 52
accatggacg aactgtttcc cctc                                              24

<210> SEQ ID NO 53
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 53
accatggacg agctgtttcc cctc                                              24

<210> SEQ ID NO 54
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 54
accatggacg acctgtttcc cctc                                              24

<210> SEQ ID NO 55
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 55
accatggacg tactgtttcc cctc                                              24

<210> SEQ ID NO 56
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 56
accatggacg gtctgtttcc cctc                                              24

<210> SEQ ID NO 57
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 57
accatggacg ttctgtttcc cctc                                              24

<210> SEQ ID NO 58
<211> LENGTH: 15
<212> TYPE: DNA
<213> ORGANISM: Artificial Sequence
<220> FEATURE:
<223> OTHER INFORMATION: Synthetic Sequence
```

-continued

<400> SEQUENCE: 58
cacgttgagg ggcat                                                        15

<210> SEQ ID NO 59
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 59
tcagcgtgcg cc                                                           12

<210> SEQ ID NO 60
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 60
atgacgttcc tgacgtt                                                      17

<210> SEQ ID NO 61
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 61
tctcccagcg ggcgcat                                                      17

<210> SEQ ID NO 62
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 62
tccatgtcgt tcctgtcgtt                                                   20

<210> SEQ ID NO 63
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 63
tccatagcgt tcctagcgtt                                                   20

<210> SEQ ID NO 64
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 64
tcgtcgctgt ctccccttct t                                                 21

<210> SEQ ID NO 65
<211> LENGTH: 19
<212> TYPE: DNA

```
<213> ORGANISM: Artificial Sequence
<220> FEATURE:
<223> OTHER INFORMATION: Synthetic Sequence

<400> SEQUENCE: 65
tcctgacgtt cctgacgtt                                                    19

<210> SEQ ID NO 66
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 66
tcctgtcgtt cctgtcgtt                                                    19

<210> SEQ ID NO 67
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 67
tccatgtcgt ttttgtcgtt                                                   20

<210> SEQ ID NO 68
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 68
tcctgtcgtt ccttgtcgtt                                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 69
tccttgtcgt tcctgtcgtt                                                   20

<210> SEQ ID NO 70
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 70
tcctgtcgtt ttttgtcgtt                                                   20

<210> SEQ ID NO 71
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 71
tcgtcgctgt ctgcccttct t                                                 21
```

-continued

```
<210> SEQ ID NO 72
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 72
tcgtcgctgt tgtcgtttct t                                          21

<210> SEQ ID NO 73
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 73
tccatgcgtg cgtgcgtttt                                            20

<210> SEQ ID NO 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
tccatgcgtt gcgttgcgtt                                            20

<210> SEQ ID NO 75
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 75
tccacgacgt tttcgacgtt                                            20

<210> SEQ ID NO 76
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 76
tcgtcgttgt cgttgtcgtt                                            20

<210> SEQ ID NO 77
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 77
tcgtcgtttt gtcgttttgt cgtt                                       24

<210> SEQ ID NO 78
<211> LENGTH: 22
<212> TYPE: DNA
<213> ORGANISM: Artificial Sequence
<220> FEATURE:
<223> OTHER INFORMATION: Synthetic Sequence
```

-continued

```
<400> SEQUENCE: 78
tcgtcgttgt cgttttgtcg tt                                              22

<210> SEQ ID NO 79
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 79
gcgtgcgttg tcgttgtcgt t                                               21

<210> SEQ ID NO 80
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 80
tgtcgtttgt cgtttgtcgt t                                               21

<210> SEQ ID NO 81
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 81
tgtcgttgtc gttgtcgttg tcgtt                                           25

<210> SEQ ID NO 82
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 82
tgtcgttgtc gttgtcgtt                                                  19

<210> SEQ ID NO 83
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 83
tcgtcgtcgt cgtt                                                       14

<210> SEQ ID NO 84
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 84
tgtcgttgtc gtt                                                        13

<210> SEQ ID NO 85
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 85
tccatagcgt tcctagcgtt                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 86
tccatgacgt tcctgacgtt                                              20

<210> SEQ ID NO 87
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 87 gtcgyt                                                              6

<210> SEQ ID NO 88
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 88 tgtcgyt                                                             7

<210> SEQ ID NO 89
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 89
agctatgacg ttccaagg                                                18

<210> SEQ ID NO 90
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 90
tccatgacgt tcctgacgtt                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 91
tccaggactt ctctcaggtt                                              20
```

```
<210> SEQ ID NO 92
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 92
atcgactctc gaacgttctc                                                20

<210> SEQ ID NO 93
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 93
tccatgtcgg tcctgacgca                                                20

<210> SEQ ID NO 94
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 94 tcttcgat                                                              8

<210> SEQ ID NO 95
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 95
ataggaggtc caacgttctc                                                20
```

METHODS AND PRODUCTS FOR INDUCING MUCOSAL IMMUNITY

This Application claims priority to U.S. Provisional Patent Application No. 60/086,393, filed May 22, 1998.

FIELD OF THE INVENTION

The present invention relates methods and products for inducing mucosal immunity. In particular, the invention relates to the use of immunostimulatory oligonucleotides containing a CpG motif alone or in combination with other mucosal adjuvants for inducing mucosal immunity.

BACKGROUND OF THE INVENTION

Two distinct compartments of the immune system have been identified: (i) the systemic, which comprises the bone marrow, spleen and lymph nodes, and (ii) the mucosal, which comprises lymphoid tissue associated with mucosal surfaces and external secretory glands (McGhee et al., 1992). Mucosal surfaces are associated with the gastrointestinal (GI), genitourinary (GU) and respiratory tracts. Each compartment is associated with both humoral (antibodies) and cell-mediated (cytotoxic T-cells) responses, however there are differences in the nature of the immune responses induced in each compartment. Antibodies associated with the systemic compartment are predominantly of the IgG isotype, which function to neutralize pathogens in the circulatory system. In contrast, antibodies in the mucosae are primarily secretory IgA (S-IgA), which function to prevent entry of the pathogen into the body via the mucosal surface (Lamm et al., 1992). Systemic immunity cannot prevent entry of pathogenic organisms at mucosal surfaces.

Successful systemic immunization (i.e., delivery of antigen to the systemic compartment) will induce systemic immunity but does not usually yield mucosal immune responses. In contrast, antigen delivered at mucosal surfaces triggers both mucosal (at local and sometimes at distant sites) and systemic responses (Haneberg et al., 1994, Gallichan and Rosenthal, 1995).

Most vaccines developed to date are delivered parenterally, for example by intramuscular (IM) or intradermal (ID) injection, and as such induce primarily systemic immunity. However, the combined mucosal surface area is more than 200 times greater than that of the skin and is the primary site of transmission of numerous infectious diseases. Therefore, current vaccination strategies permit the pathogen to enter the body and only fight it once it is in circulation. Infection and morbidity rates could be reduced if effective mucosal immunity could be induced. Furthermore, there is evidence that mucosal vaccines may have a broader age range of recipients. Finally, mucosal vaccines are often administered by non-invasive means (e.g., nose drops, nasal spray, inhaled nebulizer), thus they are easier and less expensive to administer, have less need for trained personnel and no risk of needle stick injury or cross contamination (for reviews see Mestecky et al., 1992, Staats et al 1994, O, Hagan 1994).

As mentioned above, the hallmark of mucosal immunity is local production of S-IgA antibodies. These constitute >80% of all antibodies in mucosae-associated tissues and are induced, transported and regulated by mechanisms quite distinct from those of the systemic response. IgA is of primary importance to the host defense because it acts not only to resist strict mucosal pathogens but also of the many microorganisms which initially colonize mucosal surfaces but subsequently cause systemic disease. There appear to be three sites of IgA mediated mucosal defense: (i) in the lumen, where S-IgA can neutralize viruses, bacterial toxins and enzymes, and act as a mucosal barrier to prevent viral attachment, microbial adherence and adsorption of antigen; (ii) within epithelial cells where dimeric IgA can bind to intracellular antigen; (iii) within the lamina propria where dimeric IgA can complex with antigen and the immune complex thus formed transported to the lumen (Lamm et al., 1992).

Many vaccines in development are composed of synthetic or recombinant antigens (peptides or polypeptides). These are considered safer than traditional attenuated or inactivated whole pathogens, however they are often poorly immunogenic and require adjuvants to enhance specific immunity. For systemic administration, aluminum precipitates (alum) may be added to the antigens to augment immune responses. Alum is currently the only adjuvant licensed for human use in most countries including the USA, however it is not suitable for delivery to mucosal surfaces. Therefore most mucosal vaccines used today contain live-attenuated organisms, and little success has been obtained with mucosal delivery of subunit vaccines.

Cholera toxin (CT) is the mucosal adjuvant most commonly used in animal models. CT is the primary enterotoxin produced by *Vibrio cholerae*. It is an 84 kilodalton polymeric protein consisting of two subunits, a monomeric A subunit and a pentameric ring shaped B subunit. The B subunit binds GM1 gangliosides at the surface of eukaryotic cells and enables insertion of the A subunit into the cytosol, where it ADP-ribosylates GTP-binding regulatory protein associated with adenylate cyclase (Spangler, 1992).

CT enhances antigen presentation by macrophages, epithelial cells and B cells, promotes differentiation and isotype switching in B cells, and has complex inhibitory and stimulatory effects on T-cell proliferation and lymphokine production (Snider, 1995). Some groups report that CT can selectively activate Th2-type CD4+ T cells while inhibiting Th1-type cells (Takahashi et al., 1996,) while others report activation of both TH1 and Th2-type CD4+ T cells (Hornquist and Lycke, 1993). Differences may be due to a number of factors including route of immunization and the nature of the antigen.

The *Escherichia coli* heat-labile enterotoxin (labile toxin, LT) is structurally and functionally closely related to CT, and has similar adjuvant properties (Lycke et al., 1992). LT can confer immunity to co-administered antigens that are on their own non-immunogenic when administered by mucosal routes; this adjuvant effect is noted whether LT is simply mixed with or is physically coupled to the antigen (Holmgren et al., 1993).

While very effective as mucosal adjuvants in animal models, CT and LT are highly toxic, and especially so in humans. Genetically detoxified mutants of both CT and LT have been developed by using site-directed mutagenesis, which, at least in animal models appear to be less toxic yet retain some adjuvanticity (e.g., LTK63 is LT with a single substitution at serine-63) (Rappuoli et al., 1995, Douce et al., 1994, Pizza et al., 1994, De Haan et al., 1996). Nevertheless, the level of adjuvanticity appears to be proportional to the level of retained toxicity, and thus there is a clear need for an alternative safe and effective mucosal adjuvant.

SUMMARY OF THE INVENTION

The present invention relates to methods and products for inducing immune responses using immunostimulatory CpG dinucleotide containing oligonucleotides. In one aspect the invention is a method for inducing a mucosal immune response. The method includes the step of administering to a mucosal surface of a subject an effective amount for inducing a mucosal immune response of an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and exposing the subject to an antigen to induce the mucosal immune response, and wherein the antigen is not encoded in a nucleic acid vector.

In another aspect the invention is a method for inducing a mucosal immune response. The method includes the step of administering to a mucosal surface of a subject an effective amount for inducing a mucosal immune response of an antigen and a plasmid vector, having a sequence including at least the following formula:

$$5'X_1X_2CGX_3X_4 3'$$

wherein C and G are unmethylated, wherein $X_1$, $X_2$, $X_3$, and $X_4$ are nucleotides.

In one embodiment the antigen is not encoded in a nucleic acid vector. In another embodiment the antigen is encoded by a nucleic acid vector, which optionally may be the plasmid vector. In yet another embodiment the plasmid vector includes a nucleic acid sequence which operatively encodes for a cytokine. Preferably the antigen and the plasmid vector are administered orally or intranasally. In some embodiments at least 50 μg of the plasmid vector is administered to the subject.

According to another aspect of the invention a method for inducing a mucosal immune response is provided. The method includes the step of administering to a mucosal surface of a subject an effective amount for inducing a mucosal immune response of an antigen and of an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and wherein the antigen is encoded by a nucleic acid vector. Preferably the antigen and the oligonucleotide are administered orally or intranasally.

In some embodiments of the invention the oligonucleotide has a backbone selected from the group consisting of a phosphodiester backbone and a chimeric backbone. In other embodiments the oligonucleotide has a phosphorothioate backbone. In the embodiments wherein the oligonucleotide has a phosphorothioate backbone and wherein the antigen is encoded by a nucleic acid vector and the CpG is an oligonucleotide it is a preferred but not limited embodiment that the plasmid and oligonucleotides are delivered with a colloidal dispersion system. In some embodiments the colloidal dispersion system is selected from the group consisting of macromolecular complexes, nanocapsules, microspheres, beads, and lipid-based systems. In other embodiments the plasmid and oligonucleotide are coated onto gold particles and are delivered with a gene-gun.

A method for inducing a mucosal immune response in a subject is provided in other aspects. The method involves the step of administering to a subject an antigen and an effective amount for inducing a mucosal immune response of an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and administering to the subject a hormone to induce the mucosal immune response.

In one embodiment the antigen and the oligonucleotide are administered to a mucosal surface of the subject. In another embodiment the hormone is administered systemically. In one embodiment the hormone is encoded by a nucleic acid vector.

The invention in other aspects involves methods for inducing an immune response. The method involves the steps of orally, intranasally, ocularly, vaginally, or rectally administering to a subject an effective amount for inducing an immune response of an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and exposing the subject to an antigen to induce the immune response.

In some embodiments the antigen is administered orally, intranasally, ocularly, vaginally, or rectally. In other embodiments the antigen is administered simultaneously with the oligonucleotide. Preferably the oligonucleotide is administered in an effective amount for inducing mucosal immunity.

According to other aspects the invention is a method for inducing an immune response. The method involves the step of orally, intranasally, ocularly, vaginally, or rectally administering to a subject an effective amount for inducing an immune response of a CpG containing plasmid, having a sequence including at least the following formula:

$$5'X_1X_2CGX_3X_4 3'$$

wherein C and G are unmethylated, wherein $X_1$, $X_2$, $X_3$, and $X_4$ are nucleotides, and exposing the subject to an antigen to induce the immune response.

In some embodiments the antigen is administered orally, intranasally, ocularly, vaginally, or rectally. In other embodiments the antigen is administered simultaneously with the CpG containing plasmid. Preferably the CpG containing plasmid is administered in an effective amount for inducing mucosal immunity.

The methods involve an induction of mucosal immunity. Mucosal immunity can be induced in a local and/or remote site. In some embodiments the mucosal immunity is induced in a local site and in others the mucosal immunity is induced in a remote site, or both.

In order to induce a mucosal immune response the CpG oligonucleotide can be administered with a prime dose, a boost dose or both. For instance the CpG oligonucleotide may be administered with a priming dose of antigen. In another embodiment the CpG oligonucleotide is administered with a boost dose of antigen. In some embodiments the subject is administered a priming dose of antigen and CpG oligonucleotide before the boost dose. In yet other embodiments the subject is administered a boost dose of antigen and CpG oligonucleotide after the priming dose.

In another aspect the invention is a method for inducing a systemic immune response. The method involves administering to a mucosal surface of a subject an effective amount for inducing a systemic immune response of an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and administering to the mucosal surface of the subject an antigen to induce the systemic immune response. In one embodiment the antigen is not encoded in a nucleic acid vector, and wherein the antigen does not produce a systemic immune response when administered to the mucosal surface alone.

According to another aspect of the invention a method for inducing a systemic immune response is provided. The method involves the step of administering to a mucosal surface of a subject an effective amount for inducing a systemic immune response of a combination of a non-oligonucleotide mucosal adjuvant and an oligonucleotide, having a sequence including at least the following formula:

$$5'X_1X_2CGX_3X_4 3'$$

wherein C and G are unmethylated, wherein $X_1$, $X_2$, $X_3$, and $X_4$ are nucleotides, and exposing the subject an antigen to induce the systemic immune response.

In one embodiment the antigen is delivered to a mucosal surface. In another embodiment the antigen is not encoded in a nucleic acid vector.

The subject may be actively exposed to the antigen or passively exposed to the antigen. In one embodiment of the methods described herein the subject is actively exposed to the antigen and the antigen is delivered to a mucosal surface. In other embodiments the antigen is administered concurrently with the oligonucleotide. The antigen may be delivered alone or in conjunction with a colloidal dispersion system. In some embodiments the colloidal dispersion system is selected from the group consisting of macromolecular complexes, nanocapsules, microspheres, beads, and lipid-based systems. Lipid-based systems optionally include oil-in-water emulsions, micelles, mixed micelles, or liposomes.

In other embodiments the subject is passively exposed to the antigen through environmental contact. The subject that is passively exposed to the antigen in some embodiments is a subject at risk of developing an allergic reaction, an infectious disease, or a cancer. In other embodiments the subject has an infectious disease, a cancer, an allergy or is an asthmatic.

The antigen that is passively or actively administered to the subject is any type of antigen known in the art and includes for example cells, cell extracts, proteins, polypeptides, peptides, polysaccharides, polysaccharide conjugates, peptide mimics of polysaccharides, lipids, glycolipids, carbohydrates, allergens, viruses and viral extracts and muticellular organisms such as parasites. In one embodiment the antigen is derived from an infectious organism selected from the group consisting of infectious bacteria, infectious viruses, infectious parasites, and infectious fungi.

The method may also include the step of administering a non-oligonucleotide mucosal adjuvant in conjunction with the antigen. Non-oligonucleotide mucosal adjuvants may include, for example, cholera toxin, derivatives of cholera toxin, labile toxin, derivatives of labile toxin, alum, MLP, MDP, saponins such as QS21, cytokines, oil-in-water and other emulsion formulations such as MF59, SAF, Montanide ISA 720 and PROVAX, PCPP polymers, and ISCOMS.

In other embodiments the method includes the step of administering a cytokine or a B-7 costimulatory molecule to the subject.

In some embodiments, the oligonucleotide is administered orally, mucosally, ocularly, vaginally, rectally, or by inhalation to a subject.

The oligonucleotide may be modified. For instance, in some embodiments at least one nucleotide has a phosphate backbone modification. The phosphate backbone modification may be a phosphorothioate or phosphorodithioate modification. In some embodiments the phosphate backbone modification occurs on the 5' side of the oligonucleotide or the 3' side of the oligonucleotide.

The oligonucleotide may be any size. Preferably the oligonucleotide has 8 to 100 nucleotides. In other embodiments the oligonucleotide is 8 to 40 nucleotides in length.

In some embodiments $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA. Preferably $X_1X_2$ are GpA or GpT and $X_3X_4$ are TpT. In other preferred embodiments $X_1$ or $X_2$ or both are purines and $X_3$ or $X_4$ or both are pyrimidines or $X_1X_2$ are GpA and $X_3$ or $X_4$ or both are pyrimidines. In one embodiment $X_2$ is a T and $X_3$ is a pyrimidine. The oligonucleotide may be isolated or synthetic.

In some embodiments the oligonucleotide has a sequence including at least the following formula:

$$5'TCNTX_1X_2CGX_3X_4 3'$$

wherein $X_1$, $X_2$, $X_3$, and $X_4$ are nucleotides, N is a nucleic acid sequence composed of from about 0-25 nucleotides.

In other aspects, the invention encompasses pharmaceutical compositions for orally, intranasally, ocularly, vaginally, or rectally administering CpG oligonucleotides or CpG plasmids. In one aspect the composition is an oral formulation of a CpG oligonucleotide in a buffer for neutralizing biological acids. In another aspect the composition is an intranasal formulation of a CpG oligonucleotide in an aerosol. In other aspects the composition is a vaginal or rectal formulation of a CpG oligonucleotide in a suppository or other vehicle suitable for delivery to vaginal and rectal tissue. In other aspect the composition is an ocular formulation of a CpG oligonucleotide in a solution compatible with the eye. Such formulations are described herein as well as in Remingtons Pharmaceutical Sciences, which is hereby incorporated by reference.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE TABLES

Figure 1:
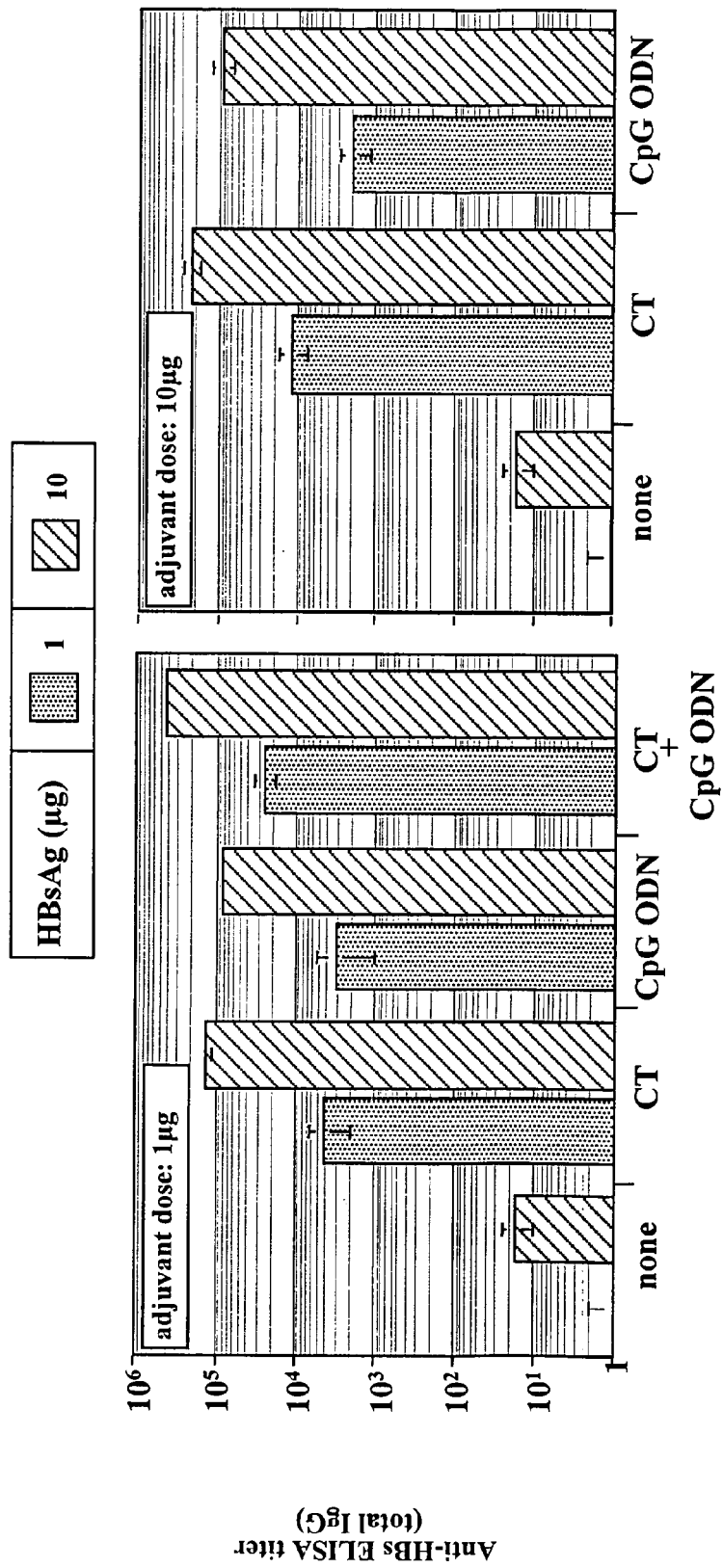
FIG. 1 is a bar graph depicting the effect of different adjuvants on total IgG titers of anti-HBS, wherein BALB/c mice were immunized by IN inhalation with HBsAg (1 or 10 μg) without or in combination with Cholera toxin (CT) and/or CpG oligonucleotide (motif #1826, SEQ ID NO. 90) adjuvants.

Table 1 lists immunostimulatory oligonucleotide sequences.

Table 2 lists the effect of different adjuvants on HBsAg-specific antibody isotypes.

[a]BALB/c mice were immunized by IN inhalation with HBsAg (1 µg) without or in combination with Cholera toxin (CT), *Escherichia coli* heat-labile enterotoxin (LT), the B subunit of Cholera toxin (CTB), a detoxified mutant of *Escherichia coli* heat-labile enterotoxin (LTK63) and/or CpG oligonucleotide (motif #1826, SEQ ID NO. 90) (1 or 10 µg) as adjuvants.

[b]Values represent the group geometric mean (GMT) of the ELISA end-point dilution titer for HBsAg-specific IgG1 or IgG2a antibodies in plasma taken 4 wk after immunization. Titers were defined as the highest plasma dilution resulting in an absorbance value two times that of non-immune plasma, with a cut-off value of 0.05.

[c]The IgG2a to IgG1 ratios (IgG2a:IgG1) are reported, with a value >1 indicating a predominantly Th-1 like response.

[d]N/A: Not applicable since no antibody responses detected.

[e]=: All mice immunized with these adjuvant combinations died within 96 hours.

Table 3 lists the effect of different adjuvants on HBsAg-specific IgA responses.

[a]BALB/c mice were immunized by IN inhalation with HBsAg (1 µg) without or in combination with Cholera toxin (CT), *Escherichia coli* heat-labile enterotoxin (LT), the B subunit of Cholera toxin (CTB), a detoxified mutant of *Escherichia coli* heat-labile enterotoxin (LTK63) and/or CpG oligonucleotide (motif #1826, SEQ ID NO. 90) (1 or 10 µg) as adjuvants. All groups contained 5 mice unless otherwise indicated.

[b]Values represent the geometric mean titers±the standard error of the mean (GMT±SEM) of the ELISA end-point dilution titer for HBsAg-specific IgA antibodies in lung wash or fecal solutions taken 4 wk after immunization.

[c]IgA titers in lung washes were defined as the highest dilution that resulted in an absorbance value (OD 450) two times greater than that of non-immune lung wash, with a cut-off value of 0.05.

[d]IgA titers in fecal extracts were expressed as OD 450×10³ above background (non-immune fecal extract). Seroconversion was defined as an endpoint titer for total IgG >100.

[e]=: All mice immunized with these adjuvant combinations died within 96 hours.

Table 4 shows the different mucosal/parenteral prime boost/strategies used to immunize BALB/c mice and summarizes the results as to which approach induced antigen-specific systemic and mucosal immune responses.

DETAILED DESCRIPTION OF THE INVENTION

The invention relates to methods and products for inducing immunity using immunostimulatory CpG oligonucleotides. One aspect of the invention is based on the finding that CpG oligonucleotides act as a potent mucosal adjuvants to induce immune responses at both local and remote sites against an antigen administered to the mucosal tissue. This finding is striking even in view of previous findings that CpG oligonucleotide is a potent adjuvant for systemic delivery, because with systemic delivery the protein alone induces detectable immune responses but with mucosal delivery the protein alone does not induce an immune response. As demonstrated in the Examples below, both systemic and mucosal immunity are induced by mucosal delivery of CpG oligonucleotides. The systemic immunity induced in response to CpG oligonucleotides included both humoral and cell-mediated responses to specific antigens that were not capable of inducing systemic immunity when administered alone to the mucosa. Furthermore, both CpG oligonucleotides and cholera toxin (CT, a mucosal adjuvant that induces a Th2-like response) induced CTL. This is surprising since with systemic immunization, the presence of Th2-like antibodies is normally associated with a lack of CTL (Schirmbeck et al., 1995).

Additionally, CpG oligonucleotides were found to induce a mucosal response at both local (e.g., lung) and remote (e.g., lower digestive tract) mucosal sites. Although CpG oligonucleotide was similar to CT for induction of systemic antibodies (IgG) and local mucosal antibodies (IgA), significant levels of IgA antibodies were induced at a distant mucosal site only by CpG oligonucleotide and not by CT. This was surprising because CT is generally considered to be a highly effective mucosal adjuvant. Another manner in which CpG oligonucleotide was superior to CT was with respect to the Th-type of response. As has been previously reported (Snider 1995), CT induces predominantly IgG1 isotype of antibodies, which are indicative of Th2-type response. In contrast, CpG oligonucleotide was more Th1 with predominantly IgG2a antibodies, especially after boost or when the two adjuvants were combined. Th1-type antibodies in general have better neutralizing capabilities, and furthermore, a Th2 response in the lung is highly undesirable because it is associated with asthma (Kay, 1996, Hogg, 1997). Thus the use of CpG oligonucleotide as a mucosal adjuvant has benefits that other mucosal adjuvants cannot achieve.

The discovery of CpG oligonucleotide as a safe and effective mucosal adjuvant is also advantageous because although CT is a highly effective mucosal adjuvant, it is too toxic for use in humans. A mouse (~20 g body weight) can tolerate the toxic effects of up to 10 µg of CT, however a dose as little as 1-5 µg will cause severe diarrhea in a human (~70 kg body weight) (Jertborn et al., 1992). Animals inhaling CpG oligonucleotide showed no short-term signs of distress over those receiving HBsAg alone, and all recovered quickly with no apparent long-lasting effects. CpG oligonucleotide is well tolerated at very high doses (e.g., greater than 100 µg), when delivered systemically or mucosally.

Thus in one aspect the invention is a method for inducing a mucosal immune response in a subject. The method includes the step of administering to a mucosal surface of a subject an effective amount for inducing a mucosal immune response of an oligonucleotide, having a sequence including at least the following formula:

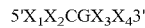

wherein C and G are unmethylated, wherein $X_1$, $X_2$, $X_3$, and $X_4$ are nucleotides, and exposing the subject to an antigen to induce the mucosal immune response. In other aspects the method involves administering a plasmid vector, having a sequence including at least the above formula instead of the oligonucleotide. The oligonucleotide, referred to herein as the oligonucleotide or the CpG oligonucleotide, is not a plasmid vector. These distinctions are made clear in the definitions set forth below. For purposes of brevity, the invention is described herein with respect to CpG oligonucleotides, but the description also applies to plasmid vectors.

The CpG oligonucleotide is particularly useful as a prophylactic vaccine for the induction of mucosal immunity of a subject at risk of developing an infection with an infectious organism or a subject at risk of developing an allergy or cancer. A "subject at risk" as used herein is a subject who has any risk of exposure to an infection causing infectious pathogen or an allergen or of developing cancer. For instance, a subject at risk may be a subject who is planning to travel to an area where a particular type of infectious agent or allergen is found or it may be a subject who through lifestyle or medical procedures is exposed to bodily fluids which may contain infectious organisms or even any subject living in an area that an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject is exposed to the antigen, i.e., during pollen season, then that subject is at risk of exposure to the antigen. Subjects at risk of developing cancer include those with a genetic predisposition or previously treated for cancer, and those exposed to carcinogens such as tobacco, asbestos, and other chemical toxins or excessive sunlight and other types of radiation.

In addition to the use of the CpG oligonucleotide for prophylactic treatment, the invention also encompasses the use of the CpG oligonucleotide for the treatment of a subject having an infection, an allergy or a cancer.

A "subject having an infection" is a subject that has been exposed to an infectious pathogen and has acute or chronic detectable levels of the pathogen in the body. The CpG oligonucleotide can be used with an antigen to mount an antigen specific mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A "subject having an allergy" is a subject that has or is at risk of developing an allergic reaction in response to an allergen. An "allergy" refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Currently, allergic diseases are generally treated by the injection of small doses of antigen followed by subsequent increasing dosage of antigen. It is believed that this procedure induces tolerization to the allergen to prevent further allergic reactions. These methods, however, can take several years to be effective and are associated with the risk of side effects such as anaphylactic shock. The methods of the invention avoid these problems.

Allergies are generally caused by IgE antibody generation against harmless allergens. The cytokines that are induced by mucosal administration of unmethylated CpG oligonucleotides are predominantly of a class called "Th1" (examples are IL-12 and IFN-γ) and these induce both humoral and cellular immune responses. The types of antibodies associated with a Th1 response are generally more protective because they have high neutralization and opsonization capabilities. The other major type of immune response, which is associated with the production of IL-4, IL-5 and IL-10 cytokines, is termed as Th2 immune response. Th2 responses involve solely antibodies and these have less protective effect against infection and some Th2 isotypes (e.g., IgE) are associated with allergy. In general, it appears that allergic diseases are mediated by Th2 type immune responses while Th1 responses provide the best protection against infection, although excessive Th1 responses are associated with autoimmune disease. Based on the ability of the CpG oligonucleotides to shift the immune response in a subject from a Th2 (which is associated with production of IgE antibodies and allergy) to a Th1 response (which is protective against allergic reactions), an effective dose for inducing a mucosal immune response of a CpG oligonucleotide can be administered to a subject to treat or prevent an allergy.

Thus, the CpG oligonucleotide has significant therapeutic utility in the treatment of allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. "Asthma" refers to a disorder of the respiratory system characterized by inflammation, narrowing of the airways and increased reactivity of the airways to inhaled agents. Asthma is frequently, although not exclusively associated with atopic or allergic symptoms.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject" shall mean a human or vertebrate animal including but not limited to a dog, cat, horse, cow, pig, sheep, goat, chicken, primate, e.g., monkey, fish (aquaculture species), e.g. salmon, rat, and mouse.

A CpG oligonucleotide is an oligonucleotide which includes at least one unmethylated CpG dinucleotide. An oligonucleotide containing at least one unmethylated CpG dinucleotide is a nucleic acid molecule which contains an unmethylated cytosine-guanine dinucleotide sequence (i.e. "CpG DNA" or DNA containing a 5' cytosine followed by 3' guanosine and linked by a phosphate bond) and activates the immune system. The CpG oligonucleotides can be double-stranded or single-stranded. Generally, double-stranded molecules are more stable in vivo, while single-stranded molecules have increased immune activity.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g. genomic or cDNA), but are preferably synthetic (e.g. produced by oligonucleotide synthesis). The entire CpG oligonucleotide can be unmethylated or portions may be unmethylated but at least the C of the 5' CG 3' must be unmethylated.

The methods of the invention may be accomplished by administering a CpG containing oligonucleotide or a CpG containing plasmid vector to the subject to induce a mucosal immune response. As used herein the terms a "CpG oligonucleotide" and a "plasmid expression vector" are mutually exclusive. The terms "CpG oligonucleotide" or "CpG nucleic acid" are used to refer to any CpG containing nucleic acid except for a CpG containing plasmid vector. A plasmid expression vector is a nucleic acid molecule which includes at least a promoter and a gene encoding a peptide or peptide fragment. The plasmid expression vector includes a nucleic acid sequence encoding the peptide which is operatively linked to a gene expression sequence which directs the expression of the peptide within a eukaryotic cell. The "gene expression sequence" is any regulatory nucleotide sequence, such as a promoter sequence or promoter-enhancer combination, which facilitates the efficient transcription and translation of the peptide to which it is operatively linked. The gene expression sequence may, for example, be a mammalian or viral promoter, such as a constitutive or inducible promoter. Such constructs are well known to those of skill in the art.

In one preferred embodiment the invention provides a CpG oligonucleotide represented by at least the formula:

$5'N_1X_1CGX_2N_23'$ wherein at least one nucleotide separates consecutive CpGs; $X_1$ is adenine, guanine, or thymine; $X_2$ is cytosine, adenine, or thymine; N is any nucleotide and $N_1$ and $N_2$ are nucleic acid sequences composed of from about 0-25 N's each.

In another embodiment the invention provides an isolated CpG oligonucleotide represented by at least the formula:

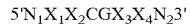

$5'N_1X_1X_2CGX_3X_4N_23'$ wherein at least one nucleotide separates consecutive CpGs; $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA; N is any nucleotide and $N_1$ and $N_2$ are nucleic acid sequences composed of from about 0-25 N's each. Preferably $X_1X_2$ are GpA or GpT and $X_3X_4$ are TpT. In other preferred embodiments $X_1$ or $X_2$ or both are purines and $X_3$ or $X_4$ or both are pyrimidines or $X_1X_2$ are GpA and $X_3$ or $X_4$ or both are pyrimidines. In a preferred embodiment $N_1$ and $N_2$ of the nucleic acid do not contain a CCGG or CGCG quadmer or more than one CCG or CGG trimer. The effect of a a CCGG or CGCG quadmer or more than one CCG or CGG trimer depends in part on the status of the oligonucleotide backbone. For instance, if the oligonucleotide has a phosphodiester backbone or a chimeric backbone the inclusion of these sequences in the oligonucleotide will only have minimal if any affect on the biological activity of the oligonucleotide. If the backbone is completely phosphorothioate or significantly phosphorothioate then the inclusion of these sequences may have more influence on the biological activity or the kinetics of the biological activity. In the case when the CpG oligonucleotide is administered in conjunction with an antigen which is encoded in a nucleic acid vector, it is preferred that the backbone of the CpG oligonucleotide be phosphodiester or chimeric. It can be completely phosphorothioate if the oligonucleotide is delivered directly to the cell. The cell may have a problem taking up a completely phosphorothioate oligonucleotide in the presence of a plasmid vector. Thus when both a vector and an oligonucleotide are delivered to a subject, it is preferred that the oligonucleotide have a phosphodiester or chimeric backbone or have a phosphorothioate backbone but be associated with a vehicle that delivers it directly into the cell. Such vehicles are known in the art and include, for example, liposomes and gene guns.

In another preferred embodiment the CpG oligonucleotide has the sequence $5'TCN_1TX_1X_2CGX_3X_43'$.

Preferably the CpG oligonucleotides of the invention include $X_1X_2$ selected from the group consisting of GpT, GpG, GpA and ApA and $X_3X_4$ is selected from the group consisting of TpT, CpT and TpC. For facilitating uptake into cells, CpG containing oligonucleotides are preferably in the range of 8 to 30 bases in length. However, nucleic acids of any size greater than 8 nucleotides (even many kb long) are capable of inducing an immune response according to the invention if sufficient immunostimulatory motifs are present, since larger nucleic acids are degraded into oligonucleotides inside of cells. Preferred synthetic oligonucleotides do not include a CCGG or CGCG quadmer or more than one CCG or CGG trimer at or near the 5' and/or 3' terminals. Stabilized oligonucleotides, where the oligonucleotide incorporates a phosphate backbone modification, as discussed in more detail below are also preferred. The modification may be, for example, a phosphorothioate or phosphorodithioate modification. Preferably, the phosphate backbone modification occurs at the 5' end of the nucleic acid for example, at the first two nucleotides of the 5' end of the oligonucleotide. Further, the phosphate backbone modification may occur at the 3' end of the nucleic acid for example, at the last five nucleotides of the 3' end of the nucleic acid. Alternatively the oligonucleotide may be completely or partially modified.

Preferably the CpG oligonucleotide is in the range of between 8 and 100 and more preferably between 8 and 30 nucleotides in size. Alternatively, CpG oligonucleotides can be produced on a large scale in plasmids and degraded into oligonucleotides.

The CpG oligonucleotide may be directly administered to the subject or may be administered in conjunction with a nucleic acid delivery complex. A "nucleic acid delivery complex" shall mean a nucleic acid molecule associated with (e.g. ionically or covalently bound to; or encapsulated within) a targeting means (e.g. a molecule that results in higher affinity binding to target cell (e.g. dendritic cell surfaces and/or increased cellular uptake by target cells). Examples of nucleic acid delivery complexes include nucleic acids associated with: a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

Delivery vehicles for delivering antigen to mucosal surfaces have been described. The CpG oligonucleotide and/or the antigen may be administered alone (e.g. in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., Salmonella, Escherichia coli, Bacillus calmatte-guerin, Shigella, Lactobacillus) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art and some additional examples are provided below in the discussion of vectors.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double-stranded structures. In one embodiment the CpG oligonucleotide contains a palindromic sequence. A palindromic sequence used in this context refers to a palindrome in which the CpG is part of the palindrome, and preferably is the center of the palindrome. In another embodiment the CpG oligonucleotide is free of a palindrome. A CpG oligonucleotide that is free of a palindrome is one in which the CpG dinucleotide is not part of a palindrome. Such an oligonucleotide may include a palindrome in which the CpG is not part of the palindrome.

A "stabilized nucleic acid molecule" shall mean a nucleic acid molecule that is relatively resistant to in vivo degradation (e.g. via an exo- or endo-nuclease). Stabilization can be a function of length or secondary structure. Unmethylated CpG oligonucleotides that are tens to hundreds of kbs long are relatively resistant to in vivo degradation. For shorter CpG oligonucleotides, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Preferred stabilized oligonucleotides of the instant invention have a modified backbone. It has been demonstrated that modification of the oligonucleotide backbone provides enhanced activity of the CpG oligonucleotides when administered in vivo. CpG constructs, including at least two phosphorothioate linkages at the 5' end of the oligonucleotide in multiple phosphorothioate linkages at the 3' end, preferably 5, provides maximal activity and protected the oligonucleotide from degradation by intracellular exo- and endo-nucleases. Other modified oligonucleotides include phosphodiester modified oligonucleotide, combinations of phosphodiester and phosphorothioate oligonucleotide, methylphosphonate, methylphosphorothioate, phosphorodithioate, and combinations thereof. Each of these combinations and their particular effects on immune cells is discussed in more detail in PCT Published Patent Applications claiming priority to U.S. Ser. Nos. 08/738,652 and 08/960,774, filed on Oct. 30, 1996 and Oct. 30, 1997 respectively, the entire contents of which is hereby incorporated by reference. It is believed that these modified oligonucleotides may show more stimulatory activity due to enhanced nuclease resistance, increased cellular uptake, increased protein binding, and/or altered intracellular localization.

Both phosphorothioate and phosphodiester oligonucleotides containing CpG motifs are active in immune cells. However, based on the concentration needed to induce CpG specific effects, the nuclease resistant phosphorothioate backbone CpG oligonucleotides are more potent (2 μg/ml for the phosphorothioate vs. a total of 90 μg/ml for phosphodiester).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

The nucleic acid sequences of the invention which are useful as mucosal adjuvants are those broadly described above and disclosed in PCT Published Patent Applications claiming priority to U.S. Ser. Nos. 08/738,652 and 08/960,774, filed on Oct. 30, 1996 and Oct. 30, 1997 respectively. Exemplary sequences include but are not limited to those immunostimulatory sequences shown in Table 1.

TABLE 1

| sequences | |
|---|---|
| GCTAGACGTTAGCGT; | (SEQ ID NO: 1) |
| GCTAGATGTTAGCGT; | (SEQ ID NO: 2) |
| GCTAGACGTTAGCGT; | (SEQ ID NO: 3) |
| GCTAGACGTTAGCGT; | (SEQ ID NO: 4) |
| GCATGACGTTGAGCT; | (SEQ ID NO: 5) |
| ATGGAAGGTCCAGCGTTCTC; | (SEQ ID NO: 6) |
| ATCGACTCTCGAGCGTTCTC; | (SEQ ID NO: 7) |
| ATCGACTCTCGAGCGTTCTC; | (SEQ ID NO: 8) |
| ATCGACTCTCGAGCGTTCTC; | (SEQ ID NO: 9) |
| ATGGAAGGTCCAACGTTCTC; | (SEQ ID NO: 10) |
| GAGAACGCTGGACCTTCCAT; | (SEQ ID NO: 11) |
| GAGAACGCTCGACCTTCCAT; | (SEQ ID NO: 12) |
| GAGAACGCTCGACCTTCGAT; | (SEQ ID NO: 13) |
| GAGAACGCTGGACCTTCCAT; | (SEQ ID NO: 14) |
| GAGAACGATGGACCTTCCAT; | (SEQ ID NO: 15) |
| GAGAACGCTCCAGCACTGAT; | (SEQ ID NO: 16) |
| TCCATGTCGGTCCTGATGCT; | (SEQ ID NO: 17) |
| TCCATGTCGGTCCTGATGCT; | (SEQ ID NO: 18) |
| TCCATGACGTTCCTGATGCT; | (SEQ ID NO: 19) |
| TCCATGTCGGTCCTGCTGAT; | (SEQ ID NO: 20) |
| TCAACGTT; | (SEQ ID NO: 21) |
| TCAGCGCT; | (SEQ ID NO: 22) |
| TCATCGAT; | (SEQ ID NO: 23) |
| TCTTCGAA; | (SEQ ID NO: 24) |
| CAACGTT; | (SEQ ID NO: 25) |
| CCAACGTT; | (SEQ ID NO: 26) |
| AACGTTCT; | (SEQ ID NO: 27) |
| TCAACGTC; | (SEQ ID NO: 28) |
| ATGGACTCTCCAGCGTTCTC; | (SEQ ID NO: 29) |
| ATGGAAGGTCCAACGTTCTC; | (SEQ ID NO: 30) |
| ATCGACTCTCGAGCGTTCTC; | (SEQ ID NO: 31) |
| ATGGAGGCTCCATCGTTCTC; | (SEQ ID NO: 32) |
| ATCGACTCTCGAGCGTTCTC; | (SEQ ID NO: 33) |
| ATCGACTCTCGAGCGTTCTC; | (SEQ ID NO: 34) |
| TCCATGTCGGTCCTGATGCT; | (SEQ ID NO: 35) |
| TCCATGCCGGTCCTGATGCT; | (SEQ ID NO: 36) |
| TCCATGGCGGTCCTGATGCT; | (SEQ ID NO: 37) |
| TCCATGACGGTCCTGATGCT; | (SEQ ID NO: 38) |
| TCCATGTCGATCCTGATGCT; | (SEQ ID NO: 39) |
| TCCATGTCGCTCCTGATGCT; | (SEQ ID NO: 40) |
| TCCATGTCGTCCTGATGCT; | (SEQ ID NO: 41) |
| TCCATGACGTGCCTGATGCT; | (SEQ ID NO: 42) |
| TCCATAACGTTCCTGATGCT; | (SEQ ID NO: 43) |
| TCCATGACGTCCCTGATGCT; | (SEQ ID NO: 44) |
| TCCATCACGTGCCTGATGCT; | (SEQ ID NO: 45) |
| GGGGTCAACGTTGACGGGG; | (SEQ ID NO: 46) |
| GGGGTCAGTCGTGACGGGG; | (SEQ ID NO: 47) |
| GCTAGACGTTAGTGT; | (SEQ ID NO: 48) |
| TCCATGTCGTTCCTGATGCT; | (SEQ ID NO: 49) |
| ACCATGGACGATCTGTTTCCCCTC; | (SEQ ID NO: 50) |
| TCTCCCAGCGTGCGCCAT; | (SEQ ID NO: 51) |
| ACCATGGACGAACTGTTTCCCCTC; | (SEQ ID NO: 52) |
| ACCATGGACGAGCTGTTTCCCCTC; | (SEQ ID NO: 53) |
| ACCATGGACGACCTGTTTCCCCTC; | (SEQ ID NO: 54) |
| ACCATGGACGTACTGTTTCCCCTC; | (SEQ ID NO: 55) |
| ACCATGGACGGTCTGTTTCCCCTC; | (SEQ ID NO: 56) |
| ACCATGGACGTTCTGTTTCCCCTC; | (SEQ ID NO: 57) |
| CACGTTGAGGGGCAT; | (SEQ ID NO: 58) |
| TCAGCGTGCGCC; | (SEQ ID NO: 59) |
| ATGACGTTCCTGACGTT; | (SEQ ID NO: 60) |
| TCTCCCAGCGGGCGCAT; | (SEQ ID NO: 61) |
| TCCATGTCGTTCCTGTCGTT; | (SEQ ID NO: 62) |
| TCCATAGCGTTCCTAGCGTT; | (SEQ ID NO: 63) |
| TCGTCGCTGTCTCCCCTTCTT; | (SEQ ID NO: 64) |
| TCCTGACGTTCCTGACGTT; | (SEQ ID NO: 65) |
| TCCTGTCGTTCCTGTCGTT; | (SEQ ID NO: 66) |
| TCCATGTCGTTTTTGTCGTT; | (SEQ ID NO: 67) |
| TCCTGTCGTTCCTTGTCGTT; | (SEQ ID NO: 68) |
| TCCTTGTCGTTCCTGTCGTT; | (SEQ ID NO: 69) |
| TCCTGTCGTTTTTTGTCGTT; | (SEQ ID NO: 70) |

TABLE 1-continued

| sequences | |
|---|---|
| TCGTCGCTGTCTGCCCTTCTT; | (SEQ ID NO: 71) |
| TCGTCGCTGTTGTCGTTTCTT; | (SEQ ID NO: 72) |
| TCCATGCGTGCGTGCGTTTT; | (SEQ ID NO: 73) |
| TCCATGCGTTGCGTTGCGTT; | (SEQ ID NO: 74) |
| TCCACGACGTTTTCGACGTT; | (SEQ ID NO: 75) |
| TCGTCGTTGTCGTTGTCGTT; | (SEQ ID NO: 76) |
| TCGTCGTTTTGTCGTTTTGTCGTT; | (SEQ ID NO: 77) |
| TCGTCGTTGTCGTTTTGTCGTT; | (SEQ ID NO: 78) |
| GCGTGCGTTGTCGTTGTCGTT; | (SEQ ID NO: 79) |
| TGTCGTTTGTCGTTGTCGTT; | (SEQ ID NO: 80) |
| TGTCGTTGTCGTTGTCGTTGTCGTT; | (SEQ ID NO: 81) |
| TGTCGTTGTCGTTGTCGTT; | (SEQ ID NO: 82) |
| TCGTCGTCGTCGTT; | (SEQ ID NO: 83) |
| TGTCGTTGTCGTT; | (SEQ ID NO: 84) |
| TCCATAGCGTTCCTAGCGTT; | (SEQ ID NO: 85) |
| TCCATGACGTTCCTGACGTT; | (SEQ ID NO: 86) |
| GTCGYT; | (SEQ ID NO: 87) |
| TGTCGYT; | (SEQ ID NO: 88) |
| AGCTATGACGTTCCAAGG; | (SEQ ID NO: 89) |
| TCCATGACGTTCCTGACGTT; | (SEQ ID NO: 90) |
| ATCGACTCTCGAACGTTCTC; | (SEQ ID NO: 92) |
| TCCATGTCGGTCCTGACGCA; | (SEQ ID NO: 93) |
| TCTTCGAT; | (SEQ ID NO: 94) |
| ATAGGAGGTCCAACGTTCTC; | (SEQ ID NO: 95) |

The stimulation index of a particular immunostimulatory CpG DNA can be tested in various immune cell assays. Preferably, the stimulation index of the CpG oligonucleotide with regard to B cell proliferation is at least about 5, preferably at least about 10, more preferably at least about 15 and most preferably at least about 20 as determined by incorporation of $^3$H uridine in a murine B cell culture, which has been contacted with 20 μM of oligonucleotide for 20 h at 37° C. and has been pulsed with 1 μCi of $^3$H uridine; and harvested and counted 4 h later as described in detail in PCT Published Patent Applications claiming priority to U.S. Ser. Nos. 08/738,652 and 08/960,774, filed on Oct. 30, 1996 and Oct. 30, 1997 respectively. For use in vivo, for example, it is important that the CpG oligonucleotide be capable of effectively inducing IgA expression.

The CpG oligonucleotide can be administered in conjunction with another mucosal adjuvant. It was discovered according to the invention that the combination of a CpG oligonucleotide and a mucosal adjuvant produced a synergistic immune response. When the CpG oligonucleotide is administered in conjunction with another adjuvant, the CpG oligonucleotide can be administered before, after, and/or simultaneously with the other mucosal adjuvant. For instance, the CpG oligonucleotide may be administered with a priming dose of antigen. Either or both of the adjuvants may then be administered with the boost dose. Alternatively, the CpG oligonucleotide may be administered with a boost dose of antigen. Either or both of the adjuvants may then be administered with the prime dose.

Additionally it has been discovered that mucosal immunity can be induced as long as one of the dosages of CpG oligonucleotide is administered to a mucosal surface. Other doses can be administered systemically or mucosally without affecting the induction of the immune response. For example, the subject may be primed by mucosal delivery of antigen and CpG oligonucleotide, with or without other mucosal adjuvants and boosted by a parenteral (e.g., intramuscular, intradermal or subcutaneous) route of delivery of antigen alone, with CpG oligonucleotides, with a non-oligonucleotide adjuvant or a combination of adjuvants that may or may not include CpG oligonucleotide. Alternatively, the prime dose may be given parenterally and boosted mucosally using the invention. All of these approaches can induce strong systemic and mucosal immune responses. Thus the methods of the invention encompass the administration of at least one dose, either prime or boost or both, to the mucosal surface. The other doses of CpG oligonucleotide may be administered mucosally or systemically.

A "prime dose" is the first dose of antigen administered to the subject. In the case of a subject that has an infection the prime dose may be the initial exposure of the subject to the infectious microbe (passive exposure) and thus the subsequent purposeful administration of antigen (active exposure) with CpG oligonucleotide becomes the boost dose. A "boost dose" is a second or third, etc, dose of antigen administered to a subject that has already been exposed to the antigen. In some cases the prime dose administered with the CpG oligonucleotide is so effective that a boost dose is not required to protect a subject at risk of infection from being infected.

The subject is exposed to the antigen. As used herein, the term "exposed to" refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface. When a subject is passively exposed to an antigen it is preferred in some embodiments that the CpG oligonucleotide is an oligonucleotide of 8-100 nucleotides in length and/or has a phosphate modified backbone.

The methods in which a subject is passively exposed to an antigen can be particularly dependent on timing of CpG oligonucleotide. For instance, in a subject at risk of developing a cancer or an infectious disease or an allergic or asthmatic response, the subject may be administered the CpG oligonucleotide on a regular basis when that risk is greatest, i.e., during allergy season or after exposure to a cancer causing agent. Additionally the CpG oligonucleotide may be administered to travelers before they travel to foreign lands where they are at risk of exposure to infectious agents. Likewise the CpG oligonucleotide and may be administered to soldiers or civilians at risk of exposure to biowarfare to induce a mucosal immune response to the antigen when and if the subject is exposed to it.

An "antigen" as used herein is a molecule capable of provoking an immune response. Antigens include but are not limited to cells, cell extracts, proteins, polypeptides, peptides, polysaccharides, polysaccharide conjugates, peptide mimics of polysaccharides, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A "cancer antigen" as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include antigens that are recombinately an immunogenic portion of or a whole tumor or cancer. Such antigens can be isolated or prepared recombinately or by any other means known in the art.

A "microbial antigen" as used herein is an antigen of a microorganism and includes but is not limited to infectious virus, infectious bacteria, infectious parasites, and infectious fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of infectious virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps (e.g. *M. tuberculosis, M avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium* such as *Plasmodium falciparum, Plasmodium malariae, Plasmodium ovale,* and *Plasmodium vivax* and *Toxoplasma gondii.*

Other medically relevant microorganisms have been described extensively in the literature, e.g., see C. G. A Thomas, *Medical Microbiology,* Bailliere Tindall, Great Britain 1983, the entire contents of which is hereby incorporated by reference.

Although many of the microbial antigens described above relate to human disorders, the invention is also useful for treating other nonhuman vertebrates. Nonhuman vertebrates are also capable of developing infections which can be prevented or treated with the CpG oligonucleotides disclosed herein. For instance, in addition to the treatment of infectious human diseases, the methods of the invention are useful for treating infections of animals.

As used herein, the term "treat", "treated", or "treating" when used with respect to an infectious disease refers to a prophylactic treatment which increases the resistance of a subject (a subject at risk of infection) to infection with a pathogen or, in other words, decreases the likelihood that the subject will become infected with the pathogen as well as a treatment after the subject (a subject who has been infected) has become infected in order to fight the infection, e.g., reduce or eliminate the infection or prevent it from becoming worse.

Many vaccines for the treatment of non-human vertebrates are disclosed in Bennett, K. *Compendium of Veterinary Products,* 3rd ed. North American Compendiums, Inc., 1995. As discussed above, antigens include infectious microbes such as virus, bacteria and fungi and fragments thereof, derived from natural sources or synthetically. Infectious virus of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV).

The foamy viruses include human foamy virus (HFV), simian foamy virus (SFV) and bovine foamy virus (BFV).

Examples of other RNA viruses that are antigens in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, *Poliovirus muris*, Bovine enteroviruses, Porcine enteroviruses, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxyiridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In addition to the use of the CpG oligonucleotides to induce an antigen specific immune response in humans, the methods of the preferred embodiments are particularly well suited for treatment of birds such as hens, chickens, turkeys, ducks, geese, quail, and pheasant. Birds are prime targets for many types of infections.

Hatching birds are exposed to pathogenic microorganisms shortly after birth. Although these birds are initially protected against pathogens by maternal derived antibodies, this protection is only temporary, and the bird's own immature immune system must begin to protect the bird against the pathogens. It is often desirable to prevent infection in young birds when they are most susceptible. It is also desirable to prevent against infection in older birds, especially when the birds are housed in closed quarters, leading to the rapid spread of disease. Thus, it is desirable to administer the CpG oligonucleotide and the non-nucleic acid adjuvant of the invention to birds to enhance an antigen-specific immune response when antigen is present.

An example of a common infection in chickens is chicken infectious anemia virus (CIAV). CIAV was first isolated in Japan in 1979 during an investigation of a Marek's disease vaccination break (Yuasa et al., 1979, Avian Dis. 23:366-385). Since that time, CIAV has been detected in commercial poultry in all major poultry producing countries (van Bulow et al., 1991, pp. 690-699) in Diseases of Poultry, 9th edition, Iowa State University Press).

CIAV infection results in a clinical disease, characterized by anemia, hemorrhage and immunosuppression, in young susceptible chickens. Atrophy of the thymus and of the bone marrow and consistent lesions of CIAV-infected chickens are also characteristic of CIAV infection. Lymphocyte depletion in the thymus, and occasionally in the bursa of Fabricius, results in immunosuppression and increased susceptibility to secondary viral, bacterial, or fungal infections which then complicate the course of the disease. The immunosuppression may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, Avian Dis. 33:707-713). Chickens develop an age resistance to experimentally induced disease due to CAA. This is essentially complete by the age of 2 weeks, but older birds are still susceptible to infection (Yuasa, N. et al., 1979 supra; Yuasa, N. et al., Arian Diseases 24, 202-209, 1980). However, if chickens are dually infected with CAA and an immunosuppressive agent (IBDV, MDV etc.) age resistance against the disease is delayed (Yuasa, N. et al., 1979 and 1980 supra; Bulow von V. et al., J. Veterinary Medicine 33, 93-116, 1986). Characteristics of CIAV that may potentiate disease transmission include high resistance to environmental inactivation and some common disinfectants. The economic impact of CIAV infection on the poultry industry is clear from the fact that 10% to 30% of infected birds in disease outbreaks die.

Vaccination of birds, like other vertebrate animals can be performed at any age. Normally, vaccinations are performed at up to 12 weeks of age for a live microorganism and between 14-18 weeks for an inactivated microorganism or other type of vaccine. For in ovo vaccination, vaccination can be performed in the last quarter of embryo development. The vaccine may be administered subcutaneously, by spray, orally, intraocularly, intratracheally, nasally, or by other mucosal delivery methods described herein. Thus, the CpG oligonucleotide of the invention can be administered to birds and other non-human vertebrates using routine vaccination schedules and the antigen is administered after an appropriate time period as described herein.

Cattle and livestock are also susceptible to infection. Disease which affect these animals can produce severe economic losses, especially amongst cattle. The methods of the invention can be used to protect against infection in livestock, such as cows, horses, pigs, sheep, and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the *pestivirus* genus. Although, Pestiviruses were previously classified in the Togaviridae family, some studies have suggested their reclassification within the Flaviviridae family along with the flavivirus and hepatitis C virus (HCV) groups (Francki, et al., 1991).

BVDV, which is an important pathogen of cattle can be distinguished, based on cell culture analysis, into cytopathogenic (CP) and noncytopathogenic (NCP) biotypes. The NCP biotype is more widespread although both biotypes can be found in cattle. If a pregnant cow becomes infected with an NCP strain, the cow can give birth to a persistently infected and specifically immunotolerant calf that will spread virus during its lifetime. The persistently infected cattle can succumb to mucosal disease and both biotypes can then be isolated from the animal. Clinical manifestations can include abortion, teratogenesis, and respiratory problems, mucosal disease and mild diarrhea. In addition, severe thrombocytopenia, associated with herd epidemics, that may result in the death of the animal has been described and strains associated with this disease seem more virulent than the classical BVDVs.

Equine herpesviruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Primary infection of upper respiratory tract of young horses results in a febrile illness which lasts for 8 to 10 days. Immunologically experienced mares may be reinfected via the respiratory tract without disease becoming apparent, so that abortion usually occurs without warning. The neurological syndrome is associated with respiratory disease or abortion and can affect animals of either sex at any age, leading to incoordination, weakness and posterior paralysis (Telford, E. A. R. et al., Virology 189, 304-316, 1992). Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al. (1990) Lancet 36:1538-1541; Desrosiers et al. PNAS USA (1989) 86:6353-6357; Murphey-Corb et al. (1989) Science 246:1293-1297; and Carlson et al. (1990) AIDS Res. Human Retroviruses 6:1239-1246). A recombinant HIV gp120 vaccine has been reported to afford protection in chimpanzees (Berman et al. (1990) Nature 345:622-625).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to protect them against infection.

Domestic cats may become infected with several retroviruses, including but not limited to feline leukemia virus (FeLV), feline sarcoma virus (FeSV), endogenous type C oncornavirus (RD-114), and feline syncytia-forming virus (FeSFV). Of these, FeLV is the most significant pathogen, causing diverse symptoms, including lymphoreticular and myeloid neoplasms, anemias, immune mediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (also referred to as feline immunodeficiency) was first reported in Pedersen et al. (1987) Science 235:790-793. Characteristics of FIV have been reported in Yamamoto et al. (1988) Leukemia, December Supplement 2:204 S-215S; Yamamoto et al. (1988) Am. J. Vet. Res. 49:1246-1258; and Ackley et al. (1990) J. Virol. 64:5652-5655. Cloning and sequence analysis of FIV have been reported in Olmsted et al. (1989) Proc. Natl. Acad. Sci. USA 86:2448-2452 and 86:4355-4360.

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old.

Viral, bacterial, and parasitic diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations are described in U.S. Pat. No. 5,780,448 issued to Davis.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered by immersion or orally.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Polypeptides of viral aquaculture pathogens include but are not limited to glycoprotein (G) or nucleoprotein (N) of viral hemorrhagic septicemia virus (VHSV); G or N proteins of infectious hematopoietic necrosis virus (1HNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Polypeptides of bacterial pathogens include but are not limited to an iron-regulated outer membrane protein, (TROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (TROMP), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of *Rickettsia*.

Polypeptides of a parasitic pathogen include but are not limited to the surface antigens of *Ichthyophthirius*.

An "allergen" refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The antigen may be an antigen that is encoded by a nucleic acid vector or it may be not encoded in a nucleic acid vector. In the former case the nucleic acid vector is administered to the subject and the antigen is expressed in vivo. In the latter case the antigen is administered directly to the subject. An "antigen not encoded in a nucleic acid vector" as used herein refers to any type of antigen that is not a nucleic acid. For instance, in some aspects of the invention the antigen not encoded in a nucleic acid vector is a polypeptide. Minor modifications of the primary amino acid sequences of polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The polypeptide may be, for example, a viral polypeptide. One non-limiting example of an antigen useful according to the invention is the hepatitis B surface antigen. Experiments using this antigen are described in the Examples below.

The term "substantially purified" as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis.

The invention also utilizes polynucleotides encoding the antigenic polypeptides. It is envisioned that the antigen may be delivered to the subject in a nucleic acid molecule which encodes for the antigen such that the antigen must be expressed in vivo. Such antigens delivered to the subject in a nucleic acid vector are referred to as "antigens encoded by a nucleic acid vector." The nucleic acid encoding the antigen is operatively linked to a gene expression sequence which directs the expression of the antigen nucleic acid within a eukaryotic cell. The "gene expression sequence" is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be "operably linked" when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid of the invention may be delivered to the immune system alone or in association with a vector. In its broadest sense, a "vector" is any vehicle capable of facilitating the transfer of the antigen nucleic acid to the cells of the immune system so that the antigen can be expressed and presented on the surface of the immune cell. The vector generally transports the nucleic acid to the immune cells with reduced degradation relative to the extent of degradation that would result in the absence of the vector. The vector optionally includes the above-described gene expression sequence to enhance expression of the antigen nucleic acid in immune cells. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

A preferred virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to immune cells, e.g. dendritic cells, probably by passing through the gut barrier. High levels of immune protection have been established using this methodology. Such methods of delivery are useful for the aspects of the invention utilizing systemic delivery of antigen, CpG oligonucleotide and/or hormone.

CpG oligonucleotide can act in a synergistic manner with other mucosal adjuvants to enhance immune responses. The CpG oligonucleotide and mucosal adjuvant may be administered simultaneously or sequentially. When the adjuvants are administered simultaneously they can be administered in the same or separate formulations, but are administered at the same time. The adjuvants are administered sequentially, when the administration of the at least two adjuvants is temporally separated. The separation in time between the administration of the two adjuvants may be a matter of minutes or it may be longer.

Figure 2:
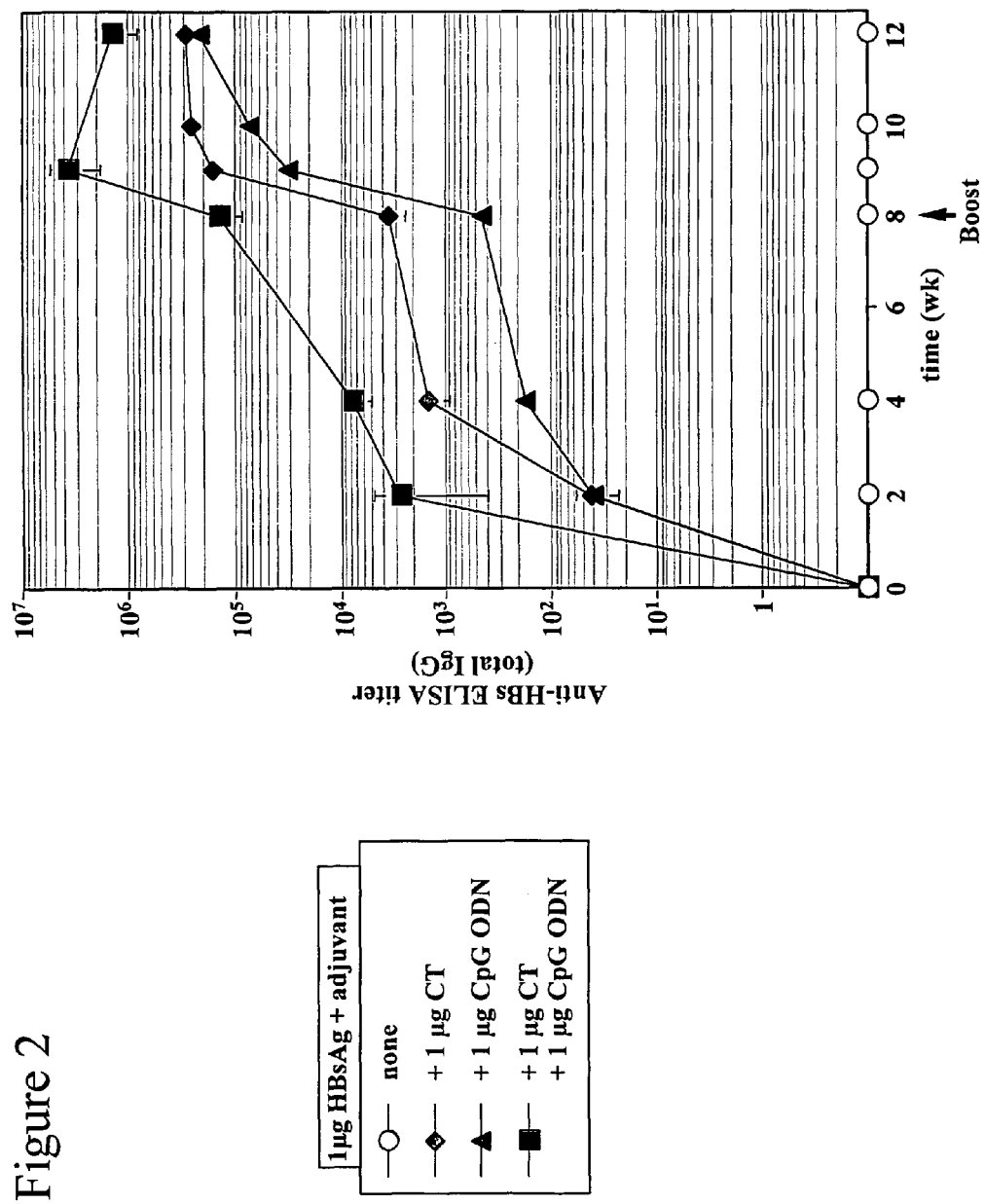
FIG. 2 is a graph depicting the effect of different adjuvants on total IgG titers of anti-Hbs, wherein BALB/c mice were immunized by IN inhalation with HBsAg (1 μg) without or in combination with Cholera toxin (CT) and/or CpG oligonucleotide (motif #1826, SEQ ID NO. 90) adjuvants and at 8 weeks mice were boosted in the same manner as prime.
Figure 3:
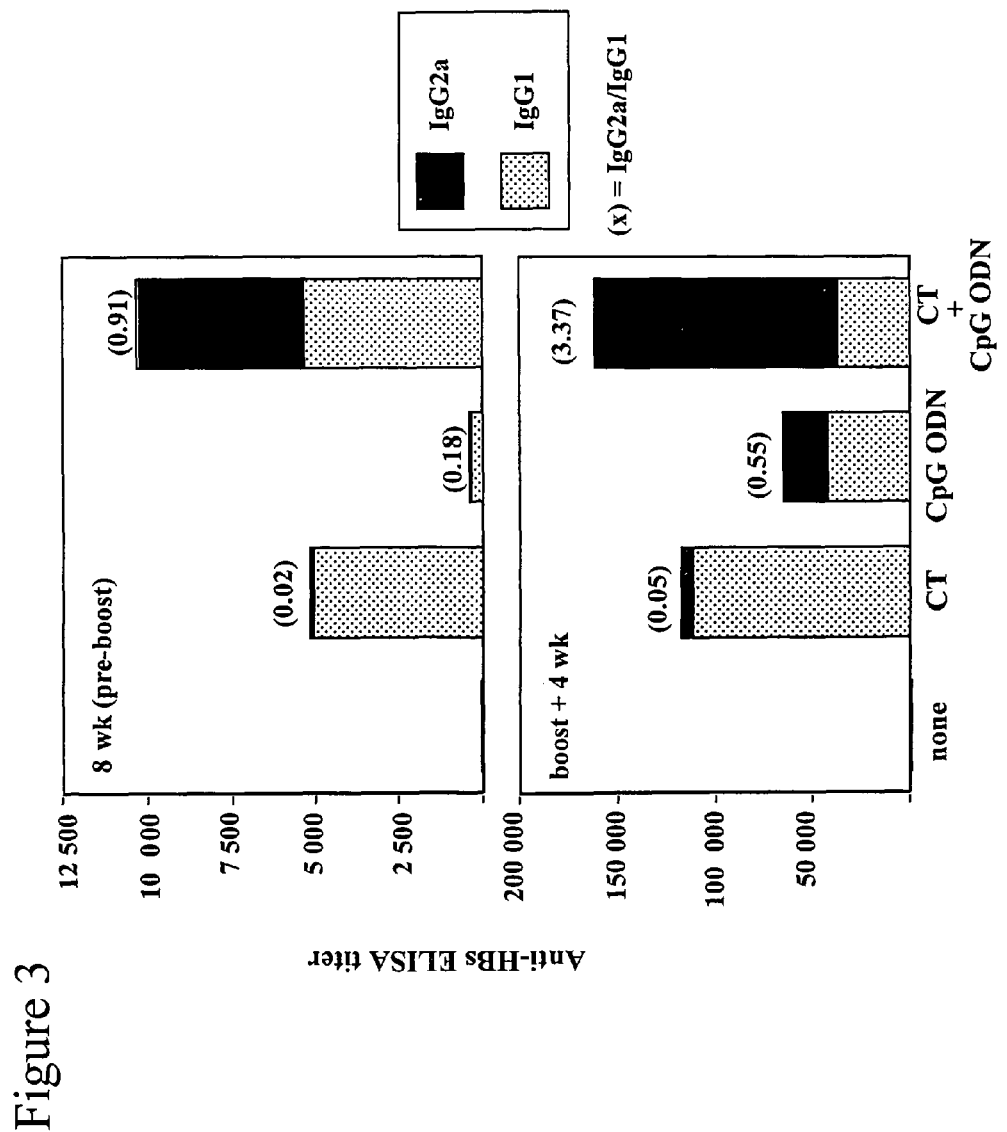
FIG. 3 is a bar graph depicting the effect of different adjuvants on anti-HBs IgG isotype, wherein BALB/c mice were immunized by IN inhalation with HBsAg (1 μg) without or in combination with Cholera toxin (CT) and/or CpG oligonucleotide (motif #1826, SEQ ID NO. 90) adjuvants (1 μg) and at 8 weeks mice were boosted in the same manner as prime.

As shown in the Examples section, titers of serum anti-HBs IgG, which is associated with systemic immunity, in mice immunized with CpG oligonucleotide plus CT were at least 50-fold higher than with CT or CpG oligonucleotide alone (FIG. 1). Furthermore, titers with 1 µg of the two adjuvants together gave better results than 10 µg of either adjuvant alone. These results indicate a synergistic action of the two adjuvants. Similar results were also obtained with CpG and LT. Such synergy was seen for both humoral (FIGS. 1-3) and cell-mediated (CTL and T-cell proliferation) (FIG. 4) responses. As well, the proportion of IgG2a isotype of antibodies, was about 10-times greater with CpG ODN than CT, indicating a greater Th1 influence of CpG ODN compared to CT. Furthermore, the combination of CpG ODN and CT gave a 50-times higher IgG2a:IgG1 ratio than CT alone. Taken together, these results indicate a strong synergy of the adjuvant combination humoral immune responses, with respect to both strength and Th1-bias, and cellular immune responses (FIG. 3).

Figure 5:
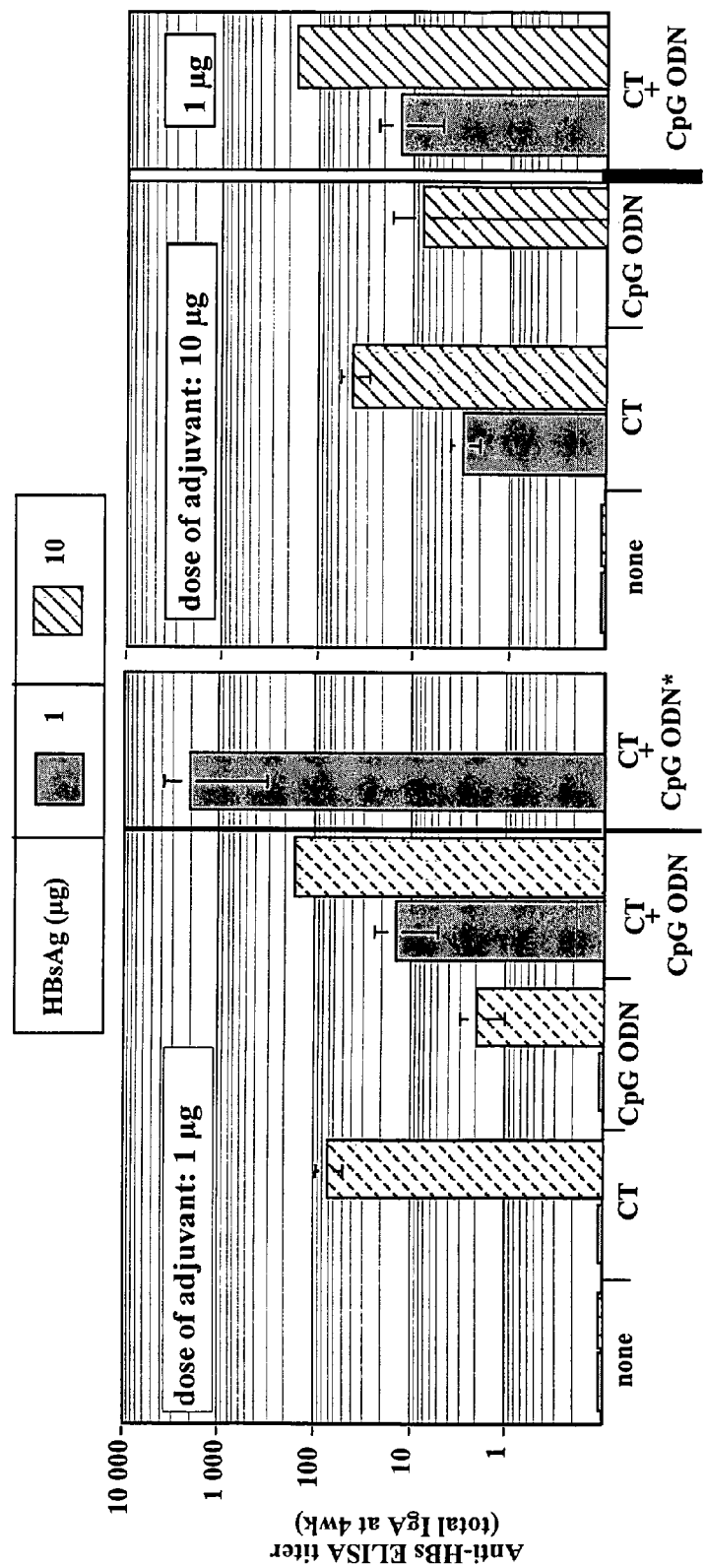
FIG. 5 is a bar graph depicting the effect of different adjuvants on anti-HBs IgA titers in lung washes, wherein BALB/c mice were immunized by IN inhalation with HBsAg (1 or 10 µg) without or in combination with Cholera toxin (CT) and/or CpG oligonucleotide (motif #1826, SEQ ID NO. 90) adjuvants at different doses (1 or 10 µg) and four weeks after immunization (or after boost for group marked by *) mice were killed by Halothane overdose and lungs were washed with 1 ml TBS.
Figure 6:
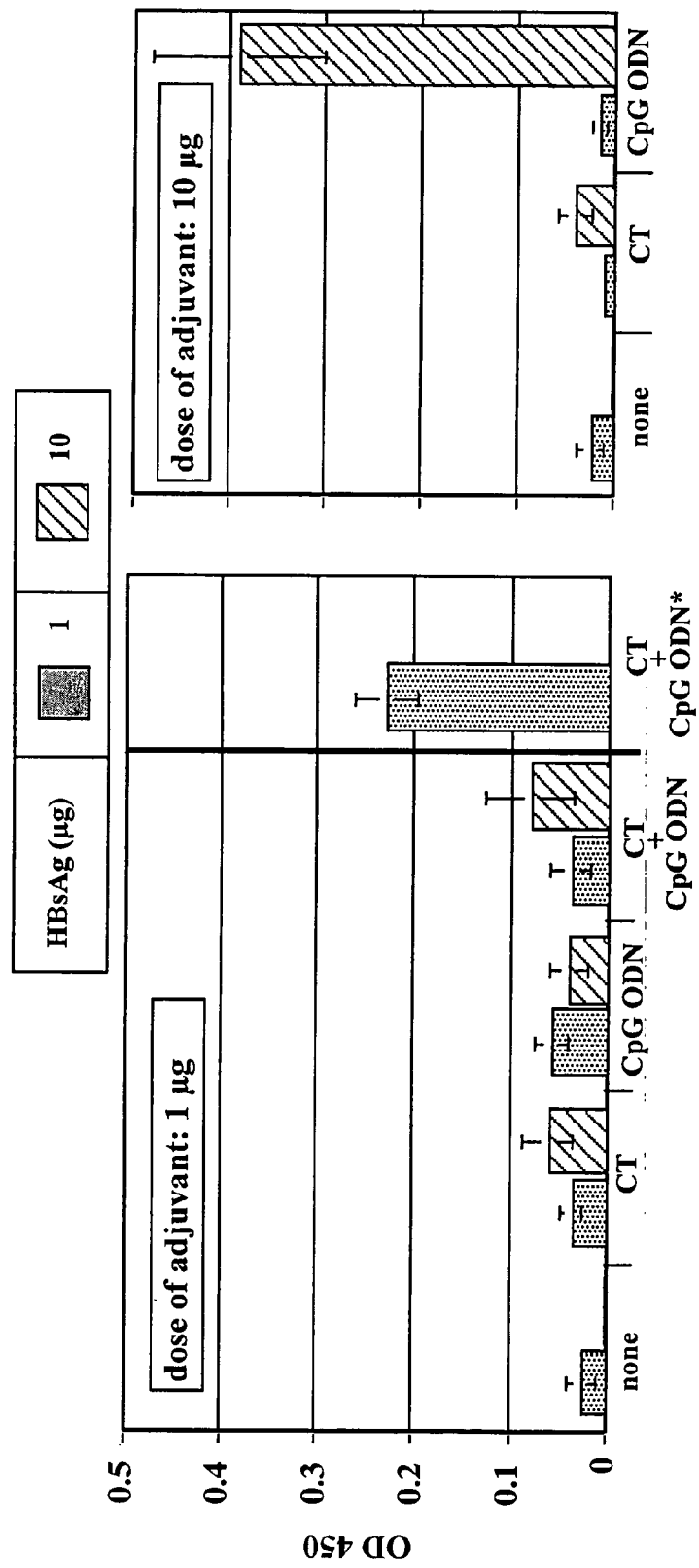
FIG. 6 is a bar graph depicting the effect of different adjuvants on anti-HBs IgA titers in fecal pellet solutions, wherein BALB/c mice were immunized by IN inhalation with HBsAg (1 or 10 µg) without or in combination with Cholera toxin (CT) and/or CpG oligonucleotide (motif #1826, SEQ ID NO. 90) at different doses (1 or 10 µg) and four weeks after immunization (or after boost for group marked by *) mice were isolated for 24 hr and fecal pellets were collected and resuspended in TBS at 0.1 mg/ml.

The hallmark of mucosal immunity is the presence of secretory IgA antibodies in association with mucosal surfaces. IgA antibodies are essential to prevent entry of the pathogen into the body. IN immunization of mice with HBsAg alone, 1 or 10 µg, failed to induce any detectable IgA in lung washes. Nor was there any IgA with the low dose of antigen and a low dose (1 µg) of CT or CpG ODN. However there was significant IgA with a high dose of antigen and low dose of either CT or CpG ODN or a low dose of antigen and a low dose of combined adjuvants. In fact, IgA levels with 1 µg of each of CpG ODN and CT combined were higher than with 10 µg of either alone, when administered with 10 µg HBsAg (FIG. 5). Furthermore, IgA in fecal extracts, which indicates induction of mucosal immunity at distant sites, was detected only with the combined adjvuants (FIG. 6). These results indicate that CpG ODN is a potent adjuvant for induction of mucosal immunity and that there is a strong synergistic response when used with another mucosal adjuvant such as CT.

Figure 7:
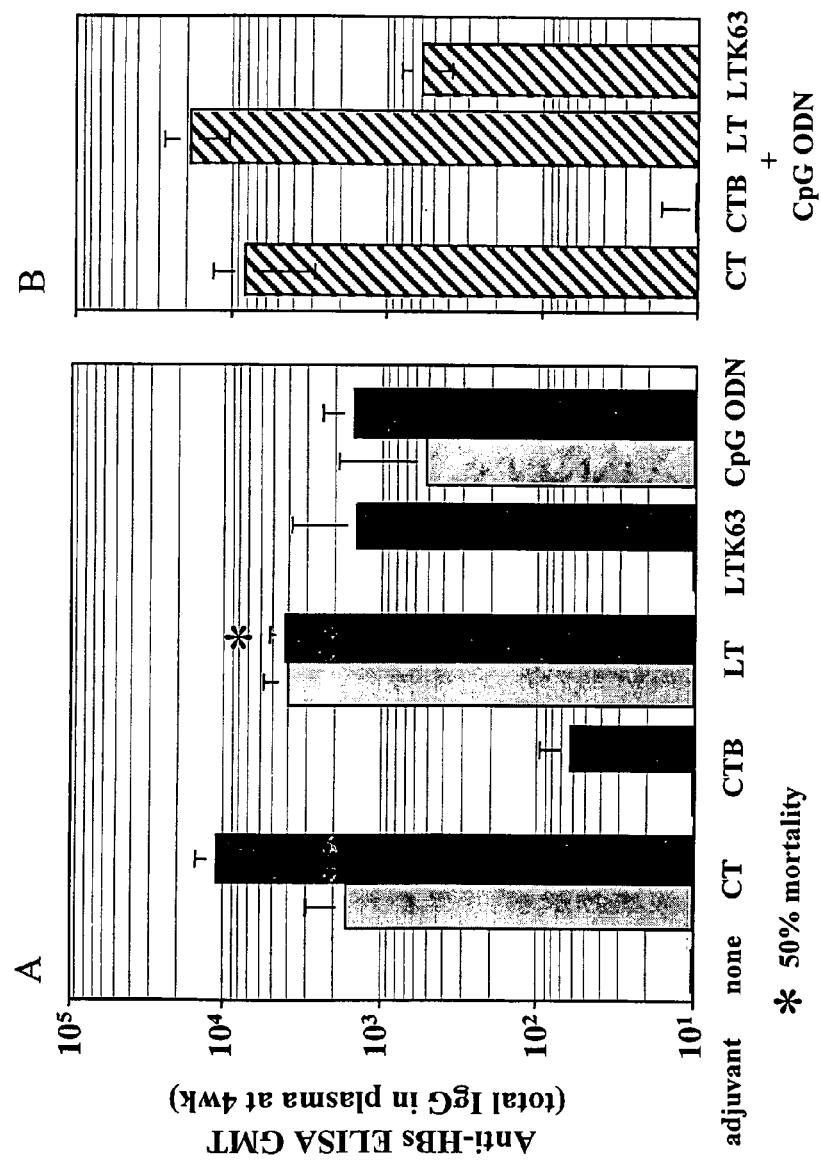
FIG. 7 is a graph depicting the effect of different adjuvants on total IgG titers of anti-HBs, wherein BALB/c mice were immunized by IN inhalation with HBsAg (1 µg) without or in combination with Cholera toxin (CT), *Escherichia coli* heat-labile enterotoxin (LT), the B subunit of Cholera toxin (CTB), a detoxified mutant of *Escherichia coli* heat-labile enterotoxin (LTK63), CpG oligonucleotide (motif #1826, SEQ ID NO. 90) or non-CpG control oligonucleotide (motif #1982, SEQ ID NO. 91) as adjuvants (1, 10 or 500 µg). In groups which responded, all mice gave titers >10, except in the case of 10 µg LT where only ⅕ mice responded.

Similar results were found when LT was used in place of CT (FIG. 7, Tables 2 and 3). CT and LT, which are closely related with considerable structural and functional homology, are both too toxic for use in humans. However there are a number of derivations of CT and LT that retain some adjuvant activity yet are much less toxic. One example is the B-subunit of CT (CTB) which is non-toxic since the toxicity is associated with the A subunit. Another example is LTK63, a genetically detoxified mutant of LT with no toxic enzymatic activity. Although these adjuvants are being used in human clinical trials, neither was a strong as CpG ODN for induction of systemic immunity (serum IgG) when each was used at 1 µg (FIG. 7). There was also a synergistic effect when CpG ODN and CTB or LTK63 were used together, however this was more noticeable for Th1-bias than for strength of the antibody response (FIG. 7 and Table 2). The combination of CpG ODN and LTK63 also induced IgA in lung washes, even though neither adjuvant on its own induced IgA at low concentrations (Table 3).

The strong adjuvanticity and low toxicity of CpG oligonucleotide when delivered to a mucosal surface has important implications. It will allow many antigens to be delivered to mucosal surfaces for the induction of strong systemic immune responses. Non-invasive vaccine delivery is desirable for immunization of children, animals, mass vaccination programs and also to avoid the risk of needle-stick injury. Such vaccines could be delivered intranasally by nose-drops or nasal spray or with a delivery system, or they could be delivered by other routes (oral, rectal, ocular) to other mucosal surfaces, including with different delivery systems.

The synergistic interaction of CpG oligonucleotide with mucosal adjuvants has important implications in vaccine development. Because of the synergistic response it is now possible to use lower and less toxic doses of mucosal adjuvants such as CT, or other related toxins or subunits thereof, in conjunction with CpG oligonucleotide to obtain even better immune responses with less toxicity. For example, it would be possible to use CpG oligonucleotide in combination with a less toxic genetically modified mutants of CT or LT, for a highly effective vaccine of acceptable toxicity. Not only could the combined adjuvant approach be used to advantage with different toxins, but also with different forms of antigen, and different delivery systems to various mucosal routes. An effective amount as used with respect to this aspect of the invention is an amount that produces a synergistic immune response. A synergistic amount is that amount which produces an immune response against a specific antigen that is greater than the sum of the individual effects of either the CpG or the mucosal adjuvant alone.

Figure 8:
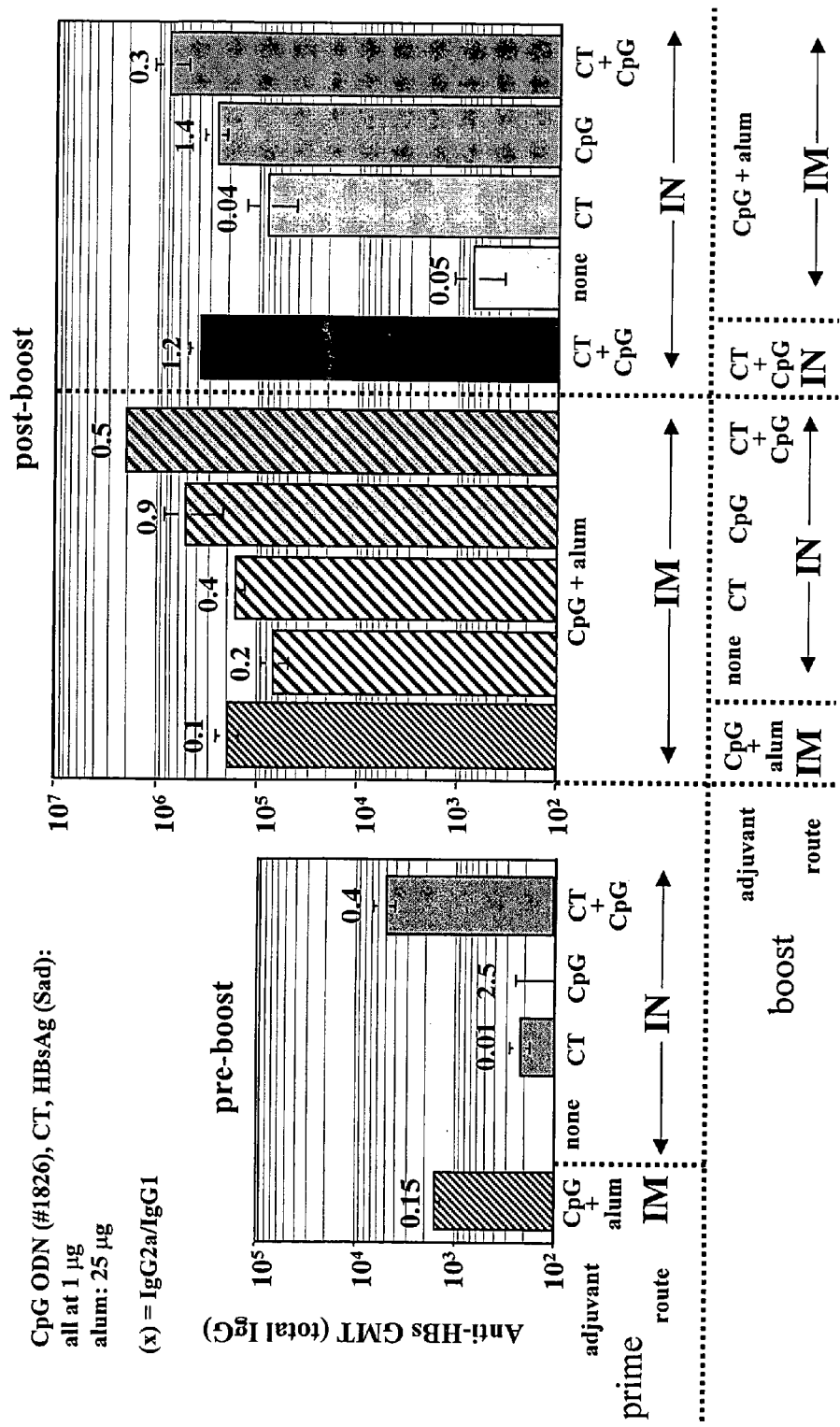
FIG. 8 is a bar graph depicting the effect of different prime/boost strategies on total IgG titers of anti-HBs, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90); or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90). Numbers at the top of each bar represent the IgGa/IgG1 ratio.
Figure 9:
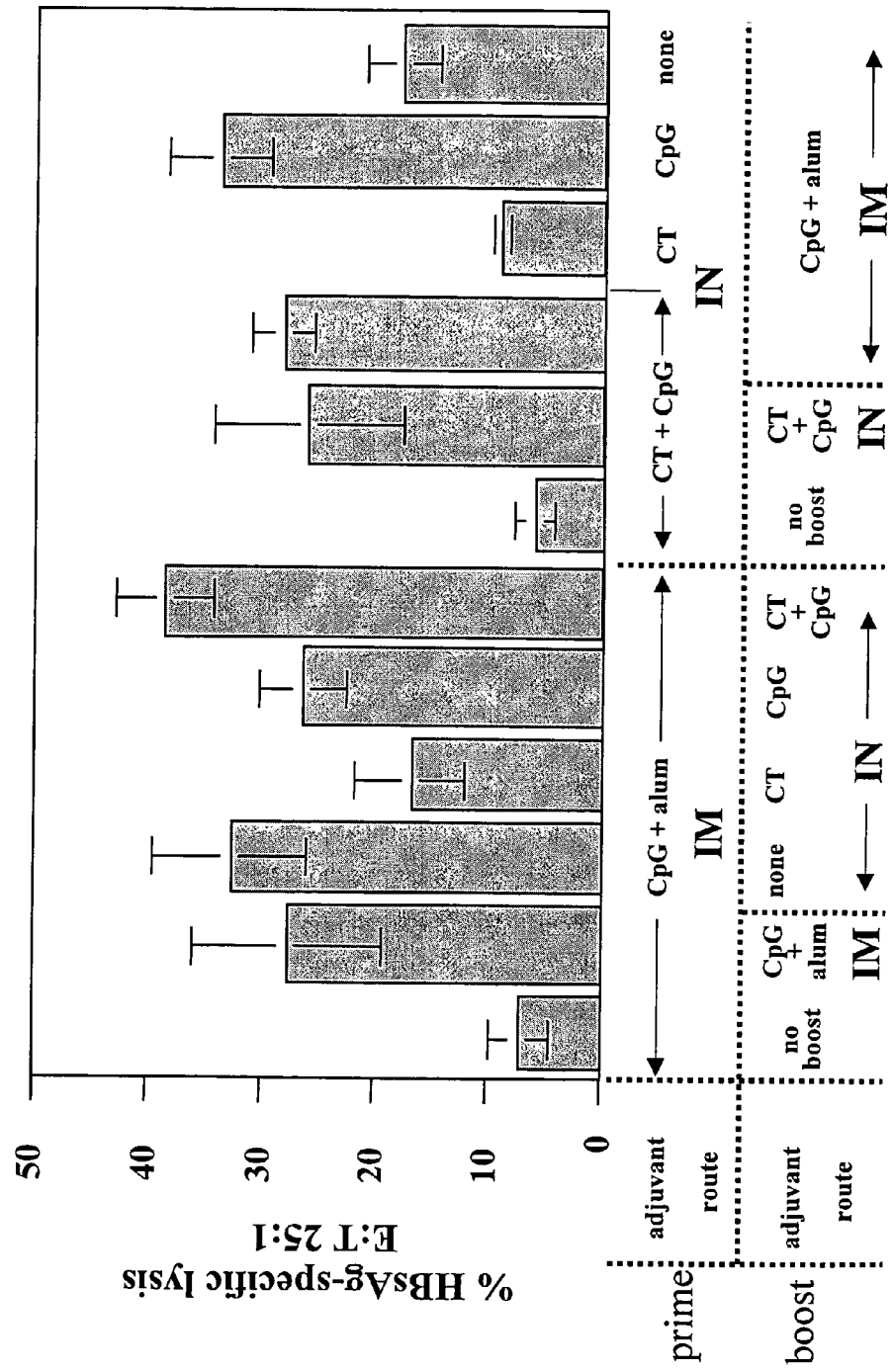
FIG. 9 is a bar graph depicting the effect of different prime/boost strategies with different adjuvants on HBsAg specific CTL response, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90), or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90), and 4 weeks after boost mice were killed by Halothane overdose, splenocytes isolated and HBsAg specific CTL activity measured.
Figure 10:
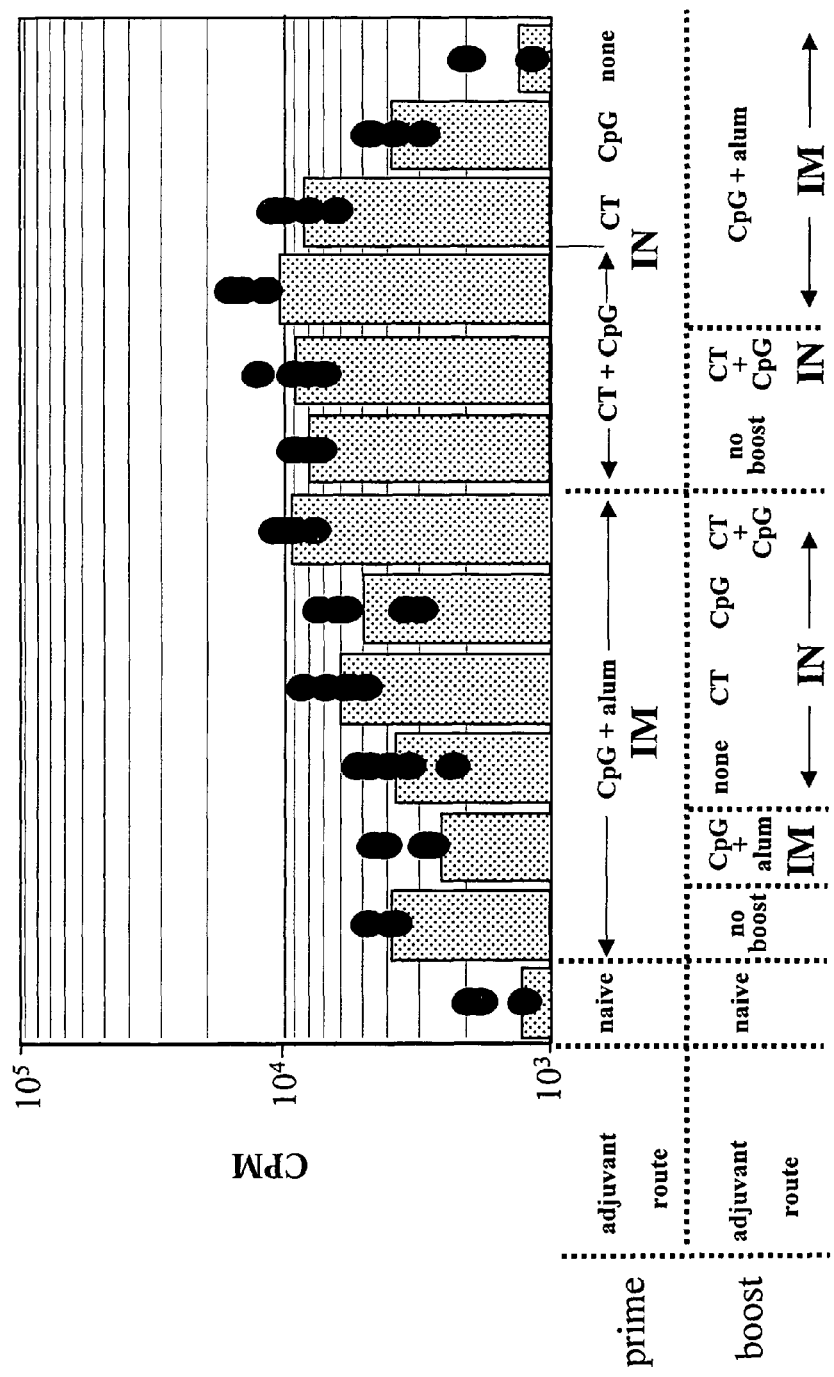
FIG. 10 is a bar graph depicting the effect of different prime/boost strategies with different adjuvants on HBsAg specific T cell proliferation, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90), or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90), and 4 weeks after boost mice were killed by Halothane overdose, splenocytes isolated and HBsAg specific T cell proliferation measured.
Figure 11:
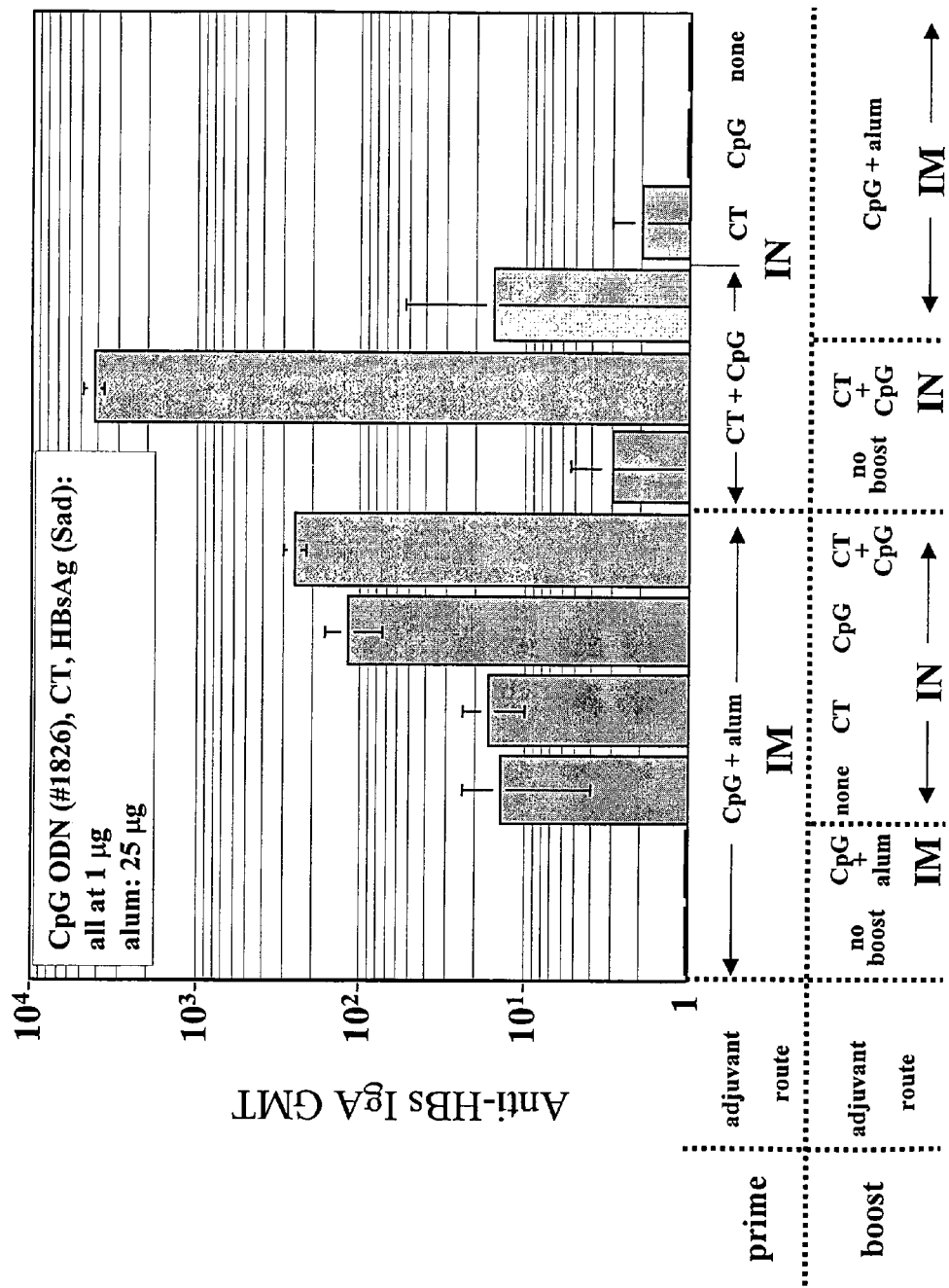
FIG. 11 is a bar graph depicting the effect of different prime/boost strategies with different adjuvants on anti-HBs IgA titers in lung washes, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90), or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90). Four weeks after boost mice were killed by Halothane overdose and lungs were washed with 1 ml TBS.
Figure 12:
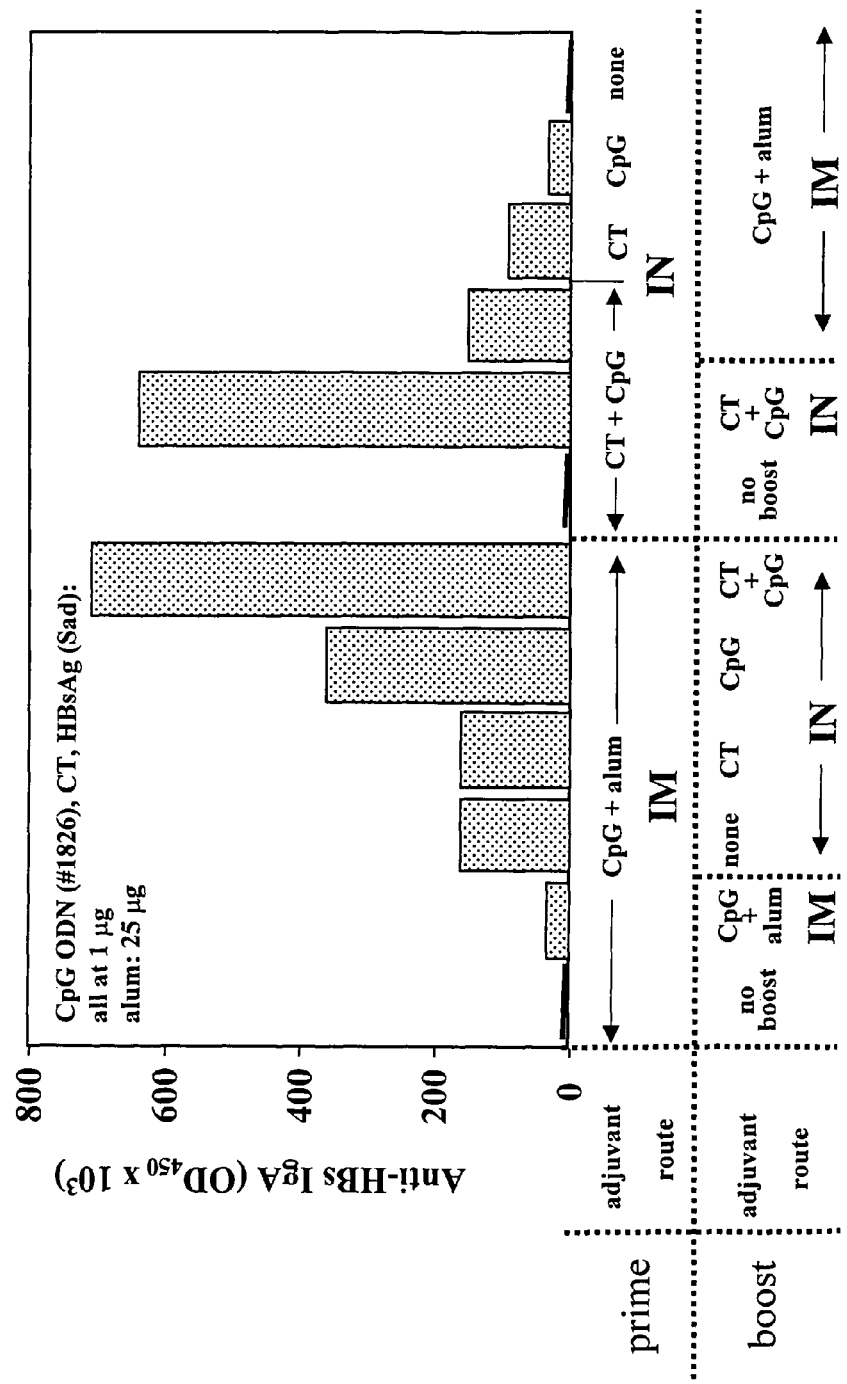
FIG. 12 is a bar graph depicting the effect of different prime/boost strategies with different adjuvants on anti-HBs IgA titers in saliva, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90), or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90). Four weeks after boost mice were injected with 100 µl 0.5% Pilocarpine hydrochloride solution and saliva collected.
Figure 13:
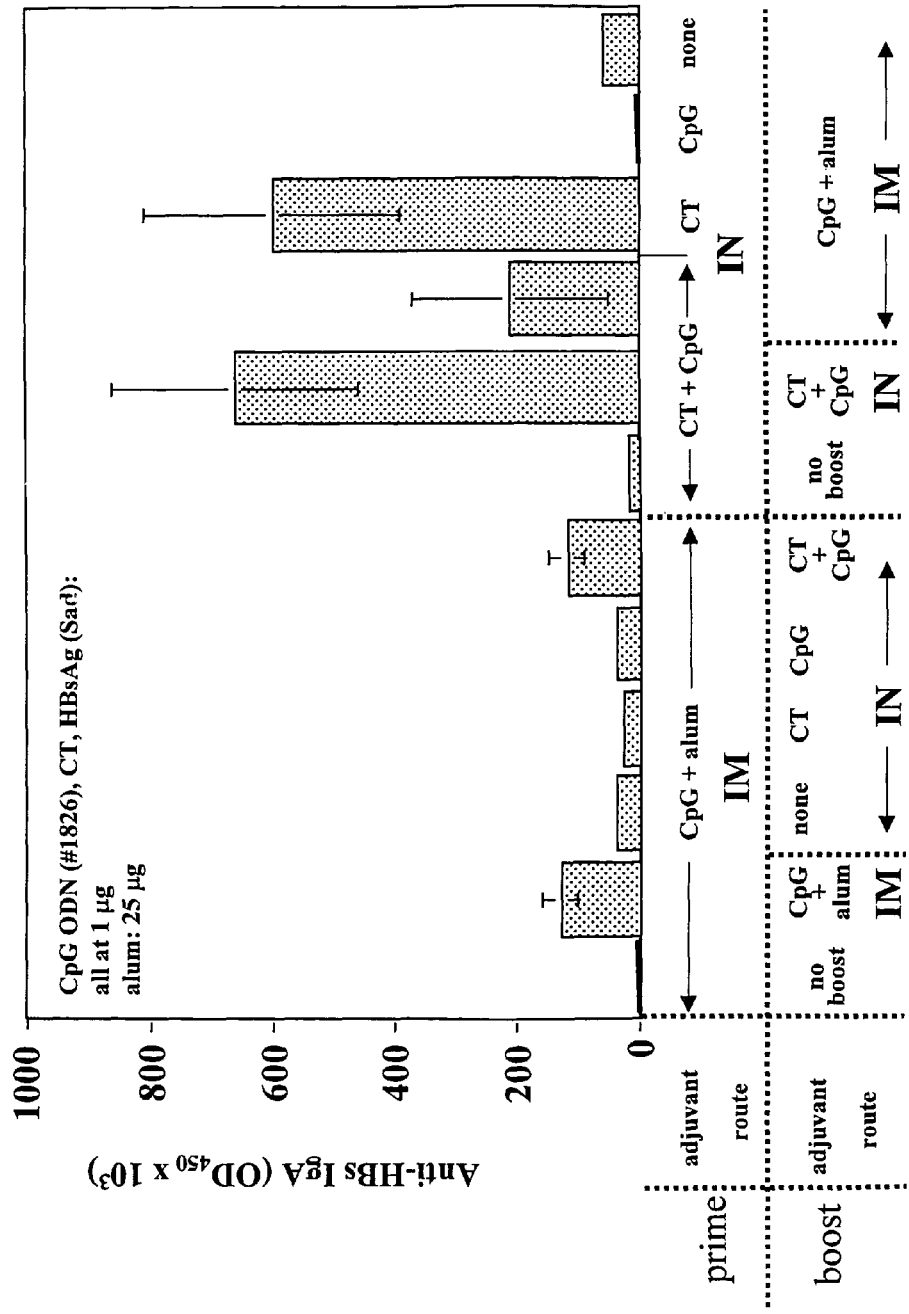
FIG. 13 is a bar graph depicting the effect of different prime/boost strategies with different adjuvants on anti-HBs IgA titers in fecal pellet solutions, wherein BALB/c mice were immunized: (i) by IM injection with HBsAg (1 µg) in combination with alum plus CpG oligonucleotide (motif #1826, SEQ ID NO. 90) and boosted at 4 weeks as prime, or by IN inhalation with HBsAg (1 µg) without or in combination with Cholera toxin (CT) and/or CpG oligonucleotide (motif #1826, SEQ ID NO. 90), or (ii) by IN inhalation with HBsAg (1 µg) without or in combination with Cholera toxin (CT) and/or CpG oligonucleotide (motif #1826, SEQ ID NO. 90) and boosted at 4 weeks as prime or by IM injection with HBsAg (1 µg) in combination with alum plus CpG oligonucleotide (motif #1826, SEQ ID NO. 90). Four weeks after boost mice were isolated for 24 hr and fecal pellets were collected and resuspended in TBS at 0.1 mg/ml.

The invention can also be used in combination with parenteral immunization strategies (e.g., intramuscular, intradermal or subcutaneous injection), which are normally used for the induction of systemic immune responses. Remarkably, mice immunized with HBsAg and having CpG oligonucleotide as at least one adjuvant, when primed by a parenteral route (IM) and boosted by a mucosal route (IN) or primed IN and boosted IM had up to 10-fold higher IgG (i.e., systemic humoral response) than when both prime and boost were by the IM route (FIG. 8). Cellular immune responses were also stronger with the parenteral/mucosal combined approaches than with only IN or only IM, as indicated by stronger CTL (FIG. 9) and higher T-cell proliferation (FIG. 10). While the IN prime and boost gives good mucosal responses the IM prime and boost gives no detectable mucosal responses (FIGS. 11-13). The IM prime and IN boost approach also gave significant IgA in lung washes (FIG. 11) and saliva (FIG. 12) but not feces (FIG. 13).

The mucosal adjuvants useful according to the invention are non-oligonucleotide mucosal adjuvants. A "non-oligonucleotide mucosal adjuvant" as used herein is an adjuvant other than a CpG oligonucleotide that is capable of inducing a mucosal immune response in a subject when administered to a mucosal surface in conjunction with an antigen. Mucosal adjuvants include but are not limited to Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, Escherichia coli heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler BD, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of Borrelia burgdorferi, outer membrane protine of Neisseria meningitidis)(Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worster, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

Although mucosal delivery of the antigen is considered a prerequisite for induction of strong mucosal immune responses, it is possible to induce strong mucosal immunity to systemically delivered antigens by modulating the immune response with steroid hormones, such as described for 1,25-Dihydroxy vitamin $D_3$ [$1,25(OH)_2D_3$] (Daynes et al., 1996). The invention also includes methods for the administration of CpG oligonucleotide alone or in combination with other mucosal adjuvants and antigen to hormonally treated individuals. Each of the compounds may be administered together or separately, systemically or mucosally. In some embodiments the CpG oligonucleotide and antigen and optionally other mucosal adjuvants are administered mucosally and the hormone is administered systemically. The hormone may be given parenterally (e.g., subcutaneous injection) or mucosally (e.g., orally).

Mucosal immune responses can also be induced with the co-administration of cytokines with the CpG oligonucleotides. Immune responses can also be augmented by co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997). The cytokines can be administered directly with CpG oligonucleotides or may be administered in the form of a nucleic acid vector that encodes the cytokine, such that the cytokine can be expressed in vivo. In one embodiment, when the CpG is administered in the form of a plasmid expression vector, the vector may encode the cytokine, and a separate administration of cytokine is not required. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, granulocyte-macrophage colony stimulating factor (GM-CSF), granulocyte colony stimulating factor (GCSF), interferon-γ (γ-INF), tumor necrosis factor (TNF), TGF-β, FLT-3 ligand, and CD40 ligand.

Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. Th1 cells express IL-3, IL-4, IL-5, IL-6, IL-9, IL-10, IL-13, GM-CSF and low levels of TNF-α. The TH1 subset promotes delayed-type hypersensitivity, cell-mediated immunity, and immunoglobulin class switching to $IgG_{2a}$. The Th2 subset induces humoral immunity by activating B cells, promoting antibody production, and inducing class switching to $IgG_1$ and IgE. In some embodiments it is preferred that the cytokine be a Th1 cytokine.

CpG oligonucleotides were found, surprisingly, to induce mucosal immunity in remote sites as well as local sites. A "remote site" as used herein is a mucosal tissue that is located in a different region of the body than the mucosal tissue to which the CpG oligonucleotide has been administered. For instance if the CpG oligonucleotide is administered intranasally, a remote site would be the mucosal lining of the gut.

For use in the instant invention, the nucleic acids can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid Res.* 14:5399-5407, 1986, Garegg et al., *Tet. Let.* 27:4055-4058, 1986, Gaffney et al., *Tet. Let.* 29:2619-2622, 1988). These chemistries can be performed by a variety of automated oligonucleotide synthesizers available in the market. Alternatively, CpG dinucleotides can be produced on a large scale in plasmids, (see Sambrook, T., et al., *Molecular Cloning: A Laboratory Manual*, Cold Spring Harbor laboratory Press, New York, 1989) and separated into smaller pieces or administered whole. After being administered to a subject the plasmid can be degraded into oligonucleotides. Oligonucleotides can be prepared from existing nucleic acid sequences (e.g., genomic or cDNA) using known techniques, such as those employing restriction enzymes, exonucleases or endonucleases.

For use in vivo, nucleic acids are preferably relatively resistant to degradation (e.g., via endo- and exo-nucleases). Secondary structures, such as stem loops, can stabilize nucleic acids against degradation. Alternatively, nucleic acid stabilization can be accomplished via phosphate backbone modifications. One type of stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., *Chem. Rev.* 90:544, 1990; Goodchild, J., *Bioconjugate Chem.* 1:165, 1990).

Nucleic acids containing an appropriate unmethylated CpG can be effective in any vertebrate. Different nucleic acids containing an unmethylated CpG can cause optimal immune stimulation depending on the mammalian species. Thus an oligonucleotide causing optimal stimulation in humans may not cause optimal stimulation in a mouse and vice versa. One of skill in the art can identify the optimal oligonucleotides useful for a particular mammalian species of interest using routine assays described herein and/or known in the art, using the guidance supplied herein.

The term "effective amount" of a CpG oligonucleotide refers to the amount necessary or sufficient to realize a desired biologic effect. For example, an effective amount of an oligonucleotide containing at least one unmethylated CpG for inducing mucosal immunity is that amount necessary to cause the development of IgA in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG oligonucleotide being administered (e.g. the number of unmethylated CpG motifs or their location in the nucleic acid), the antigen, the size of the subject, or the severity of the disease or condition. One of ordinary skill in the art can empirically determine the effective amount of a particular CpG oligonucleotide and antigen without necessitating undue experimentation.

Subject doses of the compounds described herein typically range from about 80 µg/day to 16,000 µg/day, more typically from about 800 µg/day to 8000 µg/day, and most typically from about 800 µg/day to 4000 µg/day. Stated in terms of subject body weight, typical dosages range from about 1 to 200 µg/kg/day, more typically from about 10 to 100 µg/kg/day, and most typically from about 10 to 50 µg/kg/day. Stated in terms of subject body surface areas, typical dosages range from about 40 to 8000 $\mu g/m^2$/day, more typically from about 400 to 4000 $\mu g/m^2$/day, and most typically from about 400 to 2000 $g/m^2$/d.

In some embodiments, particularly when the CpG is in a plasmid vector, at least 50 µg of the CpG is administered to a subject. In other embodiments at least 75 µg, 100 µg, 200 µg, 300 µg, 400 µg, 500 µg and every integer in between of the CpG is administered to the subject.

For any compound described herein the therapeutically effective amount can be initially determined from cell culture assays. For instance the effective amount of CpG oligonucleotide useful for inducing mucosal immunity can be assessed using the in vitro assays described above with respect to stimulation index. The stimulation index can be used to determine as effective amount of the particular oligonucleotide for the particular subject, and the dosage can be adjusted upwards or downwards to achieve the desired levels in the subject. Therapeutically effective amounts can also be determined from animal models. A therapeutically effective dose can also be determined from human data for CpG oligonucleotides which have been tested in humans (human clinical trials have been initiated) and for compounds which are known to exhibit similar pharmacological activities, such as other mucosal adjuvants, e.g., LT and other antigens for vaccination purposes. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG oligonucleotide can be administered to a subject by any mode that delivers the oligonucleotide to a mucosal surface. "Administering" the pharmaceutical composition of the present invention may be accomplished by any means known to the skilled artisan. Preferred routes of administration include but are not limited to oral, intranasal, intratracheal, inhalation, ocular, vaginal, and rectal.

For oral administration, the compounds (i.e., CpG oligonucleotides, antigen, mucosal adjuvant) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science 249:1527-1533, 1990, which is incorporated herein by reference.

The CpG oligonucleotides and antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG oligonucleotide and antigens optionally included in a pharmaceutically-acceptable carrier. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The CpG oligonucleotides or antigens useful in the invention may be delivered in mixtures with additional mucosal adjuvant(s) or antigen(s). A mixture may consist of several mucosal adjuvants in addition to the CpG oligonucleotide or several antigens.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

1. Materials and Animals

Mice. All experiments were carried out using female BALB/c mice aged 6-8 weeks with 5-10 mice per experimental or control group. For intranasal immunizations, mice were lightly anaesthetized with Halothane® (Halocarbon Laboratories, River Edge, N.J.).

Adjuvants: Mice were immunized by IN administration of 1 μg HBsAg (plasma-derived HBV S protein, ad subtype, Genzyme Diagnostics, San Carlos, Calif.), alone or combined with 1 or 10 μg of CT (purified from *Vibrio cholerae*, Sigma, St. Louis, Mo.), LT (purified from *Escherichia coli*, Sigma), CTB (purified from *Vibrio cholerae*, Sigma), LTK63 (mutant of LT bearing an Ser→Lys at position 63, generously provided by Dr. Rino Rappuoli, IRIS, Chiron S.p.A., Italy) and/or CpG ODN (5'-TCCATGACGTTCCTGACGTT-3', CpG ODN #1826 SEQ ID NO. 90) or non-CpG control ODN (5'TCCAGGACTTCTCTCAGGTT-3', CpG ODN #1982 SEQ ID NO. 91) (Hybridon Specialty Products, Milford, Mass.). The antigen and adjuvant(s) were made up to a total volume of 150 μl with 0.15 M NaCl, and were administered by IN inhalation. ODN were resuspended in 10 mM Tris (pH 7.0), 1 mM EDTA for storage at +4EC before dilution into saline for immunization. LPS level in ODN was undetectable (<1 ng/mg) by Limulus assay (Whittaker Bioproducts, Walkersville, Md.).

2. Mucosal Immunization

Each animal was immunized with 1 or 10 μg plasma-derived HBV S protein (HBsAg, ad subtype, Genzyme Diagnostics, San Carlos, Calif.), which was administered alone or in combination with 1 or 10 μg of CT or LT or derivative of them and/or CpG oligonucleotide #1826. The derivatives of CT were the B subunit of CT (CTB). The detoxified derivatives of LT were all produced by genetic mutations that affected the A subunit or enzymatic activity and included LTK63. All vaccines were delivered in a total volume of 150 μl, which was applied as droplets directly over both external nares of lightly anaesthetized 4 mice. Some mice were boosted in the identical manner at 8 weeks after prime. All experimental groups contained 5 or 10 mice.

3. Collection of Samples

Plasma: Plasma was recovered from mice at various times after immunization (1, 2, 4 and 8 wk post-prime and 1, 2 and 4 wk post-boost) by retro-orbital bleeding and stored at −20° C. until assayed.

Fecal pellets: Fecal pellets were collected from mice at various times after immunization (1, 2, 4 and 8 wk post-prime and 1, 2 and 4 wk post-boost). Mice were isolated in individual cages without bedding for a 24 hr period, following which fecal pellets were collected and weighed into 0.1 mg aliquots. One ml TBS (0.05 M Tris-HCl, 0.15 M NaCl, pH 7.5) and 0.1 µg sodium azide (Sigma) were added per 0.1 mg of fecal material. Samples were allowed to rehydrate for 30 min at RT, then were centrifuged at 6000 rpm for 15 min. to remove fecal debris and supernatants were collected and stored at −20° C. until assayed for S-IgA by ELISA.

Lung washes: Lung washes were carried out on mice 4 wk after primary immunization or boost. A 0.33 cc Insulin syringe with a 29G1/2 needle attached (Becton Dickinson, Franklin Lakes, N.J.) was used for carrying out lung washes. One ml TBS was drawn into the syringe and a length of polyethylene (PE) tubing that was 1 cm longer than the needle was attached (PE20, ID=0.38 mm, Becton Dickinson). The mouse was killed by anesthetic overdose and the trachea was immediately exposed through an anterior midline incision made using fine-tipped surgical scissors (Fine Science Tools Inc., North Vancouver, BC). A small incision was then made in the trachea and a clamp (Fine Science Tools Inc., North Vancouver, BC) was placed above it. The PE tubing was passed a few mm down the trachea through the incision and a second clamp was placed just below the incision to hold the PE tubing in place in the trachea. The TBS solution was slowly instilled in the lungs then withdrawn three times (80% recovery expected). Recovered samples were centrifuge at 13,000 rpm for 7 min., and the supernatants were collected and stored at −20° C. until assayed by ELISA.

4. Evaluation of Immune Responses

Systemic humoral response: HBsAg-specific antibodies (anti-HBs) in the mouse plasma were detected and quantified by end-point dilution ELISA assay (in triplicate) for individual animals as described previously (Davis et al., 1998). Briefly, 96-well polystyrene plates (Corning) coated overnight (RT) with plasma derived HBsAg particles (as used for immunization) (100 µl of 1 µg/ml in 0.05 M sodium carbonate-bicarbonate buffer, pH 9.6) were incubated with the plasma for 1 hr at 37° C. Captured antibodies were then detected with horseradish peroxidase (HRP)-conjugated goat anti-mouse IgG, IgG1 or IgG2a (1:4000 in PBS-Tween, 10% PBS: 100 µl/well; Southern Biotechnology Inc., Birmingham, Ala.), followed by addition of o-phenylenediamine dihydrochloride solution (OPD, Sigma), 100 µl/well, for 30 min at RT in the dark. The reaction was stopped by the addition of 4 $NH_2SO_4$, 50 µl/well.

End-point dilution titers were defined as the highest plasma dilution that resulted in an absorbance value (OD 450) two times greater than that of non-immune plasma, with a cut-off value of 0.05. Anti-HBs titers of responding mice (endpoint titers >10) were expressed as means SEM of individual animal values, which were themselves the average of triplicate assays.

Mucosal humoral response: This was carried out on fecal supernatants or recovered lung washes as for plasma (above) except samples were incubated on coated plates for 2 hr at 37° C. and captured antibodies were detected with HRP-conjugated goat anti-mouse IgA (1:1000 in PBS-Tween. 10% PBS: 100 µl/well; Southern Biotechnology Inc). Non-immune fecal pellet or lung wash solutions were used to determine negative control values. For lung wash solutions, anti-HBs endpoint dilution titers were reported (as described above), whereas for fecal pellet solutions, absorbance values (OD 450) greater than that of non-immune fecal pellet solution were calculated and expressed as mean SEM of individual OD 450 values, which were themselves the average of triplicate assays.

Evaluation of CTL responses: Spleens were removed from mice 4 wk after primary immunization or boost. In vitro assay of HBsAg-specific cytolytic activity was carried out as previously described (Davis et al., 1998). In brief, single cell suspensions were prepared and suspended in tissue culture medium (RPMI 1640, 10% FBS, Life Technologies, Grand Island, N.Y., supplemented with penicillin-streptomycin solution, 1000 U/ml, 1 mg/ml final concentrations respectively, Sigma). Splenocytes ($3 \times 10^7$) were co-cultured for 5 days (37° C., 5% CO2) with $1.5 \times 10^6$ syngeneic HBsAg-expressing stimulator cells (P815-preS, generously provided by F. V. Chisari, Scripps Institute, La Jolla, Calif.) that had been previously inactivated by irradiation (20 000 rad). Effector cells were harvested, washed, serially diluted and cultured with $5 \times 10^4$ $^{51}$Cr-labeled HBsAg-expressing target cells (P815S) in round bottom 96-well culture plates (37° C., 5% CO2, 4 hr). Supernatant (100 µl) was removed for radiation (gamma) counting. Spontaneous release was determined by incubating target cells without effector cells and total release by addition of 100 µl 2 N HCl to the target cells. The percent lysis was calculated as [(experimental release−spontaneous release)/(total release−spontaneous release)]×100. The percent specific lysis was calculated as % lysis with P815S−% lysis with P815 cells. CTL activity for responding mice [% specific lysis >10 at effector:target (E:T) of 25:1] were expressed as mean SEM of individual animal values, which were themselves the average of triplicate assays.

5. Statistical Analysis

Data were analyzed using the GraphPAD InStat program (Graph PAD Software, San Diego). The statistical significance of the difference between two groups was determined from the means and standard deviations by Student's 2-tailed t-test and between three or more groups by 1-factor analysis of variance (ANOVA) followed by Tukey's test for multiple range testing. Differences were considered to be not significant with p>0.05.

Example 2

Systemic Humoral Responses after Mucosal Immunization

BALB/c mice immunized on a single occasion by IN inhalation of HBsAg without adjuvant did not have any detectable anti-HBs IgG antibodies in their plasma with 1 µg HBsAg and only extremely low titers (<20) in a few mice with 10 µg of antigen (FIG. 1).

In contrast, titers of anti-HBs IgG were considerably greater when HBsAg was administered in combination with either CpG oligonucleotide or CT as adjuvant (FIG. 1). With a low dose of adjuvant (1 µg) and either a low or high dose of antigen (1 or 10 µg HBsAg), CpG oligonucleotide was found to be equivalent to CT for induction of plasma anti-HBs IgG (p=0.73 with 1 µg HBsAg, and 0.13 with 10 µg HBsAg). CpG oligonucleotide and CT were also equivalent with a high dose of adjuvant (10 µg) and high dose of antigen (10 µg HBsAg) (p=0.08), however with a lower dose of antigen, the higher dose of CT was superior to the CpG oligonucleotide (p=0.01)

(FIG. 1). These results indicate that CpG oligonucleotide is essentially equal to CT for enhancement of systemic immune responses with mucosal delivery (IN) of a protein antigen.

A combined low dose of CpG oligonucleotide and CT (1 µg of each) gave a better systemic humoral response than 10 µg CpG oligonucleotide alone (p=0.01) and was equal to that with 10 µg CT alone (p=0.22), when added to a 1 µg dose of HBsAg. Furthermore, with a 10 µg dose of HBsAg, the combined adjuvants (1 µg each) induced anti-HBs IgG titers as high as those with 10 µg of either adjuvant alone (CT, p=0.27; CpG oligonucleotide, p=0.09) (FIG. 1). These finding indicate that CpG oligonucleotide can act synergistically with CT when administered to mucosal tissue to induce strong systemic humoral responses, and thereby permit a lower dose of adjuvant to be administered.

Antibody titers were further increased about 10-fold by boosting at 8 wks. Post-boost titers of plasma IgG were equivalent for CT and CpG oligonucleotide used alone, and were 5-10 times higher than that with both adjuvants together (FIG. 2). These results indicate that the adjuvant effect of CpG oligonucleotide alone or in combination with CT can be enhanced by boosting.

Evaluation of plasma for IgG antibody isotypes after a single mucosal immunization showed predominantly IgG1 antibodies (Th2-like) with CT and mixed IgG1/IgG2a antibodies (Th0) with CpG oligonucleotide alone or in combination with CT. The proportion of IgG2a isotype of antibodies, was about 10-times greater with CpG ODN than CT, indicating a greater Th1 influence of CpG ODN compared to CT. Furthermore, the combination of CpG ODN and CT gave a 50-times higher IgG2a:IgG1 ratio than CT alone (FIG. 3). Following boost, anti-HBs were still predominantly IgG1 with CT and mixed with CpG oligonucleotide, although in the latter case, the proportion of IgG2a was now higher. Surprisingly, plasma anti-HBs after boost with CpG oligonucleotide and CT were now predominantly IgG2a (Th-1 like) (FIG. 3). These findings indicate that CpG oligonucleotide as a mucosal adjuvant stimulates a Th1-like response, even in the presence of a strong Th2-like adjuvant like CT.

Similar results were found when LT was used in place of CT (FIG. 7, Tables 2 and 3). CT and LT, which are closely related with considerable structural and functional homology, are both too toxic for use in humans. However there are a number of derivations of CT and LT that retain some adjuvant activity yet are much less toxic. One example is the B-subunit of CT (CTB) which is non-toxic since the toxicity is associated with the A subunit. Another example is LTK63, a genetically detoxified mutant of LT with no toxic enzymatic activity. Although these adjuvants are being used in human clinical trials, neither was a strong as CpG ODN for induction of systemic immunity (serum IgG) when each was used at 1 µg (FIG. 7). There was also a synergistic effect when CpG ODN and CTB or LTK63 were used together, however this was more noticeable for Th1-bias than for strength of the antibody response (FIG. 7 and Table 2).

Example 3

Systemic CTL Response after Mucoal Immunization

Figure 4:
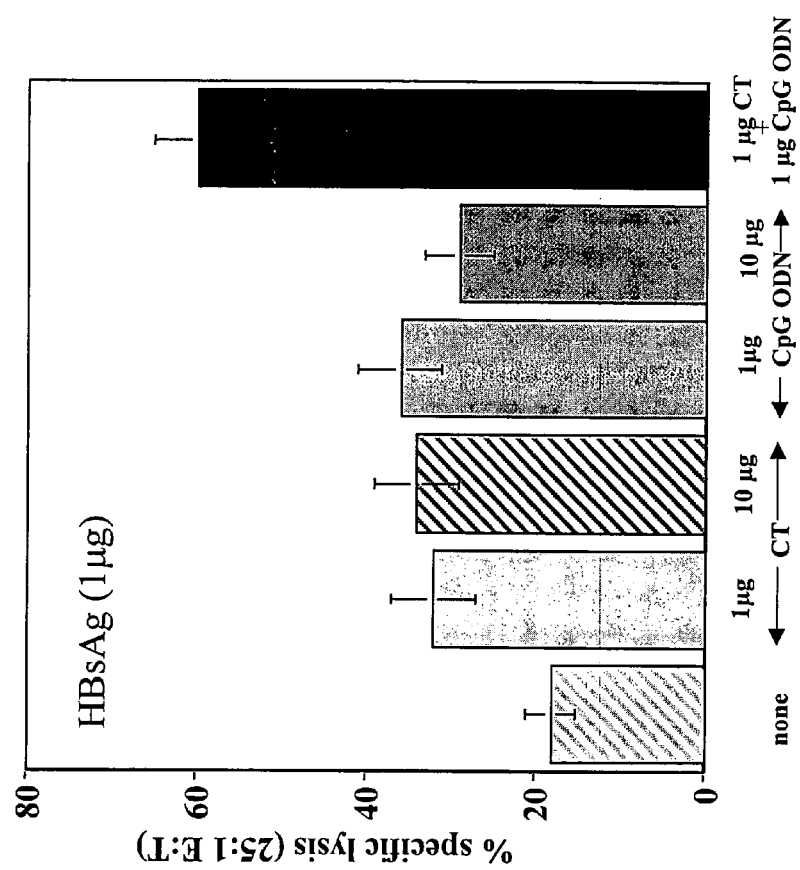
FIG. 4 is a bar graph depicting the effect of different adjuvants on HBsAg specific CTL response, wherein BALB/c mice were immunized by IN inhalation with HBsAg (10 μg) without or in combination with Cholera toxin (CT) and/or CpG oligonucleotide (motif #1826, SEQ ID NO. 90) adjuvants at different doses (1 or 10 μg) and four weeks after immunization mice were killed by Halothane overdose, splenocytes isolated and HBsAg specific CTL activity measured.

Only low levels of CTL were induced with HBsAg alone, however the addition of either CpG oligonucleotide or CT significantly increased HBsAg-specific CTL activity. CTL responses were equivalent for CT and CpG oligonucleotide, regardless of dose. However, a combination of CT and CpG oligonucleotide (1 µg of each) increased CTL responses approximately two-fold. (FIG. 4).

Example 4

Mucosal Humoral Responses after Mucosal Immunization

No anti-HBs S-IgA were detected in lung washes of mice immunized with 1 or 10 µg HBsAg alone. Nor were anti-HBs IgA detected with the low dose of antigen combined with a low dose (1 µg) of either CpG oligonucleotide or CT or with a high dose of CpG oligonucleotide; only low titers were detected with low dose antigen and high dose CT (FIG. 5). However when low doses of both CpG oligonucleotide and CT (1 µg each) were used together with the low dose of antigen, significant levels of HBsAg-specific S-IgA could be detected in lung washes (FIG. 5).

With a higher antigen dose (10 µg), S-IgA was detected in lung washes of mice administered the either low or high doses of CT and/or CpG oligonucleotide. Titers of IgA were significantly higher with 1 µg of the two adjuvants together than with 10 µg of CT or CpG oligonucleotide alone (p=0.0003 and <0.0001 respectively) (FIG. 5). IgA titers increased approximately ten-fold after boosting with both adjuvants. Thus CpG oligonucleotide can induce specific local mucosal immunity against antigen administered intranasally. Furthermore, similar to as was found for systemic response (above) CpG oligonucleotide acts in a synergistic fashion with CT for the induction of mucosal immunity.

IgA was also detected in fecal pellets of mice immunized with HBsAg and 10 µg CpG oligonucleotide. In contrast, only very low levels were detected in mice immunized with HBsAg in combination with CT (1 or 10 µg) (FIG. 6). Thus, CpG oligonucleotide can induce mucosal immunity at distant mucosal sites.

Example 5

Mucosal and Systemic Immune Response to other Mucosal Adjuvants

Systemic Immune Responses

IN delivery of HBsAg (1 µg) without adjuvant did not induce detectable anti-HBs IgG antibodies in the plasma of any mice (0/15). In contrast, high titers of anti-HBs IgG were induced in all mice when HBsAg was administered in combination with CpG, CT or LT as adjuvant (FIG. 7, Table 2). At a low dose (1 µg) LT, CT and CpG gave equivalent anti-HBs IgG titers (p=0.22). At a high dose (10 µg) CT and LT gave higher titers than CpG, however 5/10 mice receiving this dose of LT died within 10 days. No detectable anti-HBs IgG was detected with a low dose (1 µg) of CTB or LTK63, however a high dose (10 µg) of CTB gave low anti-HBs IgG endpoint ELISA titers and a high dose (10 µg) of LTK63 gave as good levels of anti-HBs IgG as a high dose (10 µg) of CpG (p=0.97) (FIG. 7, Tables 2 and 3).

When used together, CpG and either LT or CT (1 µg each) appeared to have a synergistic effect since anti-HBs titers were 5 to 10 times higher than with any one of the three adjuvants alone (FIG. 7). Indeed, CpG plus LT (1 µg each) gave a better response than 10 µg of CpG or LT alone (p=0.007, 0.015 respectively) and the response with CpG plus CT (1 µg each) was equal to that with 10 µg CT alone (p=0.65). In contrast, there was no synergistic effect with LTK63 plus CpG (1 µg each) for anti-HBs IgG titers, which were equivalent to those with 1 µg CpG alone (p=0.40).

Surprisingly, CTB plus CpG (1 µg each) gave lower anti-HBs titers than 1 µg CpG alone (p=0.007) (FIG. 7). Adjuvant effects with CpG ODN were due to the CpG motif rather than a non-specific effect of the ODN backbone since mice immunized with 1 µg of HBsAg plus 10 µg of non-CpG ODN had no (7/10) or very low (3/10) titers of anti-HBs IgG antibodies (data not shown).

Antibodies were predominantly IgG1 (Th2-like) with CT, CTB and LT and mixed IgG1/IgG2a (Th1/Th2) with LTK63. At a low dose (1 µg) responses with CpG were mixed IgG1/IgG2a (Th1/Th2), but at a higher dose (10 µg) were more Th1 (IgG2a >>IgG1). Responses were mixed Th1/Th2 with CT/CpG or CTB/CpG and more Th1 with LT/CpG. At a low dose (1 µg each) LTK63/CpG responses were Th1/Th2, but at a higher dose (10 µg each) were more Th1 (Table 3). Thus coadministration of CpG with other adjuvants shifted responses towards a more Th1-like response as indicated by a greater proportion of IgG2a antibodies.

Mucosal Immune Responses

When adjuvants were used alone, only mice receiving LT or LTK63 had detectable IgA in lung washes, however when CpG ODN was also included with CT or LT a greater number of animals responded or titers were higher than with comparable doses alone, suggesting a synergistic effect. CpG alone did not induce IgA. Neither did CTB, alone or combined with CpG (Table 3).

Only a few adjuvants on their own (LT and CpG) induced IgA in the feces, and then only in some animals. No significant IgA was detected with CT, CTB, LTK63 or non-CpG ODN. CpG and LT together resulted in IgA in the feces of a greater proportion of animals than either adjuvant alone suggesting an additive or synergistic effect. No such effects were evident with other combinations (Table 3).

TABLE 2

Effect of adjuvant on HBsAg-specific antibody isotypes

| | | Anti-HBs response | | |
|---|---|---|---|---|
| Adjuvant[a] | dose (µg) | IgG2a[b] | IgG1[b] | IgG2a:IgG1[c] |
| none | — | 0 | 0 | N/A[d] |
| CT | 1 | 36 | 1632 | 0.02 |
| CT | 10 | 406 | 3849 | 0.1 |
| CTB | 1 | 0 | 0 | N/A |
| CTB | 10 | 6 | 59 | 0.1 |
| LT | 1 | 226 | 6457 | 0.04 |
| LT | 10 | 895 | 2024 | 0.44 |
| LTK63 | 1 | 0 | 0 | N/A |
| LTK63 | 10 | 231 | 455 | 0.5 |
| CpG ODN | 1 | 146 | 403 | 0.4 |
| CpG ODN | 10 | 549 | 41 | 13.4 |
| control ODN | 1 | 0 | 0 | N/A |
| control ODN | 10 | 0 | 0 | N/A |
| CT + CpG ODN | 1 each | 3376 | 2374 | 1.4 |
| CTB + CpG ODN | 1 each | 0 | 0 | N/A |
| LT + CpG ODN | 1 each | 6268 | 1438 | 4.4 |
| LTK63 + CpG ODN | 1 each | 185 | 272 | 0.7 |
| CT + control ODN | 1 each | 402 | 5087 | 0.08 |
| CT + CpG ODN | 10 each | =[e] | = | = |
| CTB + CpG ODN | 10 each | 227 | 208 | 1.1 |
| LT + CpG ODN | 10 each | = | = | = |
| LTK63 + CpG ODN | 10 each | 3170 | 413 | 7.7 |

TABLE 3

Effect of adjuvant on HBsAg-specific IgA responses

| | | Anti-HBs response[b] | | | |
|---|---|---|---|---|---|
| | | lung | | fecal | |
| Adjuvant[a] | dose (µg) | IgA[c] | no. of responders | IgA[d] | no. of responders |
| none | — | 0 | 0 | 0 | 0 |
| CT | 1 | 0 | 0 | 0 | 0 |
| CT | 10 | 0 | 0 | 0 | 0 |
| CTB | 1 | 0 | 0 | 0 | 0 |
| CTB | 10 | 0 | 0 | 0 | 0 |
| LT | 1 | 160 ± 68 | 5 | 100, 200 | 2 |
| LT | 10 | 17 ± 5 | 3/3 (2 dead) | 200 ± 50 | 3/3 (2 dead) |
| LTK63 | 1 | 0 | 0 | 0 | 0 |
| LTK63 | 10 | 26 ± 6 | 4 | 0 | 0 |
| CpG ODN | 1 | 0 | 0 | 100 | 1 |
| CpG ODN | 10 | 0 | 0 | 0 | 0 |
| control ODN | 1 | 0 | 0 | 0 | 0 |
| control ODN | 10 | 0 | 0 | 0 | 0 |
| CT + CpG ODN | 1 each | 17, 49 | 2 | 120 | 1 |
| CTB + CpG ODN | 1 each | 0 | 0 | 0 | 0 |
| LT + CpG ODN | 1 each | 232 ± 34 | 5 | 150 ± 20 | 4 |
| LTK63 + CpG ODN | 1 each | 14 | 1 | 0 | 0 |
| CT + control ODN | 1 each | 0 | 0 | 0 | 0 |
| CT + CpG ODN | 10 each | =[e] | = | = | = |
| CTB + CpG ODN | 10 each | 17 | 1 | 0 | 0 |
| LT + CpG ODN | 10 each | = | = | = | = |
| LTK63 + CpG ODN | 10 each | 28 ± 46 | 3/4 | 130 | 1/4 |

TABLE 4 summary of effects of different prime/boost strategies on HBsAg-specific immune responses

| PRIME | BOOST | IgA L | IgA S | IgA F | IgG | CTL | TCP |
|---|---|---|---|---|---|---|---|
| IM Ag + alum + CpG | none | | | | X | | X |
| | IM Ag + alum + CpG | | | | X | X | X |
| | IN Ag | X | X | | X | X | X |
| | IN Ag + CT | X | X | | X | X | X |
| | IN Ag + CpG | X | X | | X | X | X |
| | IN Ag + CT + CpG | X | X | X | X | X | X |
| IN Ag | | | | | X | | |
| IN Ag + CT | IM Ag + alum + CpG | | | | X | X | X |
| IN Ag + CpG | | | | | X | X | X |
| IN Ag + CT + CpG | | X | X | X | X | X | X |
| IN Ag + CT + CpG | IN Ag + CT + CpG | X | X | X | X | X | X |
| INAg + CT+ CpG | none | | | | X | | X |

Ag: 1 µg HBsAg
CpG: 1 pg #1826,
CT: 1 µg,
alum: 25 µg
L: lung, cut-off GMT = 10
S : saliva, cut-off $OD_{450} \times 10^3$ =100
F: fecal, cut-off $OD_{450} \times 10^3$ =100
CTL, cut-off 20% at E:T 100:1
TCP, cut-off 2500 cpm

REFERENCES

Alpar H O, Ozsoy Y, Bowen J, Eyles J E, Conway B R, Williamson E D. Potential of particulate carriers for the mucosal delivery of DNA vaccines. Biochemical Society Transactions 1997; 25(2):337S.

Ballas, Z. K., W. L. Rasmussen, and A. M. Krieg. 1996. Induction of natural killer activity in murine and human cells by CpG motifs in oligodeoxynucleotides and bacterial DNA. J. Immunol. 157, 1840.

Bird, A. P. CpG islands as gene markers in the vertebrate nucleus. 1987. Trends in Genetics 3:342.

Bowersock T L. Shalaby W S. Levy M. Samuels M L. Lallone R. White M R. Borie D L. Lehmeyer J. Park K. Evaluation of an orally administered vaccine, using hydrogels containing bacterial exotoxins of Pasteurella haemolytica, in cattle. Am. J. Vet. Res. 1994; 55: 502-9.

Bueler H and Mulligan R C. Induction of antigen-specific tumor immunity by genetic and cellular vaccines against MAGE: enhanced tumor protection by coexpression of granulocyte-macrophage colony-stimulating factor and B7-1. 1996; 2; 545-555.

Chace, J. H., N. A. Hooker, K. L. Mildenstein, A. M. Krieg, and J. S. Cowdery. 1997. Bacterial DNA-induced NK cell IFN-γ production is dependent on macrophage secretion of IL-12. Clin. Immunol. Immunopath., 84:185.

Chow Y H, Huang W L, Chi W K, Chu Y D, Tao M H. Improvement of hepatitis B virus DNA vaccines by plasmids coexpressing hepatitis B surface antigen and interleukin-2. Journal of Virology 1997; 71(1):169-78.

Cong Y. Weaver C T. Elson C O. The mucosal adjuvanticity of cholera toxin involves enhancement of costimulatory activity by selective up-regulation of B7.2 expression. J. Immunol. 1997; 159: 5301-8.

Constant S L. Bottomly K. Induction of Th1 and Th2 CD4+ T cell responses: the alternative approaches. Ann. Rev. Immunol. 1997; 15: 297-322.

Cowdery, J. S., J. H. Chace, and A. M. Krieg. 1996. Bacterial DNA induces in vivo interferon-γ production by NK cells and increases sensitivity to endotoxin. J. Immunol. 156: 4570.

Davis H L, Weeratna R, Waldschmidt T J, Schorr J and Krieg A M. CpG DNA is a potent adjuvant in mice immunized with recombinant hepatitis B surface antigen. J. Immunol. 1998; 160: 870-876.

de Haan L. Verweij W R. Feil I K. Lijnema T H. Hol W G. Agsteribbe E. Wilschut J. Mutants of the Escherichia coli heat-labile enterotoxin with reduced ADP-ribosylation activity or no activity retain the immunogenic properties of the native holotoxin. Infect. Immun. 1996; 64: 5413-6.

Delong R. Stephenson K. Loftus T. Fisher M. Alahari S, Nolting A. Juliano R L. Characterization of complexes of oligonucleotides with polyamidoamine starburst dendrimers and effects on intracellular delivery. J. Pharmac. Sci. 1997; 86: 762-4.

Douce G. Turcotte C. Cropley I. Roberts M. Pizza M. Domenghini M. Rappuoli R. Dougan G. Mutants of Escherichia coli heat-labile toxin lacking ADP-ribosyltransferase activity act as nontoxic, mucosal adjuvants. PNAS. 1995; 92: 1644-8.

Eldridge J, Staas J K., Meulbroek J A., McGhee J R. Biodegradable microspheres as a vaccine delivery system. Molecular Immunology 1991; 28: 287-294.

Gallichan W S, Rosenthal K L. Specific secretory immune responses in the female genital tract following intranasal immunization with a recombinant adenovirus expressing glycoprotein B of herpes simplex virus. Vaccine 1995; 13(16):1589-95.

Geissler M, Gesien A, Tokushige K, Wands J R. Enhancement of cellular and humoral immune responses to hepatitis C virus core protein using DNA-based vaccines augmented with cytokine-expressing plasmids. J Immunol 1997; 158 (3): 1231-7.

Gregoriadis G. Engineering liposomes for drug delivery: progress and problems. Trends Biotech. 1995; 13: 527-537.

Halpern, M. D., R. J. Kurlander, and D. S. Pisetsky. 1996. Bacterial DNA induces murine interferon-γ production by stimulation of interleukin-12 and tumor necrosis factor-α. Cell. Immunol. 167:72.

Haneberg B, Kendall D, Amerongen H M, Apter F M, Kraehenbuhl J-P, and Neutra M R. Induction of specific immunoglobulin A in the small intestine, colon-rectum, and vagina measured by a new method for collection of secretions from local mucosal surfaces. Infect. Immun. 1994; 15-23.

Hogg J C. The pathology of asthma. APMIS. 1997; 105; 10: 735-45.

Holmgren J, Lycke N, Czerkinsky C. Cholera toxin and cholera B subunit as oral-mucosal adjuvant and antigen vector systems. Vaccine 1993; 11:1179-1184.

Hornquist E. Lycke N. Cholera toxin adjuvant greatly promotes antigen priming of T cells. Eur. J. Immunol. 1993; 23: 2136-43.

Kay A B. TH2-type cytokines in asthma. Ann. NY Acad. Sci. 1996; 796: 1-8.

Kim J J, Ayyavoo V, Bagarazzi M L, Chattergoon M A, Dang K, Wang B, Boyer J D, and Weiner D B. In vivo engineering of a cellular immune response by coadministration of IL-12 expression vector with a DNA immunogen. J. Immunol. 1997; 158: 816-26.

Klinman D M, Yamshchikov G, and Ishigatsubo Y. Contribution of CpG motifs to the immunogenicity of DNA vaccines. J. Immunol. 1997; 158: 3635-3659.

Klinman, D., A.-K. Yi, S. L. Beaucage, J. Conover, and A. M. Krieg. 1996. CpG motifs expressed by bacterial DNA rapidly induce lymphocytes to secrete IL-6, IL-12 and IFN. *Proc. Natl. Acad. Sci. USA* 93:2879.

Krieg, A. M., A.-K. Yi, S. Matson, T. J. Waldschmidt, G. A. Bishop, R. Teasdale, G. Koretzky, and D. Klinman. CpG motifs in bacterial DNA trigger direct B-cell activation. 1995. *Nature* 374:546.

Krieg, A. M. 1996 An innate immune defense mechanism based on the recognition of CpG motifs in microbial DNA. *J. Lab. Clin. Med.* 128:128.

Kukowska-Latallo J F. Bielinska A U. Johnson J. Spindler R. Tomalia D A. Baker J R Jr. Efficient transfer of genetic material into mammalian cells using Starburst polyamidoamine dendrimers. PNAS. 1996; 93: 4897-902.

Lamm M E, Mazanec M B, Nedrud J G, Kaetzel C S. Mechanisms of IgA-mediated mucosal defense. Vaccine Res. 1992; 1:169-173.

Lycke N, Tsuji T, and Holmgren J. The adjuvant effect of *Vibrio cholerae* and *Escherichia coli* heat-labile enterotoxins is linked to their ADP-ribosyltransferase activity. Eur. J. immunol. 1992; 22: 2277-2281.

Maloy K J. Donachie A M. Mowat A M. Induction of Th1 and Th2 CD4+ T cell responses by oral or parenteral immunization with ISCOMS. Eur. J. Immunol. 1995; 25: 2835-41.

Mannino R J and Gould-Fogerite S. Lipid matrix-based vaccines for mucosal and systemic immunization. In: Vaccine Design; The subunit and adjuvant approach. (ed. Powell M F and Newman M J) Plenum Press, New York. 1995; 363-387.

McGhee J R, Mestecky J, Dertzbaugh M T, Eldridge J H, Hirasawa M, Kiyono H. The mucosal immune system: from fundamental concepts to vaccine development. Vaccine 1992; 10:75-88.

Messina, J. P., G. S. Gilkeson, and D. S. Pisetsky. 1991. Stimulation of in vitro murine lymphocyte proliferation by bacterial DNA. *J. Immunol.* 147:1759.

Mestecky J, McGhee J R. Prospects for human mucosal vaccines. In: Ciardi J E, ed. Genetically Engineered vaccines. New York: Plenum Press, 1992:13-23.

O'Hagan D T. Oral immunization and the common mucosal immune system. In: O'Hagan D T, ed. Novel Delivery Systems for Oral Vaccines. Boca Raton: CRC Press, 1994: 1-24.

O'Hagan D T, Rahman D, Jeffery H, Sharif S, Challacombe S J. Controlled release microparticles for oral immunization. Int. J. Pharm. 1994; 108: 133-139.

Pizza M. Fontana M R. Giuliani M M. Domenighini M. Magagnoli C. Giannelli V. Nucci D. Hol W. Manetti R. Rappuoli R. A genetically detoxified derivative of heat-labile *Escherichia coli* enterotoxin induces neutralizing antibodies against the A subunit. J. Exp. Med. 1994; 180: 2147-53.

Rappuoli R. Douce G. Dougan G. Pizza M. Genetic detoxification of bacterial toxins: a new approach to vaccine development. Int Arch Allergy Immunol. 1995; 108: 327-33.

Sato Y. Roman M. Tighe H. Lee D. Corr M. Nguyen M D. Silverman G J. Lotz M. Carson D A. Raz E. Immunostimulatory DNA sequences necessary for effective intradermal gene immunization. Science. 1996; 273: 352-4.

Schirmbeck R, Melber, K, Kuhröber A, Janowicz Z A and Reimann J. Immunization with soluble hepatitis B virus surface protein elicits murine H-2 class I-restricted CD8+ cytotoxic T lymphocyte responses in vivo. J. Immunol. 1994; 152: 1110-1119.

Sjolander A. Lovgren Bengtsson K. Johansson M. Morein B. Kinetics, localization and isotype profile of antibody responses to immune stimulating complexes (ISCOMS) containing human influenza virus envelope glycoproteins. Scand. J. Immunol. 1996; 43:164-72.

Sjolander A. van't Land B. Lovgren Bengtsson K. Iscoms containing purified *Quillaja saponins* upregulate both Th1-like and Th2-like immune responses. Cell. Immunol. 1997; 177: 69-76.

Snider D P. The mucosal adjuvant activities of ADP-ribosylating bacterial enterotoxins. Crit. Rev. Immunol. 1995; 15: 317-48.

Spangler B D. Structure and function of cholera toxin and the related *Escherichia coli* heat-labile enterotoxin. Microbiol. Rev. 1992; 56: 622-647.

Staats H F, Jackson R J, Marinaro M, Takahashi I, Kiyono H, McGhee J R. Mucosal immunity to infection with implications for vaccine development. Current Biology. 1994; 6:572-583.

Tokunaga, T, H. Yamamoto, S. Shimada, H. Abe, T. Fukuda, Y. Fujisawa, Y. Furutani, O. Yano, T. Kataoka, T. Sudo, N. Makiguchi, and T. Suganuma. 1984. Antitumor activity of deoxyribonucleic acid fraction from *mycobacterium bovis* GCG. I. Isolation, physicochemical characterization, and antitumor activity. *JNCI* 72:955.

Tsuji T, Hamajima K, Ishii N, Aoki I, Fukushima J, Xin K Q, Kawamoto S, Sasaki S, Matsunaga K, Ishigatsubo Y, Tani K, Okubo T, and Okuda K. Immunomodulatory effects of a plasmid expressing B7-2 on human immunodeficiency virus-1-specific cell-mediated immunity induced by a plasmid encoding the viral antigen. Eur. J. Immunol. 1997; 27: 782-7.

Valodas, J., Davies, J. K., Wright, P. J., Strugnell R. A. Intranasal immunization with liposomes induces strong mucosal immune responses in mice. Eur. J. Immunol. 1995; 25: 969-975.

Weeratna R, Brazolot Millan C L, Krieg A M, and Davis H L. Reduction of antigen expression from DNA vaccines by co-administered oligodeoxynucleotides. Anti. Nucl. Acid Res. (in press).

Yamamoto, S., T. Yamamoto, S. Shimada, E. Kuramoto, O. Yano, T. Kataoka, and T. Tokunaga. 1992. DNA from bacteria, but not from vertebrates, induces interferons, activates natural killer cells and inhibits tumor growth. Microbiol. Immunol. 36:983.

Yi, A.-K., Cowdery, J. S., J. H. Chace, and A. M. Krieg. 1996. IFN-γ promotes IL-6 and Ig-M secretion in response to CpG motifs in bacterial DNA and ODN. *J. Immunol.*, 156: 558.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A method for inducing a mucosal immune response, comprising:
   administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides, and
   an antigen,
      wherein the antigen is not encoded in a nucleic acid vector, the oligonucleotide and the antigen are both administered vaginally, rectally, intranasally, ocularly, or by inhalation to the subject, a cytokine and an immune stimulating complex are not administered to the subject, and the antigen is not a *Streptococcus pneumoniae* antigen.

2. The method of claim 1, wherein the antigen is administered concurrently with the oligonucleotide.

3. The method of claim 1, wherein the antigen is delivered in conjunction with a colloidal dispersion system.

4. The method of claim 3, wherein the colloidal dispersion system is selected from the group consisting of macromolecular complexes, nanocapsules, microspheres, beads, and lipid-based systems.

5. The method of claim 4, wherein the lipid-based system is selected from the group consisting of oil-in-water emulsions, micelles, mixed micelles, and liposomes.

6. The method of claim 1, further comprising the step of administering a non-oligonucleotide mucosal adjuvant in conjunction with the antigen.

7. The method of claim 6, wherein the non-oligonucleotide mucosal adjuvant is selected from the group consisting of cholera toxin, derivatives of cholera toxin, heat-labile enterotoxin, derivatives of heat-labile enterotoxin, alum, monophosphoryl lipid A (MLP), muramyl dipeptide (MDP), saponins, QS21, cytokines, oil-in-water and other emulsion formulations, squalene-in-water emulsion stabilized with Span 85 and Tween 80 (MF59), syntext adjuvant formulation (SAF), Montanide ISA 720 and oil-in-water emulsion containing stabilizing detergent and micelle-forming agent and poly (PCPP) polymers.

8. The method of claim 1, wherein the subject is a subject at risk of developing an infectious disease.

9. The method of claim 1, wherein the subject is at risk of developing cancer.

10. The method of claim 1, wherein the oligonucleotide includes a phosphate backbone modification which is a phosphorothioate or phosphorodithioate modification.

11. The method of claim 10, wherein the phosphate backbone modification occurs at the 5' end of the oligonucleotide.

12. The method of claim 10, wherein the phosphate backbone modification occurs at the 3' end of the oligonucleotide.

13. The method of claim 1, wherein X1X2 are nucleotides selected from the group consisting of: GpT, GpG, GpA, ApA, ApT, ApG, CpT, CpA, CpG, TpA, TpT, and TpG; and X3X4 are nucleotides selected from the group consisting of: TpT, CpT, ApT, TpG, ApG, CpG, TpC, ApC, CpC, TpA, ApA, and CpA.

14. The method of claim 1, wherein the oligonucleotide has a sequence including at least the following formula:

5'TCNTX1X2CGX3X4 3' wherein X1, X2, X3, and X4 are nucleotides, N is a nucleic acid sequence composed of from about 0-25 nucleotides.

15. The method of claim 1, wherein the antigen is selected from the group consisting of cells, cell extracts, proteins, polypeptides, peptides, polysaccharides, polysaccharide conjugates, peptide mimics of polysaccharides, lipids, glycolipids, carbohydrates, viruses and viral extracts and parasites.

16. The method of claim 1, wherein the antigen is obtained from an infectious organism selected from the group consisting of infectious bacteria, infectious viruses, infectious parasites, and infectious fungi.

17. The method of claim 1, further comprising administering a B-7 costimulatory molecule.

18. The method of claim 1, wherein the mucosal immune response is induced in a remote site.

19. The method of claim 1, further comprising administering a boost of the oligonucleotide.

20. The method of claim 6, further comprising administering a boost of the oligonucleotide and the non-oligonucleotide mucosal adjuvant.

21. The method of claim 1, further comprising identifying a subject in need of a mucosal immune response.

22. The method of claim 1, wherein the antigen is a viral antigen.

23. A method for inducing a mucosal immune response, comprising:
administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides,
a non-oligonucleotide mucosal adjuvant that is not an immune stimulating complex, and
an antigen,
wherein the antigen is not encoded in a nucleic acid vector, and wherein the oligonucleotide, the antigen, and the non-oligonucleotide mucosal adjuvant are all administered rectally, intravaginally, or ocularly, to the subject, and a cytokine is not administered to the subject.

24. A method for inducing a mucosal immune response, comprising:
administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides, and
a viral antigen,
wherein the antigen is not encoded in a nucleic acid vector, the oligonucleotide and the antigen are both administered vaginally, rectally, intranasally, ocularly, or by inhalation to the subject, and a cytokine and an immune stimulating complex are not administered to the subject.

25. A method for inducing a mucosal immune response, comprising:
administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides, and
passively exposing the subject to an antigen,
wherein the antigen is not encoded in a nucleic acid vector, oligonucleotide administration and antigen exposure both occur vaginally, rectally, intranasally, or by inhalation, and a cytokine and an immune stimulating complex are not administered to the subject.

26. A method for inducing a mucosal immune response, comprising:
administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides, and
an antigen,
wherein the antigen is not encoded in a nucleic acid vector, the oligonucleotide and the antigen are both administered vaginally, rectally, or ocularly to the subject, and a cytokine and an immune stimulating complex are not administered to the subject.

27. The method of claim 26, wherein the antigen is a viral antigen.

28. A method for inducing a mucosal immune response, comprising:
administering to a subject in need of a mucosal immune response an effective amount for inducing a mucosal immune response of an oligonucleotide 8 to 100 nucleotides in length, having a sequence including at least the following formula:

5'X1X2CGX3X4 3' wherein C is unmethylated, wherein X1, X2, X3, and X4 are nucleotides, and
an antigen,
wherein the antigen is not encoded in a nucleic acid vector and is not a *Streptococcus pneumoniae* antigen, the oligonucleotide and the antigen are both administered intranasally or by inhalation to the subject, and a cytokine and an immune stimulating complex are not administered to the subject.

29. The method of claim 23, wherein the antigen is selected from the group consisting of cells, cell extracts, proteins, polypeptides, peptides, polysaccharides, polysaccharide conjugates, peptide mimics of polysaccharides, lipids, glycolipids, carbohydrates, viruses and viral extracts and parasites.

30. The method of claim 25, wherein the antigen is selected from the group consisting of cells, cell extracts, proteins, polypeptides, peptides, polysaccharides, polysaccharide conjugates, peptide mimics of polysaccharides, lipids, glycolipids, carbohydrates, viruses and viral extracts and parasites.

31. The method of claim 26, wherein the antigen is selected from the group consisting of cells, cell extracts, proteins, polypeptides, peptides, polysaccharides, polysaccharide conjugates, peptide mimics of polysaccharides, lipids, glycolipids, carbohydrates, viruses and viral extracts and parasites.

32. The method of claim 28, wherein the antigen is selected from the group consisting of cells, cell extracts, proteins, polypeptides, peptides, polysaccharides, polysaccharide conjugates, peptide mimics of polysaccharides, lipids, glycolipids, carbohydrates, viruses and viral extracts and parasites.

33. A method for inducing a mucosal immune response, comprising
mucosally administering to a subject an oligonucleotide 8 to 100 nucleotides in length and comprising 5'X1X2CGX3X4 3' wherein C is unmethylated and X1, X2, X3, and X4 are nucleotides, and an antigen that is not encoded in a nucleic acid vector, and
systemically administering to the subject the antigen.

34. The method of claim 33, wherein the oligonucleotide and antigen are administered mucosally as a priming dose, and the antigen is administered systemically as a boost dose.

35. The method of claim 33, wherein the antigen is administered systemically as a priming dose, and the oligonucleotide and antigen are administered mucosally as a boost dose.

36. The method of claim 33, wherein the antigen is administered systemically with a CpG oligonucleotide 8-100 nucleotides in length and comprising 5'X1X2CGX3X4 3', wherein C is unmethylated, wherein X1, X2, X3, and X4 are nucleotides.

37. The method of claim 33, wherein the oligonucleotide and antigen are administered mucosally with a non-nucleic acid mucosal adjuvant.

38. The method of claim 33, wherein the antigen is administered systemically with a non-nucleic acid mucosal adjuvant.

39. The method of claim 26, wherein the antigen is administered systemically with a non-nucleic acid mucosal adjuvant.

40. The method of claim 33, wherein the antigen is a polypeptide or a peptide.

41. The method of claim 33, wherein mucosally administering is intranasally administering or administering by inhalation.

42. The method of claim 40, wherein mucosally administering is intranasally administering or administering by inhalation.

43. The method of claim 33, wherein systemically administering is intramuscularly administering.

44. The method of claim 40, wherein systemically administering is intramuscularly administering.

45. The method of claim 42, wherein systemically administering is intramuscularly administering.

46. A method for inducing an immune response, comprising
systemically administering to a subject, as a priming dose, an antigen that is not encoded in a nucleic acid vector, and
mucosally administering to the subject, as a boost dose, an oligonucleotide 8-100 nucleotides in length and comprising 5'X1X2CGX3X4 3' wherein C is unmethylated and X1, X2, X3, and X4 are nucleotides, and the antigen.

47. The method of claim 46, wherein the antigen is systemically administered with a CpG oligonucleotide 8-100 nucleotides in length and comprising 5'X1X2CGX3X4 3' wherein C is unmethylated and X1, X2, X3, and X4 are nucleotides.

48. The method of claim 46, wherein the antigen is systemically administered with a non-nucleic acid mucosal adjuvant.

49. The method of claim 47, wherein the antigen is systemically administered with a non-nucleic acid mucosal adjuvant.

50. The method of claim 46, wherein the antigen is mucosally administered to the subject with a non-nucleic acid mucosal adjuvant.

51. The method of claim 49, wherein the antigen is mucosally administered to the subject with a non-nucleic acid mucosal adjuvant.

52. A method for inducing a mucosal immune response in a subject, comprising
mucosally administering to a subject, as a boost dose, an oligonucleotide 8-100 nucleotides in length and comprising 5'X1X2CGX3X4 3' wherein C is unmethylated and X1, X2, X3, and X4 are nucleotides, and an antigen that is not encoded by a nucleic acid vector, wherein the subject has received a priming dose of antigen administered systemically.

* * * * *

UNITED STATES PATENT AND TRADEMARK OFFICE
CERTIFICATE OF CORRECTION

PATENT NO. : 8,574,599 B1  
APPLICATION NO. : 09/316199  
DATED : November 5, 2013  
INVENTOR(S) : Michael J. McCluskie et al.

Page 1 of 1

It is certified that error appears in the above-identified patent and that said Letters Patent is hereby corrected as shown below:

*In the Claims:*

At column 81, Claim 39, line 46, please delete "claim 26" and insert --claim 36--.

Signed and Sealed this  
Twenty-fifth Day of February, 2014

Michelle K. Lee  
*Deputy Director of the United States Patent and Trademark Office*